(12) United States Patent
Karuppasamy

(10) Patent No.: US 11,793,658 B2
(45) Date of Patent: Oct. 24, 2023

(54) METHOD AND APPARATUSES FOR DEPLOYING AN IMPLANT

(71) Applicant: THE CLEVELAND CLINIC FOUNDATION, Cleveland, OH (US)

(72) Inventor: Karunakaravel Karuppasamy, Cleveland, OH (US)

(73) Assignee: THE CLEVELAND CLINIC FOUNDATION, Cleveland, OH (US)

( * ) Notice: Subject to any disclaimer, the term of this patent is extended or adjusted under 35 U.S.C. 154(b) by 1047 days.

(21) Appl. No.: 16/492,669

(22) PCT Filed: Mar. 9, 2018

(86) PCT No.: PCT/US2018/021755
§ 371 (c)(1),
(2) Date: Sep. 10, 2019

(87) PCT Pub. No.: WO2018/165555
PCT Pub. Date: Sep. 13, 2018

(65) Prior Publication Data
US 2020/0046532 A1   Feb. 13, 2020

Related U.S. Application Data

(60) Provisional application No. 62/469,566, filed on Mar. 10, 2017.

(51) Int. Cl.
*A61F 2/954* (2013.01)
*A61F 2/97* (2013.01)
*A61F 2/966* (2013.01)

(52) U.S. Cl.
CPC ............ *A61F 2/954* (2013.01); *A61F 2/97* (2013.01); *A61F 2002/9665* (2013.01)

(58) Field of Classification Search
CPC .... A61F 2/954; A61F 2/97; A61F 2002/9665; A61M 25/0668; A61M 2025/0675
See application file for complete search history.

(56) References Cited

U.S. PATENT DOCUMENTS 5,980,533 A   11/1999   Holman
6,143,002 A   11/2000   Metmeier
(Continued)

FOREIGN PATENT DOCUMENTS

EP   2036519 A1   3/2009
WO   99/34749 A1   7/1999

OTHER PUBLICATIONS

PCT International Search Report and Written Opinion for corresponding International Application Serial No. PCT/US2018/021731, dated May 22, 2018, pp. 1-14.
(Continued)

*Primary Examiner* — Diane D Yabut
(74) *Attorney, Agent, or Firm* — TAROLLI, SUNDHEIM, COVELL & TUMMINO LLP

(57) ABSTRACT

An implant delivery system is provided for deploying an expandable implant in a patient lumen. An outer sheath has an outer sheath lumen that extends between an outer sheath proximal opening and an outer sheath open tip. At least one outer sheath side wall opening selectively places an outer sheath outer surface in fluid communication with the outer sheath lumen. At least one outer sheath open slit extends at least partially between the outer sheath open tip and a respective outer sheath side wall opening. A shaft has at least one shaft side wall opening that selectively places a shaft outer surface in fluid communication with at least one shaft lumen. When the shaft is operably joined to the outer sheath,
(Continued)

at least a portion of the at least one shaft side wall opening is selectively aligned with a respective outer sheath side wall opening.

31 Claims, 45 Drawing Sheets

(56) References Cited

U.S. PATENT DOCUMENTS

| | | | |
|---|---|---|---|
| 6,908,477 B2 | 6/2005 | McGuckin, Jr. et al. | |
| 7,476,243 B2 | 1/2009 | Eidenschink | |
| 7,481,837 B2 | 1/2009 | Wilson | |
| 8,128,686 B2 | 3/2012 | Paul, Jr. et al. | |
| 8,968,383 B1* | 3/2015 | Johnson | A61F 2/82 |
| | | | 604/525 |
| 9,125,764 B2 | 9/2015 | Shaw | |
| 9,623,603 B2 | 4/2017 | Hamer et al. | |
| 2003/0135259 A1 | 7/2003 | Simso | |
| 2007/0244540 A1* | 10/2007 | Pryor | A61F 2/966 |
| | | | 623/1.11 |
| 2008/0167705 A1* | 7/2008 | Agnew | A61F 2/95 |
| | | | 623/1.12 |
| 2010/0268318 A1 | 10/2010 | Glynn | |
| 2011/0137395 A1* | 6/2011 | Fargahi | A61F 2/95 |
| | | | 623/1.11 |
| 2012/0016454 A1 | 1/2012 | Jantzen et al. | |
| 2012/0130475 A1 | 5/2012 | Shaw | |
| 2016/0242943 A1 | 8/2016 | Riedy et al. | |

OTHER PUBLICATIONS

PCT International Search Report and Written Opinion for corresponding International Application Serial No. PCT/US2018/021755, dated May 17, 2018, pp. 1-14.

* cited by examiner

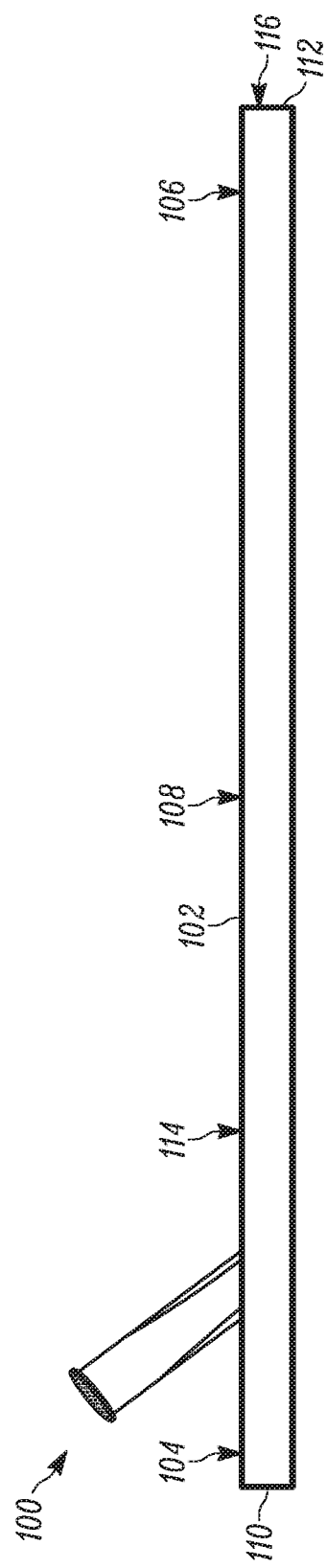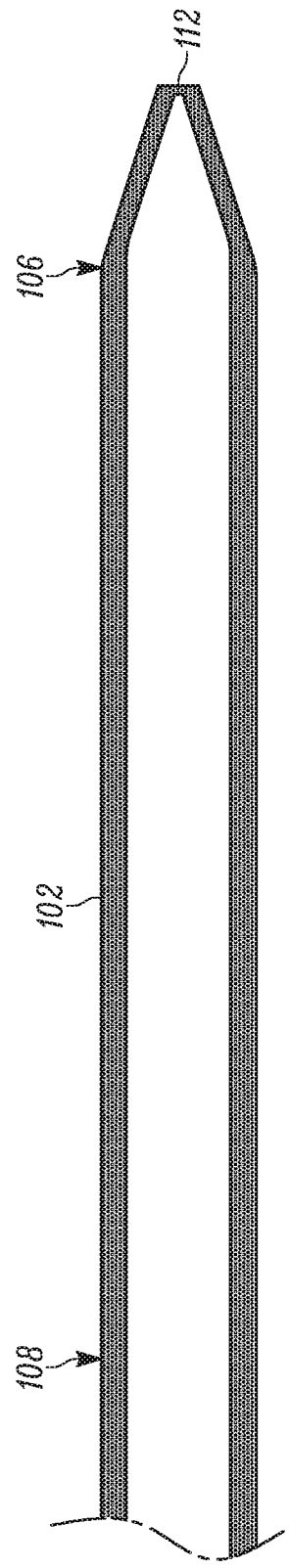

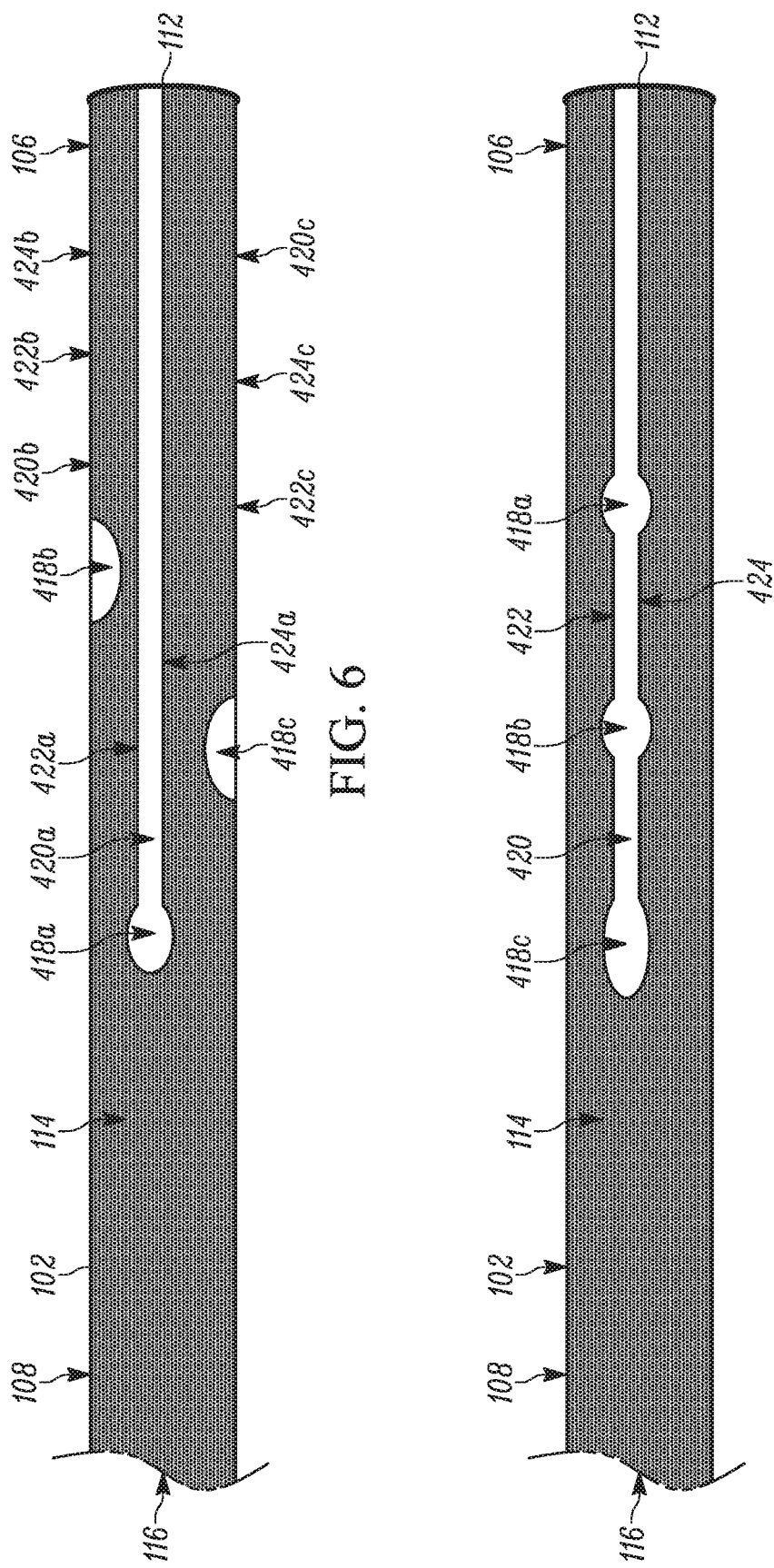

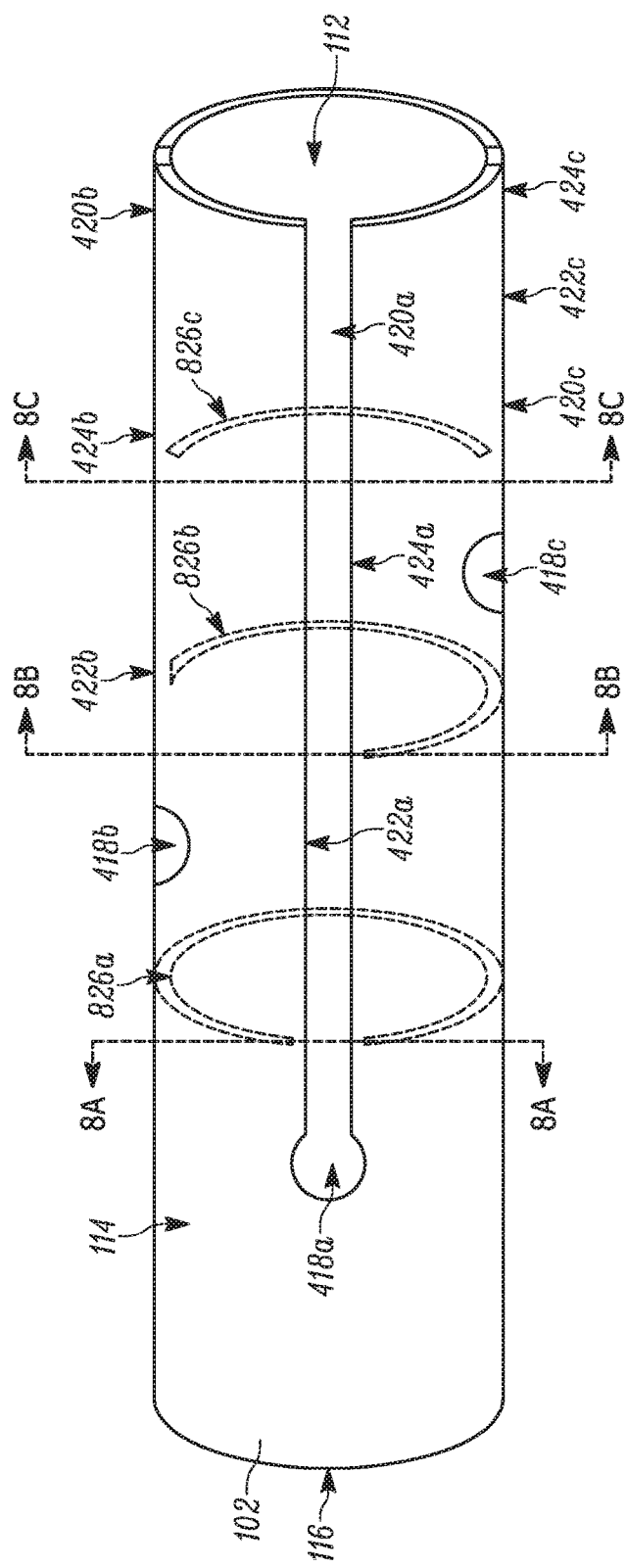
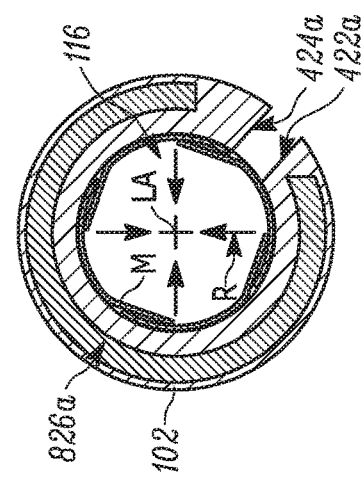
FIG. 8
FIG. 8A

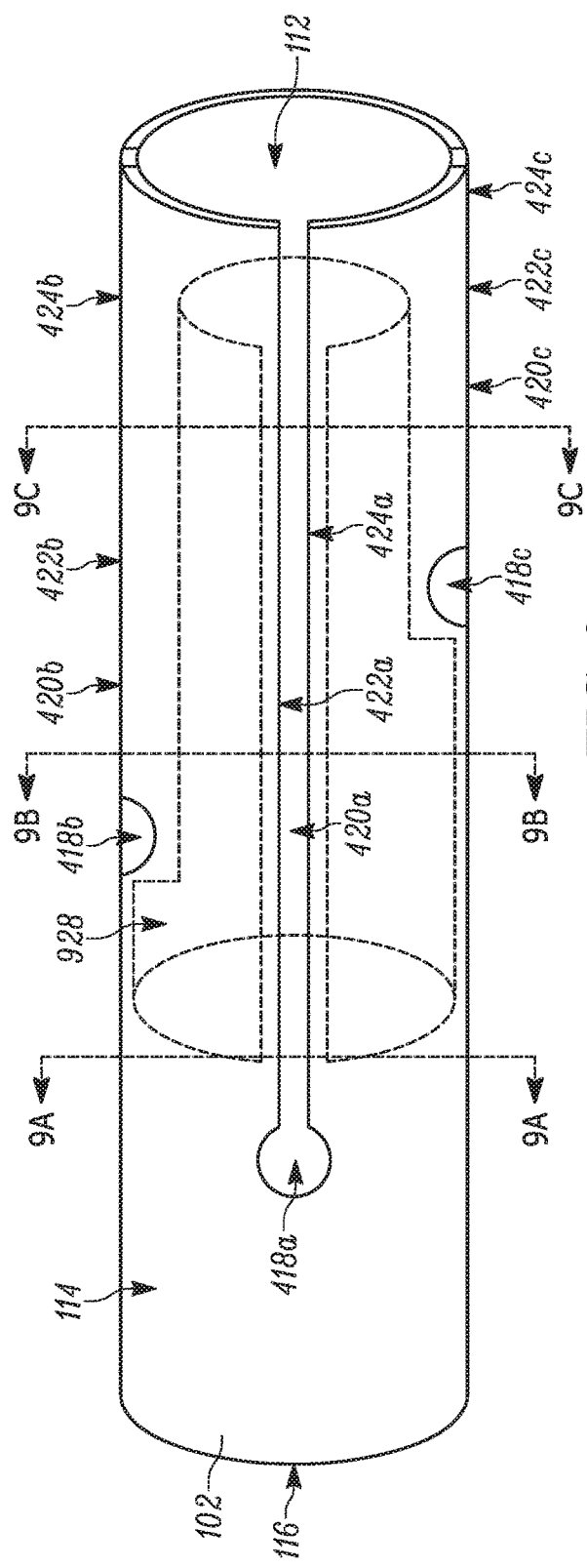
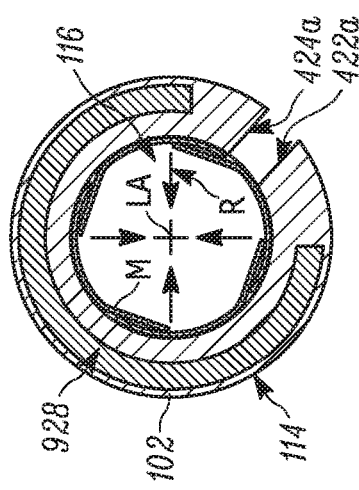
FIG. 9
FIG. 9A

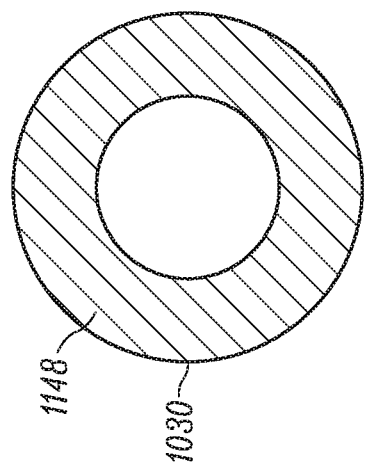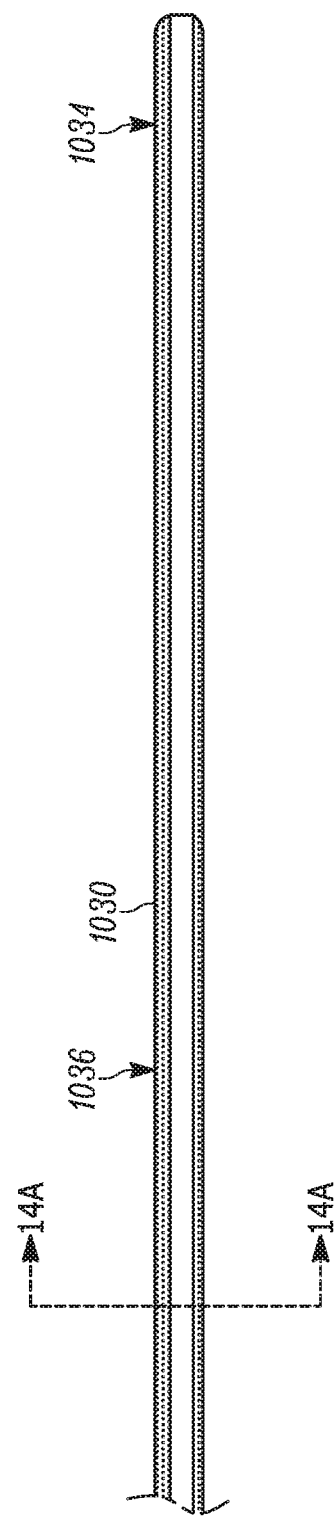

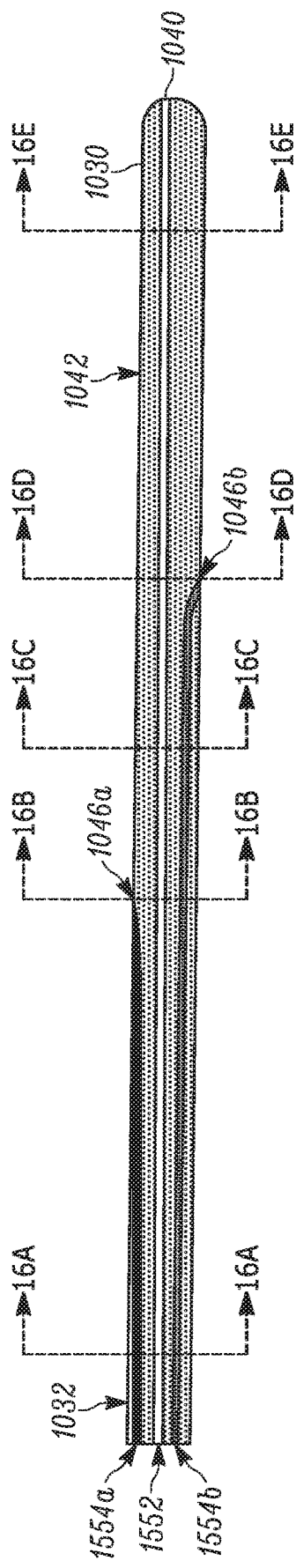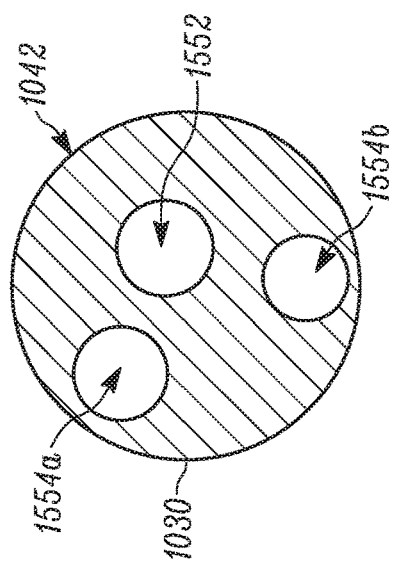
FIG. 16
FIG. 16A

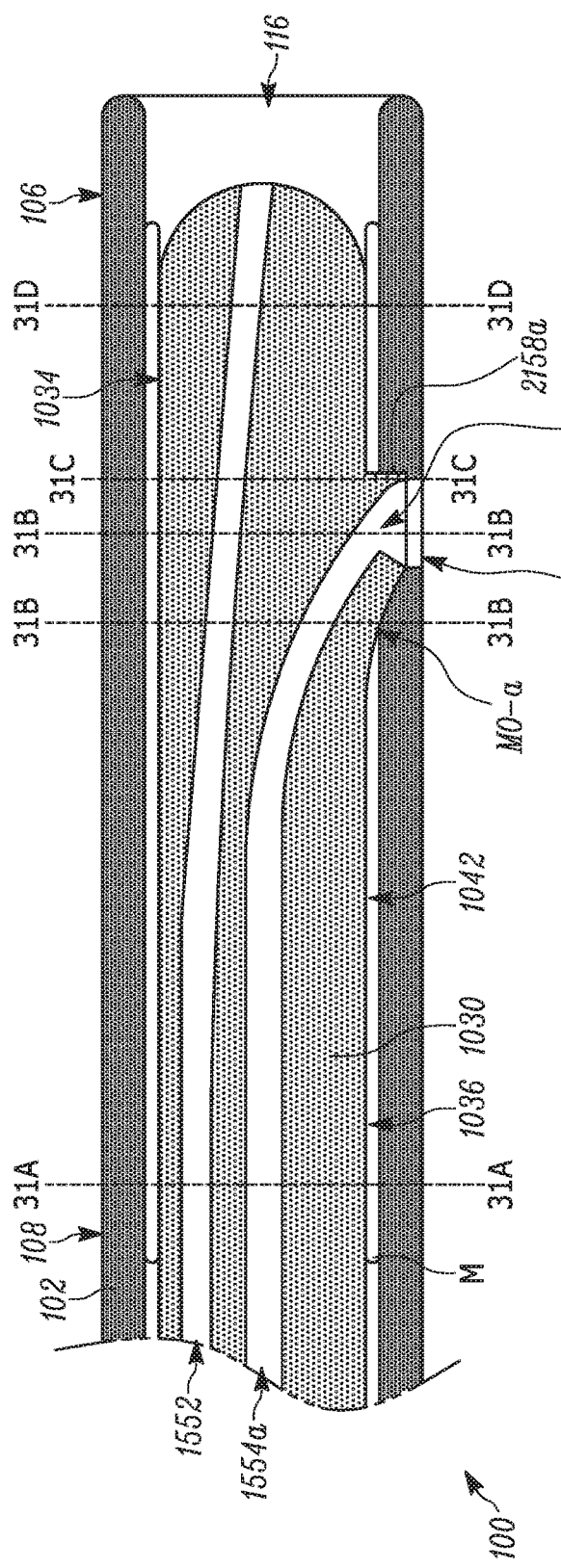
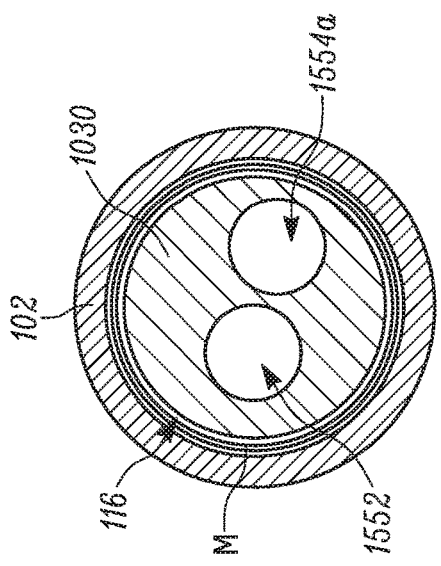
FIG. 31
FIG. 31A

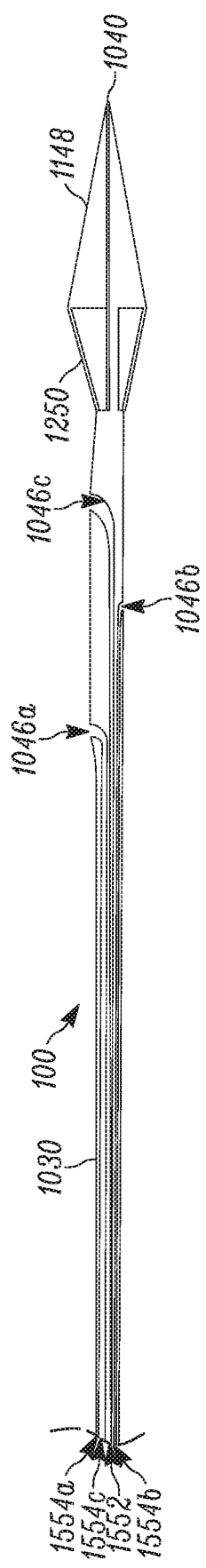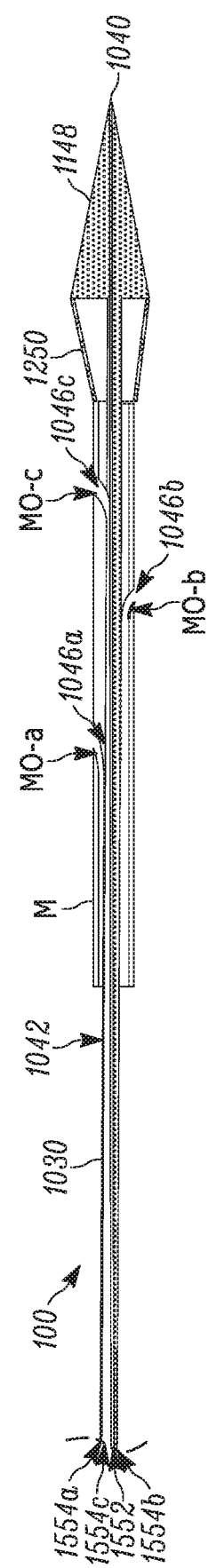

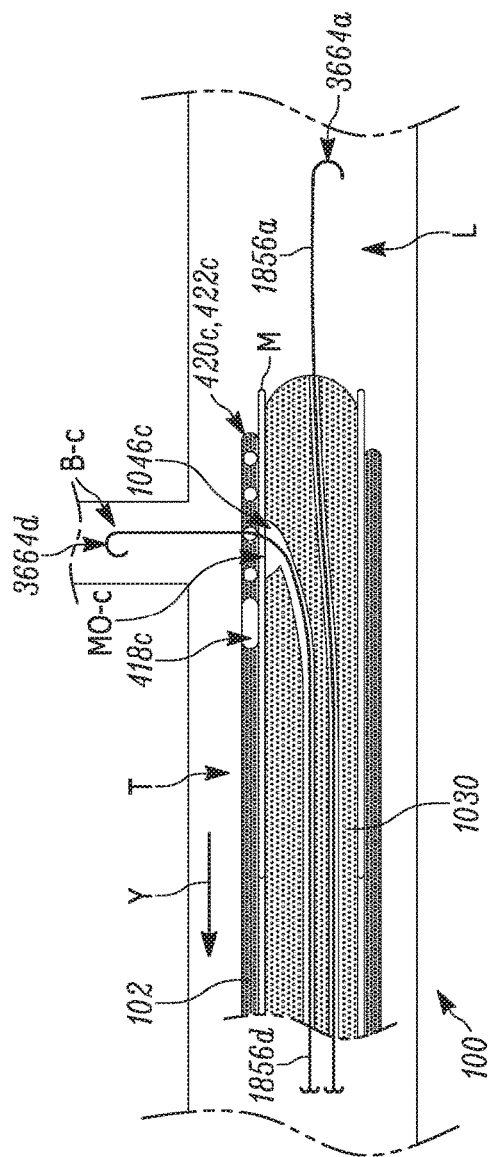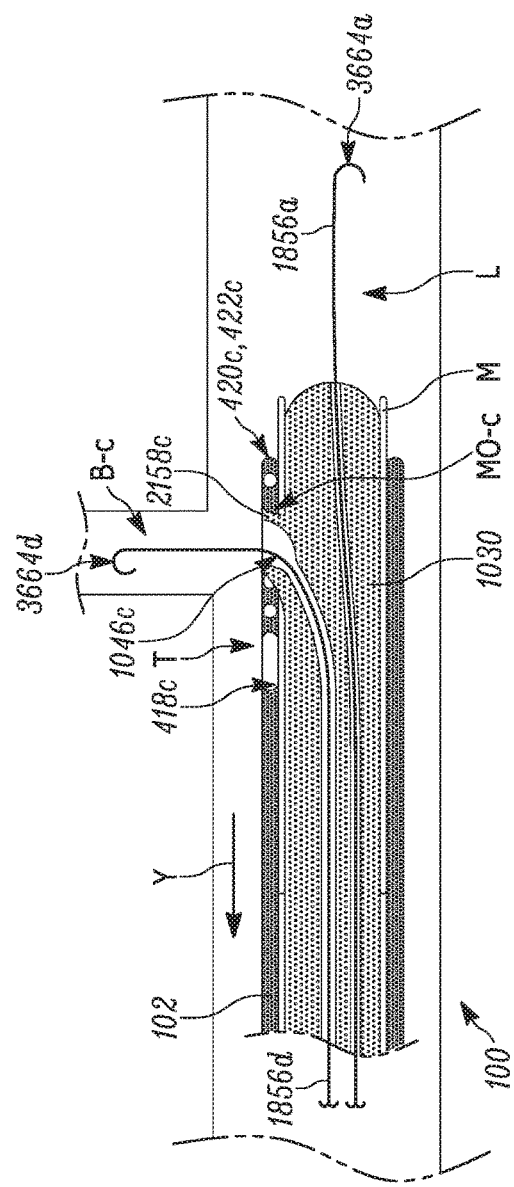

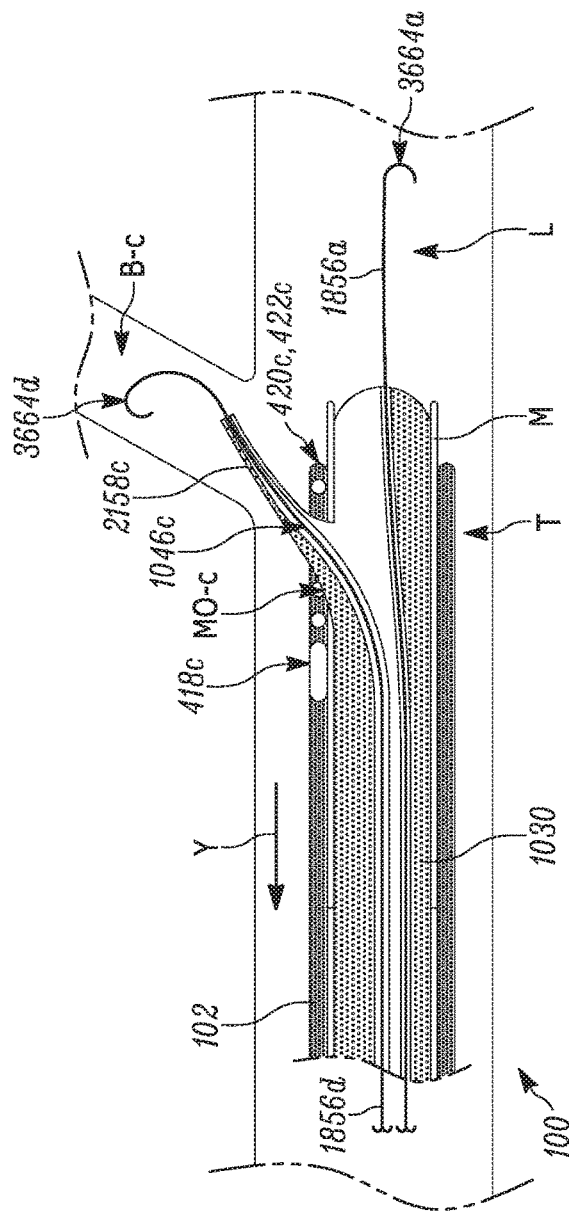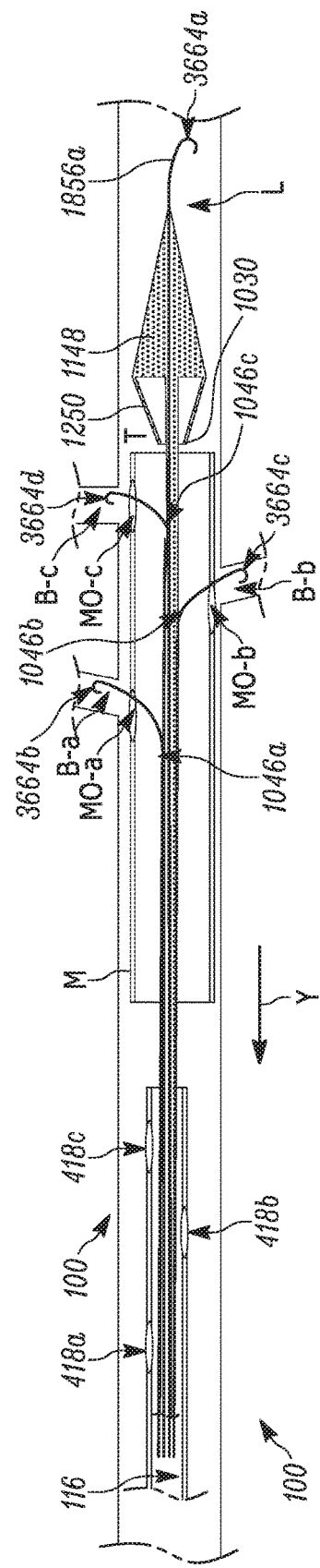
FIG. 41
FIG. 42

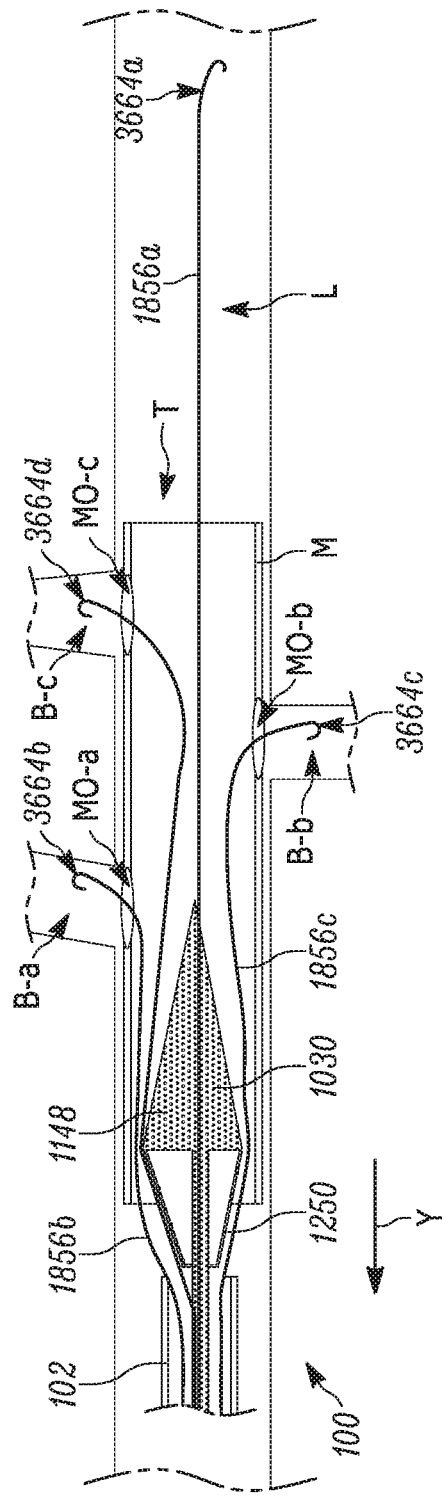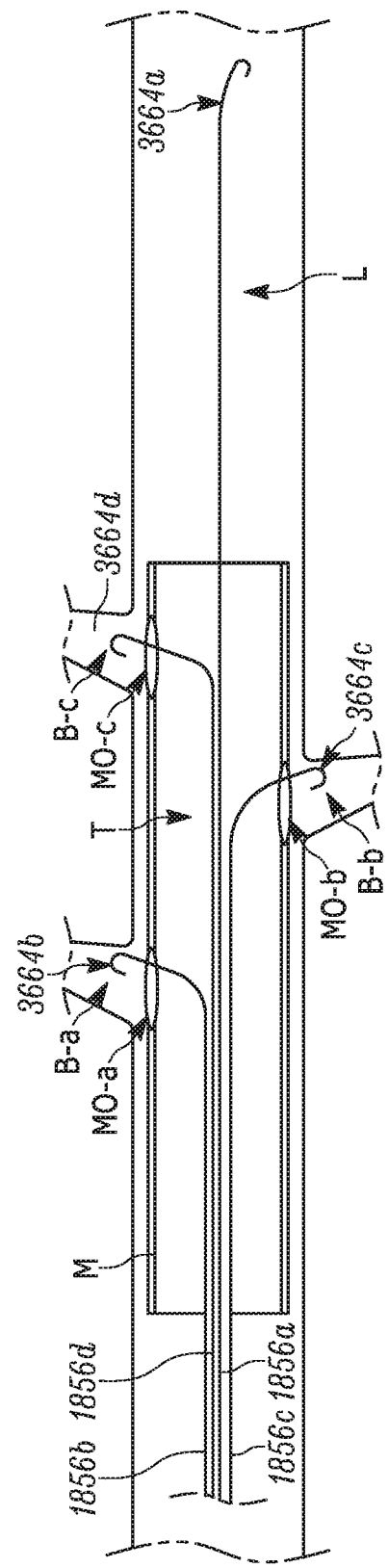

METHOD AND APPARATUSES FOR DEPLOYING AN IMPLANT

RELATED APPLICATION

This application is a national phase application of and claims priority from PCT International Patent Application PCT/US2018/021755, filed Mar. 9, 2018, which claims priority from U.S. Provisional Application No. 62/469,566, filed 10 Mar. 2017 and entitled SELF EXPANDING BIFURCATION STENT DELIVERY SYSTEMS AND BIFURCATED BALLOONS. The subject matter of each of the aforementioned applications is hereby incorporated by reference in its entirety.

TECHNICAL FIELD

This disclosure relates to apparatuses and methods for use of an implant delivery system and, more particularly, to a method and device for deploying an expandable implant in a patient lumen.

BACKGROUND

It is often desirable to use multiple guidewires in various medical procedures involving diseased branched patient lumens. For example, when utilizing stent deployment devices within branched lumens, a first guidewire would be used to access the main lumen while second and/or third guidewires would access the side branch lumens. At least one stent with at least one guidewire port may be collapsed and inserted within a delivery device, such as a catheter. The delivery device may be advanced along the respective guidewires to the diseased portion of the patient lumen. Once at the desired position for stent deployment in the branched patient lumen, the stent may be deployed from the delivery device and expanded.

SUMMARY

In an aspect, an implant delivery system is provided. An outer sheath has an outer sheath proximal end having an outer sheath proximal opening. An outer sheath distal end has an outer sheath open tip. The outer sheath has an outer sheath outer surface. An outer sheath lumen extends between the outer sheath proximal opening and the outer sheath open tip. The outer sheath lumen is for selectively holding at least one expandable implant therein. At least one outer sheath side wall opening selectively places the outer sheath outer surface in fluid communication with the outer sheath lumen. At least one outer sheath open slit extends at least partially between the outer sheath open tip and a respective outer sheath side wall opening. A shaft has a shaft proximal end having a shaft proximal opening. A shaft distal end has a shaft open tip. The shaft has a shaft outer surface and at least one shaft lumen. At least one shaft side wall opening selectively places the shaft outer surface in fluid communication with the at least one shaft lumen. When the shaft is operably joined to the outer sheath, at least a portion of the at least one shaft side wall opening is selectively aligned with a respective outer sheath side wall opening.

In an aspect, a method for deploying an expandable implant in a patient lumen is provided. An implant delivery system is provided. An outer sheath has an outer sheath proximal end having an outer sheath proximal opening. An outer sheath distal end has an outer sheath open tip. The outer sheath has an outer sheath outer surface. An outer sheath lumen extends between the outer sheath proximal opening and the outer sheath open tip. The outer sheath lumen is for selectively holding at least one expandable implant therein. At least one outer sheath side wall opening selectively places the outer sheath outer surface in fluid communication with the outer sheath lumen. At least one outer sheath open slit extends at least partially between the outer sheath open tip and a respective outer sheath side wall opening. A shaft has a shaft proximal end having at least one shaft proximal opening. A shaft distal end has a shaft open tip. The shaft has a shaft outer surface and at least one shaft lumen. At least one shaft side wall opening selectively places the shaft outer surface in fluid communication with the at least one shaft lumen. At least one expandable implant has at least one expandable implant side wall opening is provided. The at least one collapsed expandable implant is mounted circumferentially on the shaft outer surface. With the at least one collapsed expandable implant mounted on the shaft, at least a portion of the expandable implant side wall opening is aligned with at least a portion of a respective shaft side wall opening. The at least one collapsed expandable implant and at least a portion of the shaft are collectively inserted into at least a portion of the outer sheath lumen. With the at least one expandable implant and at least a portion of the shaft inserted into the outer sheath lumen, the shaft is aligned in the outer sheath lumen with at least a portion of the at least one shaft side wall opening being aligned with at least a portion of a respective outer sheath side wall opening. At least one guidewire distal end is inserted into a target patient tissue site in a patient lumen. At least one guidewire proximal end is directed through the implant delivery system. The implant delivery system is directed to the target patient tissue site along the at least one guidewire. With the implant delivery system at the target patient tissue site, the at least one expandable implant is exposed by directing the outer sheath in the longitudinally proximal direction, while maintaining each of the at least one guidewire, the at least one expandable implant and the shaft at the target patient tissue site. With the at least one expandable implant exposed, the properties of the at least one expandable implant are utilized to move the at least one expandable implant toward an expanded condition.

BRIEF DESCRIPTION OF THE DRAWINGS

For a better understanding, reference may be made to the accompanying drawings, in which:

FIG. 1 is a schematic side view of an element of an implant delivery system according to one aspect of the present invention;

FIG. 2 is a schematic side view of the aspect of FIG. 1, including a first option for a component;

FIG. 6 is a schematic top view of the aspect of FIG. 1, including a third option for a component;

FIG. 7 is a schematic top view of the aspect of FIG. 1, including a fourth option for a component;

FIG. 8 is a schematic top view of an element of the aspect of FIG. 1;

FIGS. 8a-c depict cross-sectional views of the aspect of FIG. 8;

FIG. 9 is a schematic top view of an element of the aspect of FIG. 1;

FIGS. 9a-c depict cross-sectional views of the aspect of FIG. 9;

FIGS. 13a-d depict cross-sectional views of the aspect of FIG. 13;

FIG. 14 is a schematic side view of the aspect of FIG. 10, including a first option for a component;

FIG. 16 is a schematic side view of the aspect of FIG. 10, including a third option for a component;

FIGS. 16a-e depict cross-sectional views of the aspect of FIG. 16;

FIG. 31 is a schematic side view of an aspect of the implant delivery system in a fifth example use configuration;

FIGS. 31a-e depict cross-sectional views of the aspect of FIG. 31;

FIGS. 33-44 illustrate an example sequence of operation of a portion of the implant delivery system in a first example use configuration;

DESCRIPTION OF ASPECTS OF THE DISCLOSURE

Figure 3:
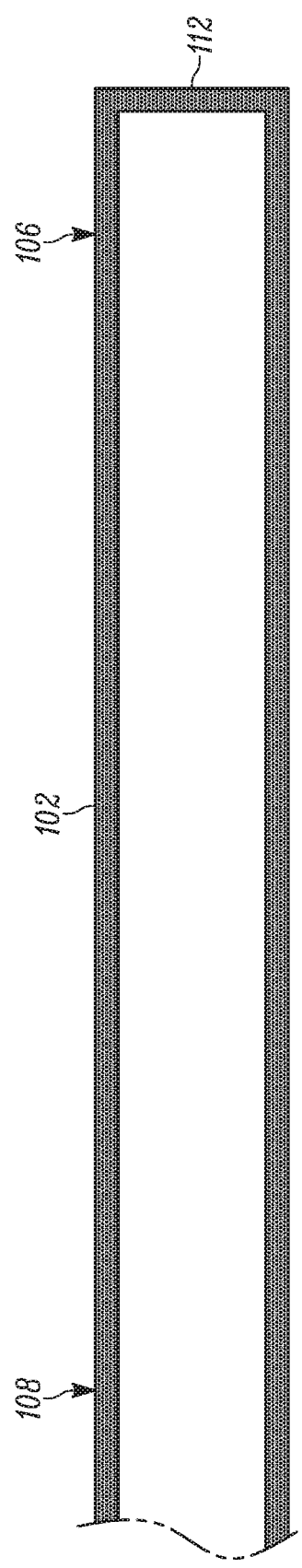
FIG. 3 is a schematic side view of the aspect of FIG. 1, including a second option for a component.

Unless defined otherwise, all technical and scientific terms used herein have the same meaning as is commonly understood by one of skill in the art to which the present disclosure pertains.

As used herein, the term "patient" may refer to any warm-blooded organism including, but not limited to, human beings, pigs, rats, mice, dogs, goats, sheep, horses, monkeys, apes, rabbits, cattle, farm animals, livestock, birds, etc.

As used herein, the term "user" may be used interchangeably to refer to an individual who prepares for, assists, and/or performs a procedure.

As used herein, the singular forms "a," "an" and "the" may include the plural forms as well, unless the context clearly indicates otherwise. It will be further understood that the terms "comprises" and/or "comprising," as used herein, may specify the presence of stated features, steps, operations, elements, and/or components, but do not preclude the presence or addition of one or more other features, steps, operations, elements, components, and/or groups thereof.

As used herein, the term "and/or" may include any and all combinations of one or more of the associated listed items.

As used herein, phrases such as "between X and Y" may be interpreted to include X and Y.

It will be understood that when an element is referred to as being "on," etc., another element, it may be directly on, attached to or contacting the other element or intervening elements may also be present. It will also be appreciated by those of skill in the art that references to a structure or feature that is disposed "adjacent" another feature may not have portions that overlap or underlie the adjacent feature.

Spatially relative terms, such as "over" and the like, may be used herein for ease of description to describe one element or feature's relationship to another element(s) or feature(s) as illustrated in the Figures. It will be understood that the spatially relative terms may encompass different orientations of a device in use or operation, in addition to the orientation depicted in the Figures. For example, if a device in the Figures is inverted, elements described as being "over" other elements or features would then be oriented "under" the other elements or features.

It will be understood that, although the terms "first," "second," etc. may be used herein to describe various elements, these elements should not be limited by these terms. These terms are only used to distinguish one element from another. Thus, a "first" element discussed below could also be termed a "second" element without departing from the teachings of the present disclosure. The sequence of operations (or steps) is not limited to the order presented in the claims or Figures unless specifically indicated otherwise.

The invention comprises, consists of, or consists essentially of the following features, in any combination.

An implant delivery system 100 is provided. The implant delivery system may include an outer sheath 102 having one of any number of alternate configurations, some of which will be discussed below. As shown in FIG. 1, the outer sheath 102 has an outer sheath proximal end 104, an outer sheath distal end 106, and an outer sheath body 108 longitudinally extending between the outer sheath proximal and distal ends 104, 106. The term "longitudinal" is used herein to indicate a substantially horizontal direction, in the orientation of FIG. 1. The outer sheath proximal end 104 may have an outer sheath proximal opening 110. The outer sheath distal end 106 may have an outer sheath open tip 112. The outer sheath 102 may have an outer sheath outer surface 114 and an outer sheath lumen 116. The outer sheath lumen 116 may longitudinally extend between the outer sheath proximal opening 110 and the outer sheath open tip 112. The outer sheath lumen 116 is at least partially configured for selectively holding at least one expandable implant M therein, as will be described later. The expandable implant M may be a stent, a stent-graft, an embolization coil, an embolization plug, a shunt closure device, a cardiovascular valve, a percutaneous valve, any self-expandable device, any other expandable device, or any combination thereof.

As shown in FIG. 2, at least a portion of the outer sheath distal end 106 may be inwardly tapered. The term "taper" is defined herein as a gradual diminution of thickness, diameter, or width in an elongated object, as is shown by the gradual diminution in diameter of the outer sheath distal end 106 in FIG. 2. The term "inward" is defined herein as a taper that becomes gradually smaller, such as shown as the gradual diminution in diameter between the outer sheath body 108 and the outer sheath open tip 112 in FIG. 2. Further, the inward taper, such as the taper of the outer sheath distal end 106, could include no expansion in diameter (or even an outward taper) distal to the outer sheath body 108. At least one of the inwardly tapered outer sheath distal end 106 and the outer sheath open tip 112 may be elastically expandable to allow the passage of at least one of an expandable implant M and a shaft 1030, as will be described later, therethrough. As shown in FIG. 3, the outer sheath distal end 106 might not be inwardly tapered. Thus, the outer sheath distal end 106 and the outer sheath body 108 may be substantially level. The term "level" is defined herein as being substantially even or unvarying in diameter, as is shown by the outer sheath distal end 106 not having a gradual or stepwise diminution and/or increase in diameter in FIG. 3.

As shown in FIGS. 4-7, at least one of the outer sheath body 108 and the outer sheath distal end 106 may have at least one outer sheath side wall opening 418 (shown here as outer sheath side wall openings 418a, 418b, and 418c) and at least one outer sheath open slit 420 (shown here as outer sheath open slits 420a, 420b, and 420c). The at least one outer sheath side wall opening 418a, 418b, and 418c selectively places the outer sheath outer surface 114 in fluid communication with the outer sheath lumen 116. The at least one outer sheath open slit 420a, 420b, and 420c may extend at least partially between the outer sheath open tip 112 and a respective outer sheath side wall opening 418a, 418b, and 418c. Each outer sheath open slit 420a, 420b, and 420c has an outer sheath open slit first surface 422 (shown here as outer sheath open slit first surfaces 422a, 422b, and 422c) and an outer sheath open slit second surface 424 (shown here as outer sheath open slit second surfaces 424a, 424b, and 424c). The outer sheath open slit first surface 422a, 422b, 422c oppositely faces and circumferentially abuts the outer sheath open slit second surface 424a, 424b, 424c. The term "circumferentially" is defined herein as at least partially surrounding the external boundary or surface of a figure or object. The outer sheath open slit first surface 422a, 422b, 422c and the outer sheath open slit second surface 424a, 424b, 424c may be selectively elastically separable. That is, a force may be applied to separate the outer sheath open slit first surface 422a, 422b, 422c and the outer sheath open slit second surface 424a, 424b, 424c, as that the outer sheath open slit first surface 422a, 422b, 422c will no longer be abutting the outer sheath open slit second surface 424a, 424b, 424c. However, upon the removal of the separating force, the outer sheath open slit first surface 422a, 422b, 422c and the outer sheath open slit second surface 424a, 424b, 424c will return to their original abutting position due to the elastic nature of the material forming the outer sheath open slit first surface 422a, 422b, 422c and the outer sheath open slit second surface 424a, 424b, 424c. Alternatively, instead of abutting, the outer sheath open slit first surface 422a, 422b, 422c and the outer sheath open slit second surface 424a, 424b, 424c may radially overlap to provide a labyrinth-type seal (not shown). The term "radial" is used herein to indicate a direction substantially perpendicular to the "longitudinal" direction, and is shown via arrows "R" in FIG. 4a extending toward a central longitudinal axis LA, in the orientation of FIG. 4a.

Instead of abutting and/or overlapping, at least a portion of the outer sheath open slit first surface 422a, 422b, 422c may be radially spaced from at least a portion of the outer sheath open slit second surface 424a, 424b, 424c. The space between the outer sheath open slit first surface 422a, 422b, 422c and the outer sheath open slit second surface 424a, 424b, 424c may be configured to allow the passage of at least a portion of a guidewire 1856 therethrough. When the outer sheath open slit 420a, 420b, 420c has radially spaced outer sheath open slit first and second surfaces 422a, 422b, 422c, 424a, 424b, 424c, the outer sheath open slit first surface 422a, 422b, 422c and the outer sheath open slit second surface 424a, 424b, 424c may be selectively elastically separable. That is, a force may be applied to separate at least a portion of the outer sheath open slit first surface 422a, 422b, 422c even further apart from at least a portion of the outer sheath open slit second surface 424a, 424b, 424c, as that the radial spacing between at least a portion of the outer sheath open slit first and second surfaces 422a, 422b, 422c, 424a, 424b, 424c is larger post-separating forcing than what the radial spacing was pre-separating force. However, upon the removal of the separating force, the outer sheath open slit first surface 422a, 422b, 422c and the outer sheath open slit second surface 424a, 424b, 424c will return to their pre-separating force radial spacing due to the elastic nature of the material forming the outer sheath open slit first surface 422a, 422b, 422c and the outer sheath open slit second surface 424a, 424b, 424c.

Figure 4:
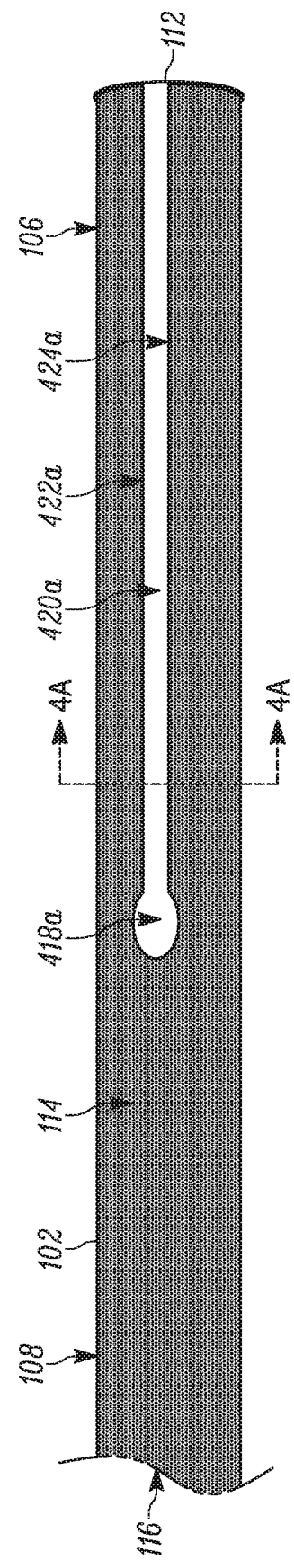
FIG. 4 is a schematic top view of the aspect of FIG. 1, including a first option for a component.
Figure 4A:
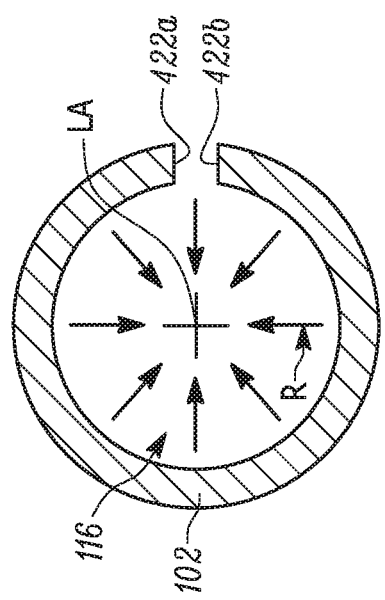
FIG. 4a depicts a cross-sectional view of the aspect of FIG. 4.
Figure 5:
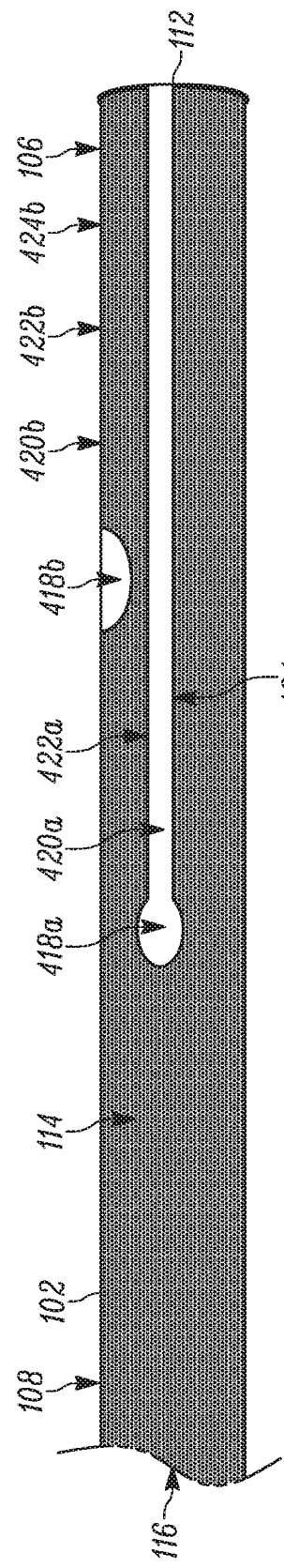
FIG. 5 is a schematic top view of the aspect of FIG. 1, including a second option for a component.

FIG. 4 depicts the outer sheath 102 having one outer sheath side wall opening 418a and one outer sheath open slit 420a that extends at least partially between the outer sheath open tip 112 and the outer sheath side wall opening 418a. FIGS. 5-6 depict the outer sheath 102 having a plurality of outer sheath side wall openings 418a, 418b, 418c and a plurality of outer sheath open slits 420a, 420b, 420c. Each of the outer sheath open slits 420a, 420b, 420c longitudinally extends between the outer sheath open tip 112 and a respective outer sheath side wall opening 418a, 418b, 418c. Each of the outer sheath side wall openings 418a, 418b, 418c and respective outer sheath open slits 420a, 420b, 420c, may be circumferentially offset from the other outer sheath side wall openings 418a, 418b, 418c and respective outer sheath open slits 420a, 420b, 420c on at least one of the outer sheath body 108 and the outer sheath distal end 106.

FIG. 7 depicts the outer sheath 102 having a plurality of outer sheath side wall openings 418a, 418b, 418c arranged in parallel on at least one of the outer sheath body 108 and the outer sheath distal end 106. The outer sheath 102 of FIG. 7 further has an outer sheath open slit 420 longitudinally extending from the outer sheath open tip 112, through at least one outer sheath side wall opening 418a, 418b of the plurality of outer sheath side wall openings 418a, 418b, 418c, and to another of the outer sheath side wall openings 418c. The at least one of the plurality of side wall openings 418a, 418b, 418c through which the outer sheath open slit 420 extends may form a portion of the outer sheath open slit 420. For example, as shown in FIG. 7, the outer sheath open slit 420 longitudinally extends from the outer sheath open tip 112, through first and second outer sheath side wall openings 418a, 418b, and to a third outer sheath side wall opening 418c. In such case, the first and second outer sheath side wall openings 418a, 418b may form a portion of the outer sheath open slit 420, and accordingly may form at least a portion of the outer sheath open slit first and second surfaces 422, 424.

As shown in FIG. 8, the outer sheath 102 may have at least one c-clip 826 (shown here as c-clips 826a, 826b, and 826c) or other circumferentially extending reinforcing structure embedded in the outer sheath 102 radially between the outer sheath outer surface 114 and the outer sheath lumen 116 and radially adjacent to a respective outer sheath open slit 420a, 420b, 420c. Instead of, or in addition to, the at least one c-clip 826a, 826b, and 826c being embedded in the outer sheath 102, the at least one c-clip 826a, 826b, and 826c may be selectively disposed on a portion of the outer sheath outer surface 114 that is adjacent to a respective outer sheath open slit 420a, 420b, 420c. Alternatively, or in addition to the above, the at least one c-clip 826a, 826b, and 826c may be selectively disposed within (e.g., via overmolding) at least a portion of the outer sheath lumen 116 that is adjacent to a respective outer sheath open slit 420a, 420b, 420c.

Figure 8B:
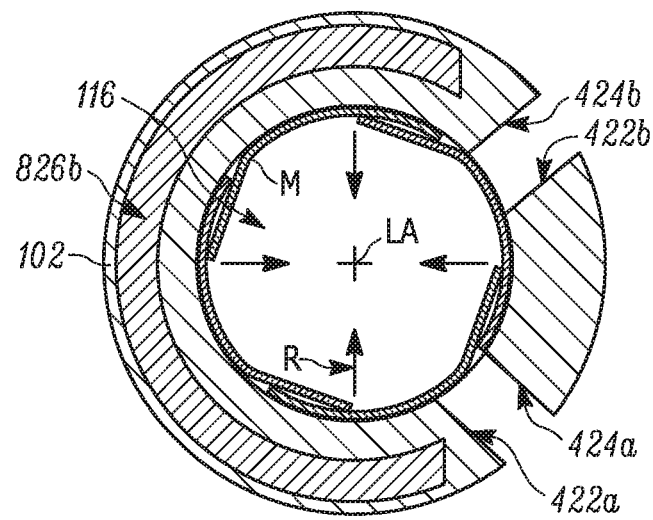
Figure 8C:
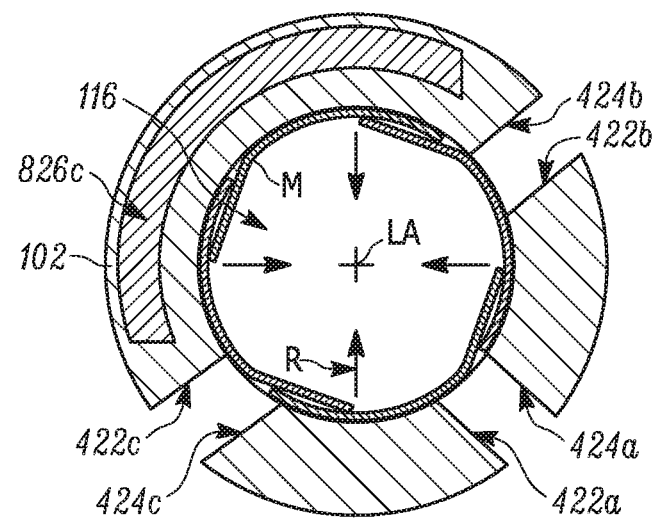

The c-clip 826a, 826b, and 826c at least partially selectively restricts the outer sheath open slit first surface 422a, 422b, 422c from elastically separating from the outer sheath open slit second surface 424a, 424b, 424c when an expandable implant M, such as, but not limited to, a self-expanding implant, is disposed within the outer sheath lumen 116. In other words, an expandable implant M placed within the outer sheath lumen 116 in a collapsed condition may tend to want to move toward an expanded condition due to the natural properties of the expandable implant M. For example, the natural properties of the expandable implant M may include shape memory material causing the expandable implant to move from a collapsed condition to an expanded condition, an elastic deformation from a collapsed condition and a biasing back to an expanded condition, and/or any other suitable property of the expandable implant M that may urge a collapsed expandable implant M to move toward an expanded condition. Because the outer sheath open slit first surface 422a, 422b, 422c is elastically separable from the outer sheath open slit second surface 424a, 424b, 424c, the movement of the expandable implant M toward the expanded condition might tend to cause the outer sheath open slit first surface 422a, 422b, 422c to elastically separate from the outer sheath open slit second surface 424a, 424b, 424c in an unwanted manner. However, as shown in FIGS. 8a-c, when the at least one c-clip 826a, 826b, and 826c is embedded in the outer sheath 102, the at least one c-clip 826a, 826b, and 826c provides a radially inward pressure or bias to at least partially selectively restrict/inhibit/prevent the expandable implant M from moving from a collapsed condition toward an expanded condition, and thus at least partially restricts/inhibits/prevents the expandable implant M from elastically separating the outer sheath open slit first surface 422a, 422b, 422c from the outer sheath open slit second surface 424a, 424b, 424c. The at least one c-clip 826a, 826b, and 826c may be at least partially radiopaque, and thus visible under radiography or other intraoperative imaging techniques to assist with imaging-guided placement and/or orientation.

Figure 9B:
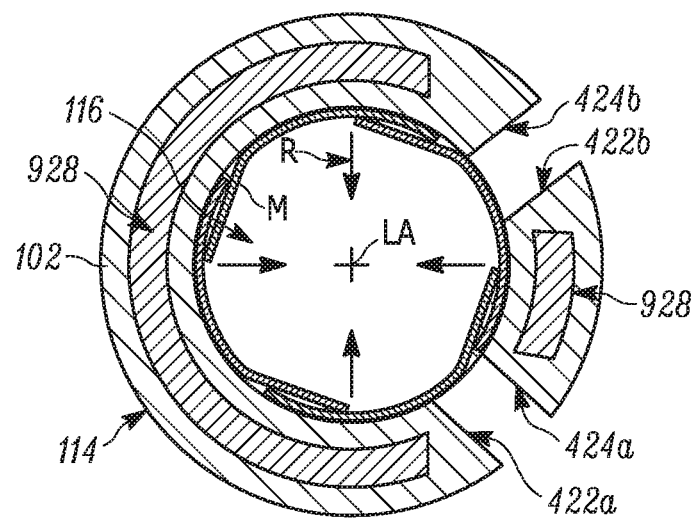
Figure 9C:
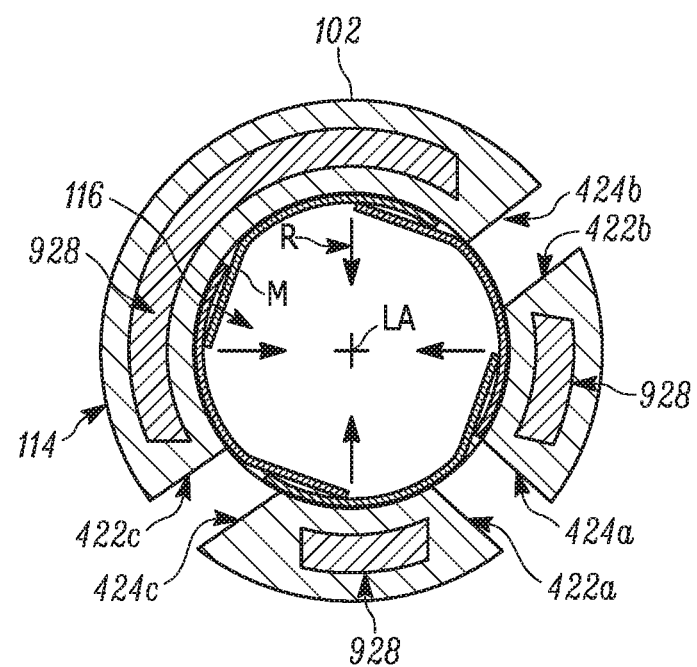

Instead of, or in addition to, the outer sheath 102 having at least one c-clip 826a, 826b, and 826c to at least partially selectively restrict a respective outer sheath open slit first surface 422a, 422b, 422c from elastically separating from a respective outer sheath open slit second surface 424a, 424b, 424c, the outer sheath 102 may have at least one reinforcing element 928 or other circumferentially extending reinforcing structure. As shown in FIGS. 9-9c, the at least one reinforcing element 928 may be radially embedded in the outer sheath 102 between the outer sheath outer surface 114 and the outer sheath lumen 116 and radially adjacent to the at least one outer sheath open slit 420a, 420b, 420c. Instead of, or in addition to, the at least one reinforcing element 928 being embedded in the outer sheath 102, the at least one reinforcing element 928 may be selectively disposed on a portion of the outer sheath outer surface 114 that is adjacent to a respective outer sheath open slit 420a, 420b, 420c. Alternatively, or in addition to the above, the at least one reinforcing element 928 may be selectively disposed within (e.g., via overmolding) at least a portion of the outer sheath lumen 116 that is adjacent to a respective outer sheath open slit 420a, 420b, 420c.

The at least one reinforcing element 928 may at least partially longitudinally extend between at least one outer sheath side wall opening 418a, 418b, 418c and the outer sheath open tip 112 to at least partially reinforce a portion of the outer sheath 102 adjacent to the at least one outer sheath open slit 420a, 420b, 420c by at least partially selectively restricting a respective outer sheath open slit first surface 422a, 422b, 422c from elastically separating from a respective outer sheath open slit second surface 424a, 424b, 424c, in a similar manner as previously described in regard to the at least one c-clip 826a, 826b, and 826c. The at least one reinforcing element 928 may be at least partially radiopaque, and thus visible under radiography or other intraoperative imaging-guided techniques to assist with imaging placement and/or orientation.

Figure 10:
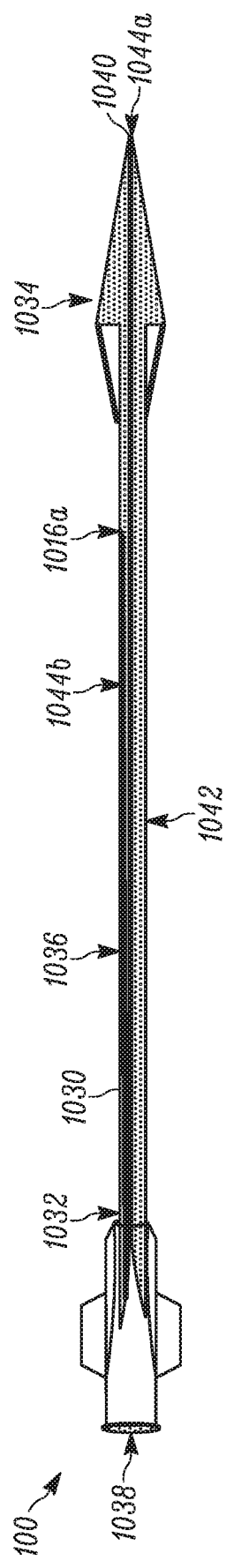
FIG. 10 is a schematic side view of an element of an implant delivery system according to one aspect of the present invention.

The implant delivery system 100 may include a shaft 1030 having one of any number of alternate configurations, some of which will be discussed below. As shown in FIG. 10, the shaft 1030 has a shaft proximal end 1032, a shaft distal end 1034, and a shaft body 1036 longitudinally extending between the shaft proximal and distal ends 1032, 1034. The shaft proximal end 1032 may have at least one shaft proximal opening 1038. The shaft distal end 1034 may have a shaft open tip 1040. The shaft 1030 may have a shaft outer surface 1042 and at least one shaft lumen 1044 (shown here as shaft lumens 1044a and 1044b). At least a portion of the shaft outer surface 1042 may be configured for selectively circumferentially mounting an expandable implant M thereon, as will be described below. The shaft 1030 may have at least one shaft side wall opening 1046 selectively placing the shaft outer surface 1042 in fluid communication with the at least one shaft lumen 1044b.

Figure 11:
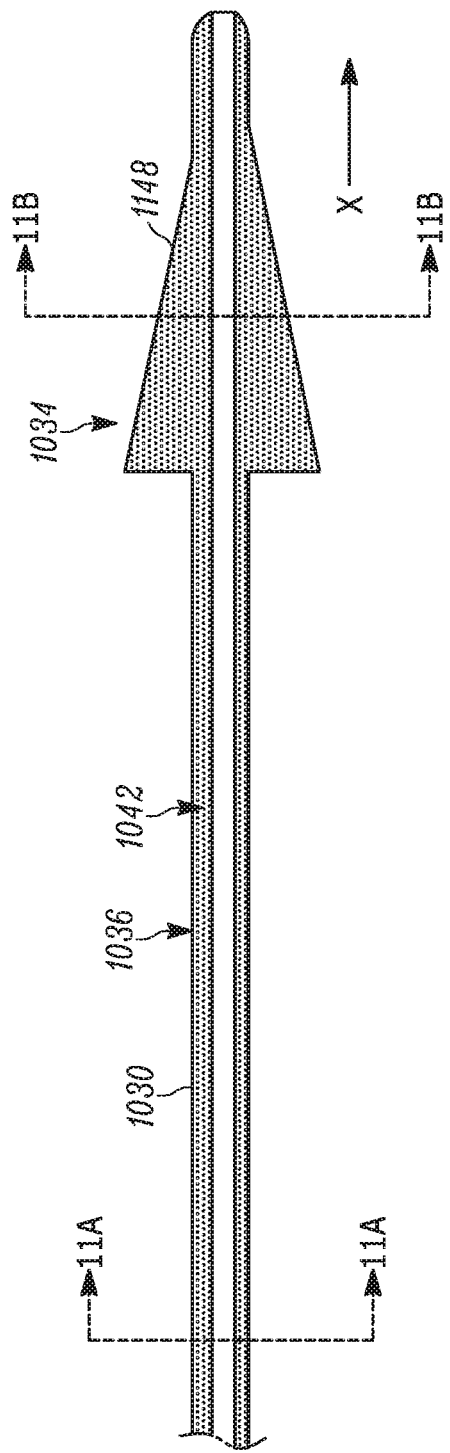
FIG. 11 is a schematic side view of the aspect of FIG. 10, including a first option for a component.
Figure 11A:
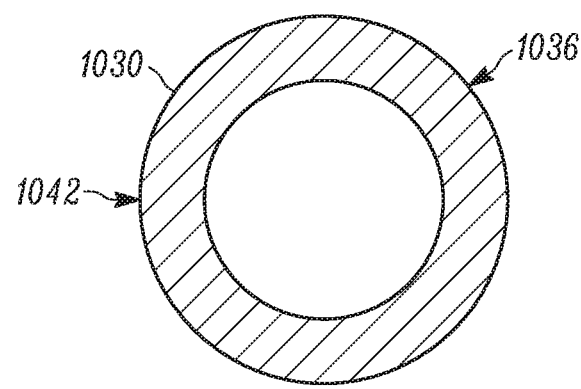
FIGS. 11a-b depict cross-sectional views of the aspect of FIG. 11.
Figure 11B:
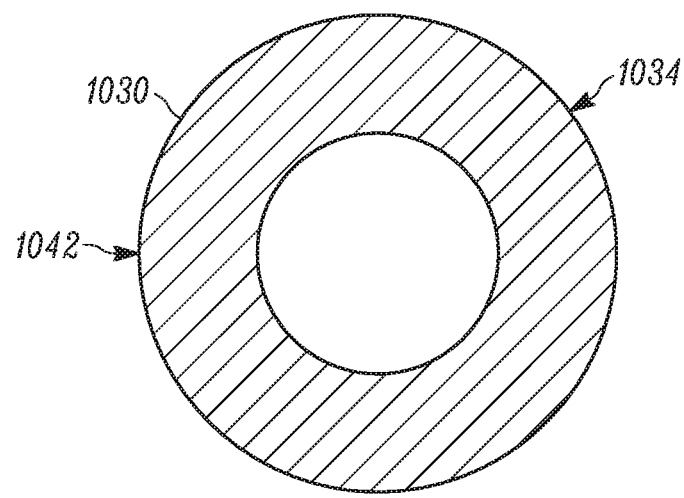

As shown in FIG. 11, the shaft distal end 1034 may have a nosecone 1148. A "nosecone," as used herein, is a structure resembling a cone, or, in other words, resembling a solid bounded by a circular or other closed plane base and the surface formed by line segments joining every point of the boundary of the base to a common vertex. The nosecone 1148 may point, or narrow, in the longitudinally distal direction (shown as an arrow "X" in FIG. 11). The nosecone 1148 may be configured to substantially prevent the egress of an expandable implant M mounted circumferentially on the shaft outer surface 1042 from a desired position on the shaft outer surface 1042. The nosecone 1148 may also or instead, be used for a smooth atraumatic transition of the implant delivery system 100 into a target patient tissue site T. FIGS. 11a-b depict cross-sectional views of various points along the shaft 1030 having the nosecone 1148, to show the structural features of the shaft 1030 having the nosecone 1148 in FIG. 11.

Figure 12:
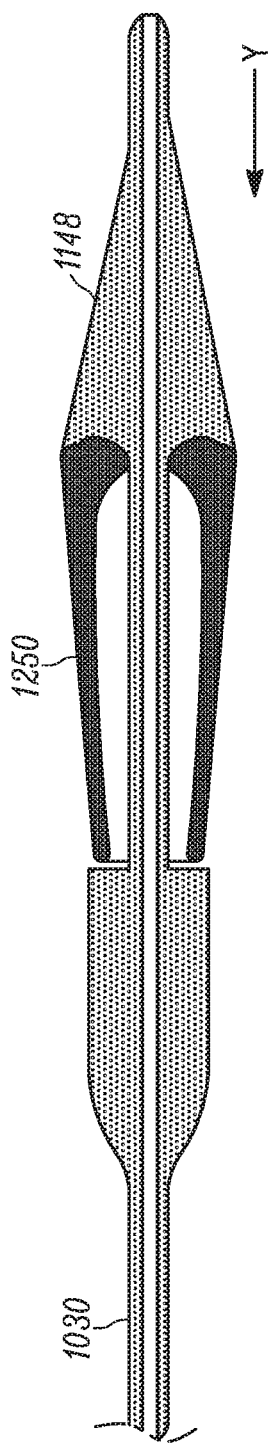
FIGS. 12-13 depict a schematic side view of the aspect of FIG. 10, including a second option for a component, in an example sequence of operation.
Figure 13:
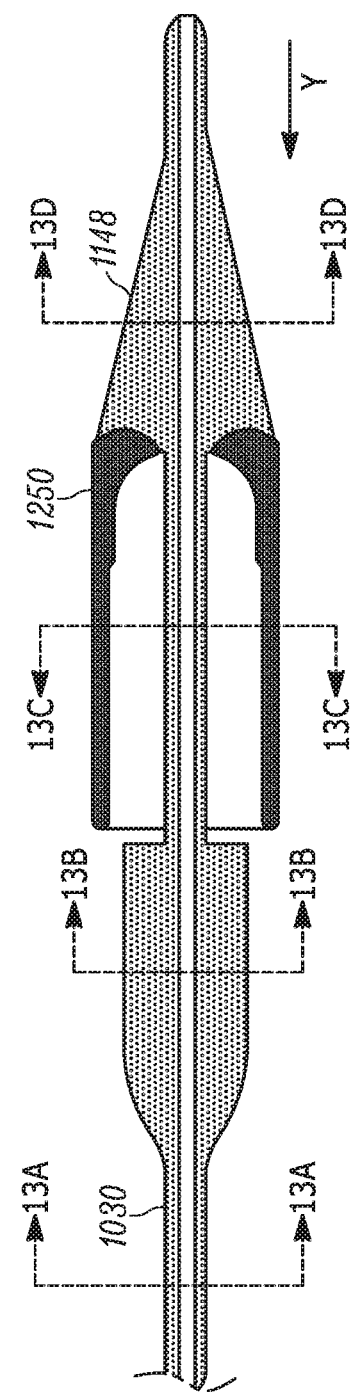
Figure 13A:
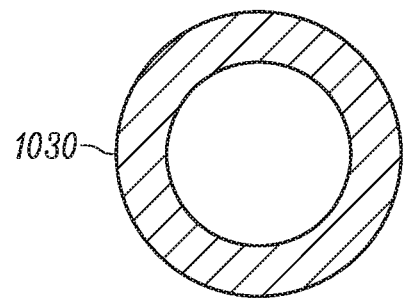
Figure 13B:
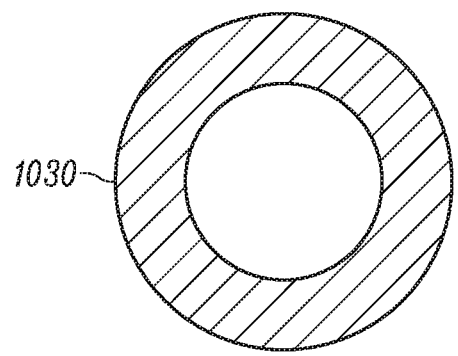
Figure 13C:
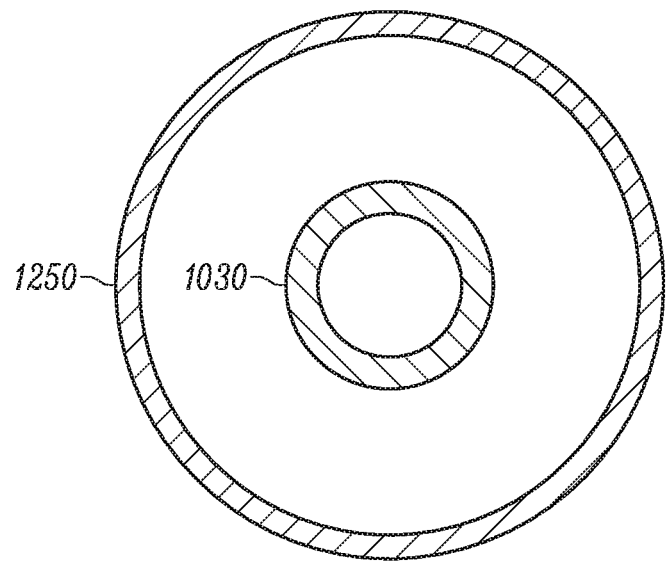

As shown in FIGS. 12-13 the nosecone 1148 may have at least one elastic skirt 1250 that longitudinally extends in the proximal direction (shown as an arrow "Y" in FIG. 12). The elastic skirt 1250 is for selectively restricting an outer sheath open slit first surface 422 from elastically separating from a respective outer sheath open slit second surface 424 when the shaft 1030 is operably joined to the outer sheath 102, as will be described in more detail below. The elastic skirt 1250 is capable of moving between a collapsed condition (FIG. 12) and an expanded condition (FIG. 13). FIGS. 13a-d depict cross-sectional views of various points along the shaft 1030 having the elastic skirt 1250 in the expanded condition, to show the structural features of the shaft 1030 having the elastic skirt 1250 in the expanded condition in FIG. 13.

Figure 14A:
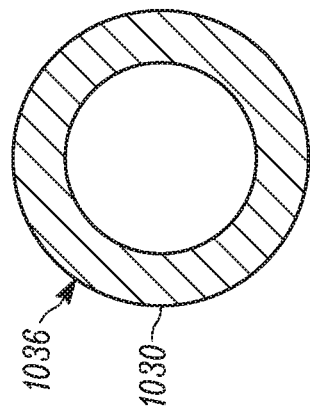
FIG. 14a depicts a cross-sectional view of the aspect of FIG. 14.

As shown in FIG. 14, the shaft distal end 1034 might not have a nosecone 1250. In such case, the shaft distal end 1034 and the shaft body 1036 may be substantially level. FIG. 14a depicts a cross-sectional view of a point along the shaft 1030 having a shaft distal end 1034 and a shaft body 1036 that are substantially level, to show the structural features of the shaft 1030 having a shaft distal end 1034 and a shaft body 1036 that are substantially level in FIG. 14.

Figure 15:
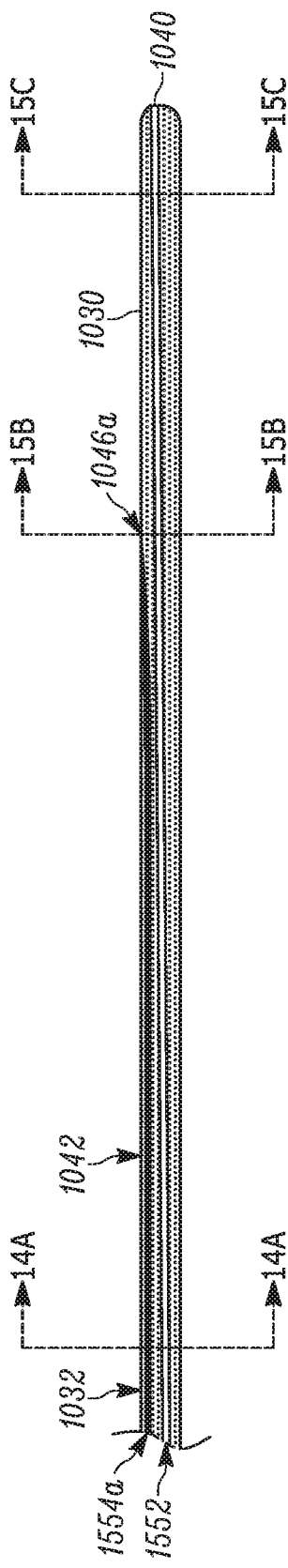
FIG. 15 is a schematic side view of the aspect of FIG. 10, including a second option for a component.
Figure 15A:
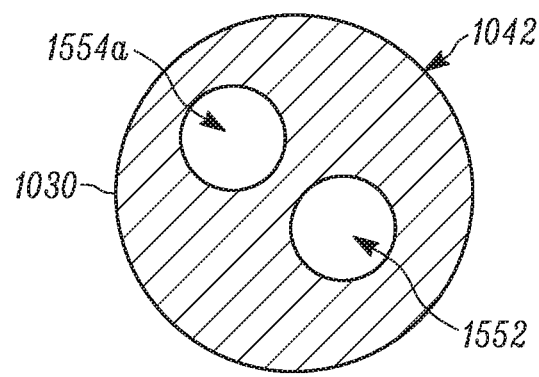
FIGS. 15a-c depict cross-sectional views of the aspect of FIG. 15.
Figure 15B:
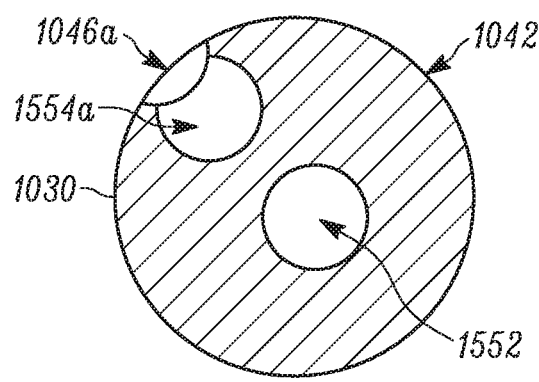
Figure 15C:
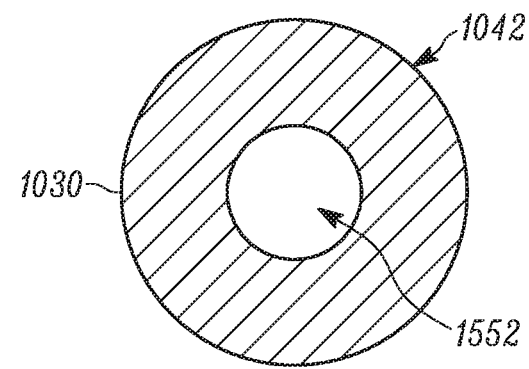
Figure 16B:
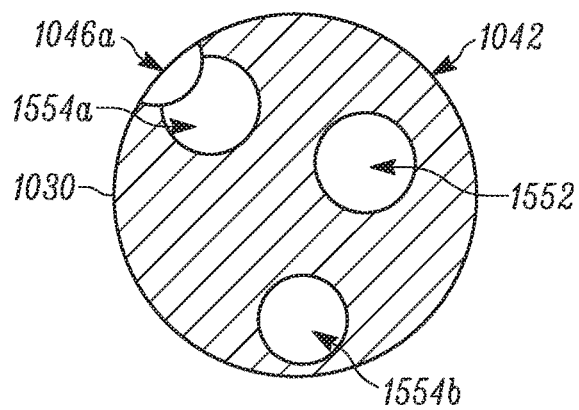
Figure 16C:
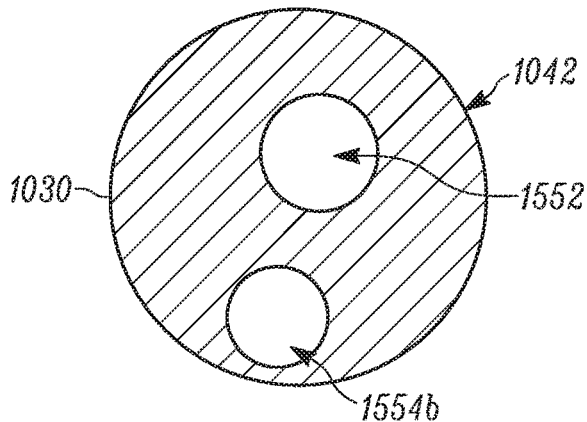
Figure 16D:
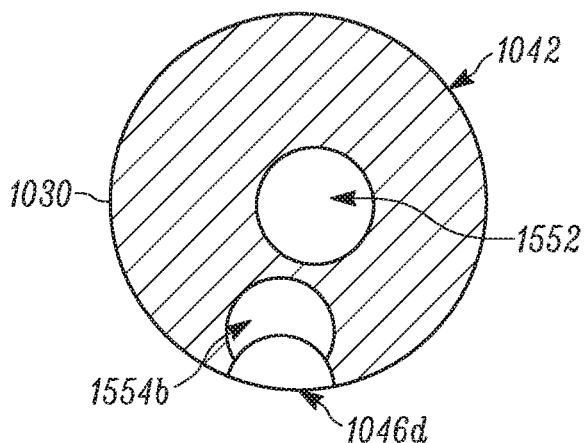
Figure 16E:
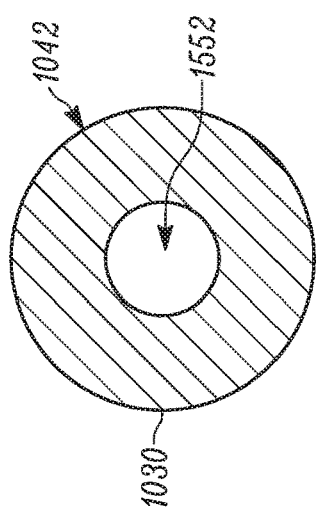
Figure 17:
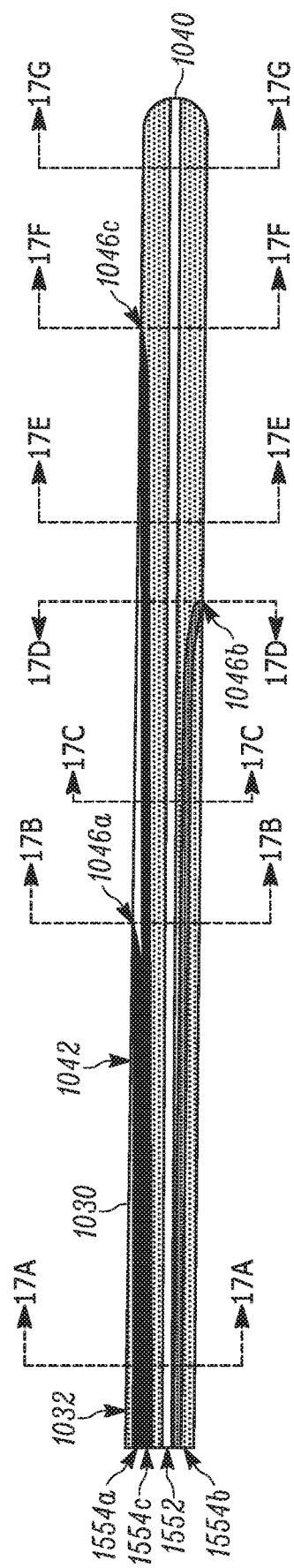
FIG. 17 is a schematic side view of the aspect of FIG. 10, including a fourth option for a component.
Figure 17A:
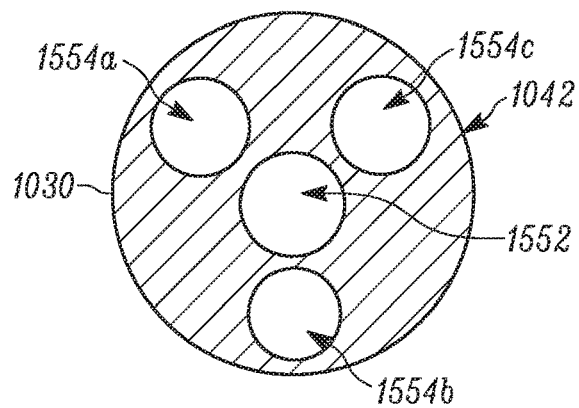
FIGS. 17a-g depict cross-sectional views of the aspect of FIG. 17.
Figure 17B:
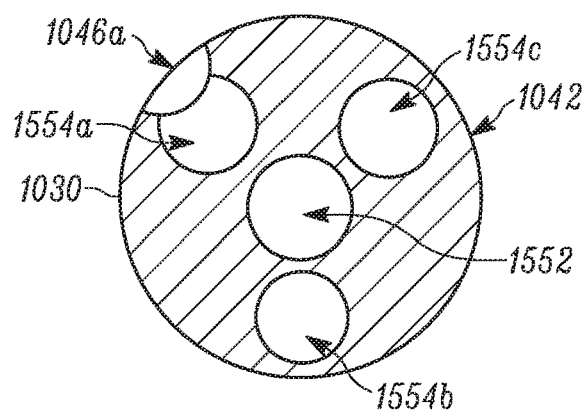
Figure 17C:
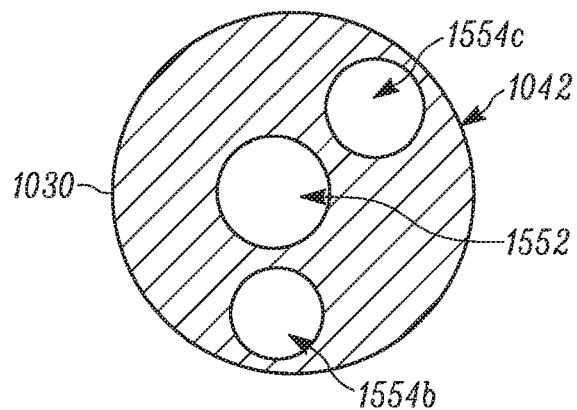
Figure 17D:
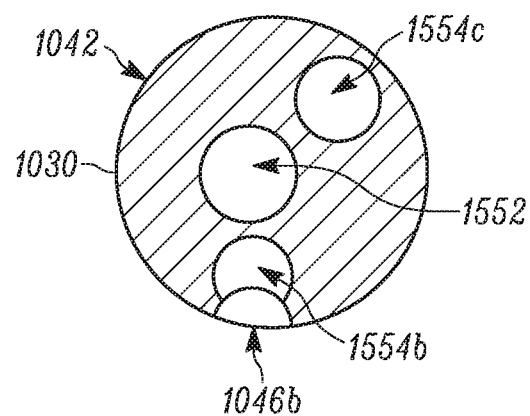
Figure 17E:
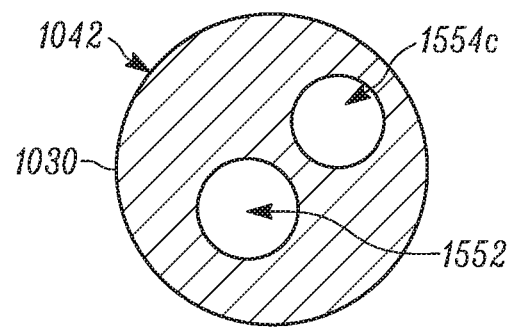
Figure 17F:
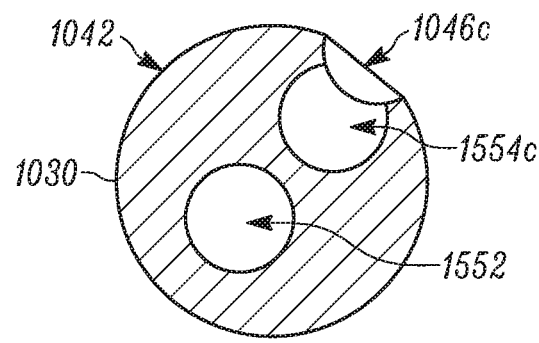
Figure 17G:
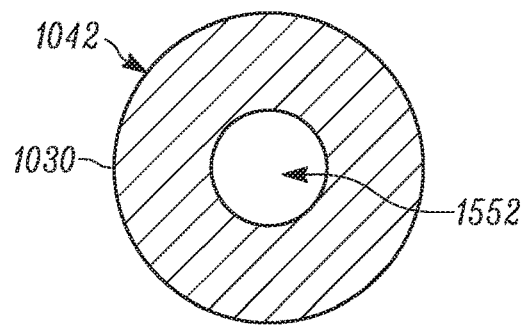

As shown in FIGS. 15-17, the shaft 1030 may have a shaft first lumen 1552 and at least one shaft second lumen 1554 (shown here as shaft second lumens 1554a, 1554b, and 1554c). The shaft first lumen 1552 may longitudinally extend between the shaft open tip 1040 and at least one of the shaft proximal end 1032 and the at least one shaft proximal opening 1038. The at least one shaft second lumen 1554a, 1554b, and 1554c may longitudinally extend between a respective shaft side wall opening 1046 (shown here as shaft side wall openings 1046a, 1046b, and 1046c) and at least one of the shaft proximal end 1032 and the at least one of the shaft proximal opening 1038. The shaft first and second lumens 1552, 1554a, 1554b, 1554c may share a common shaft proximal opening 1038, and/or may each have a respective proximal opening 1038. The shaft side wall opening 1046a, 1046b, 1046c may selectively place the shaft outer surface 1042 in fluid communication with a respective shaft second lumen 1554a, 1554b, 1554c. For example, FIG. 15 depicts a shaft 1030 having the shaft first lumen 1552 and one shaft second lumen 1554a that extends between at least one of the shaft proximal end 1032 and the shaft proximal opening 1038 and a respective shaft side wall opening 1046a. FIGS. 15a-c depict cross-sectional views of various points along the shaft 1030 having the shaft first lumen 1552 and the shaft second lumen 1554a, to show the structural features of the shaft 1030 having the shaft first lumen 1552 and the shaft second lumen 1554a in FIG. 15.

Figure 18:
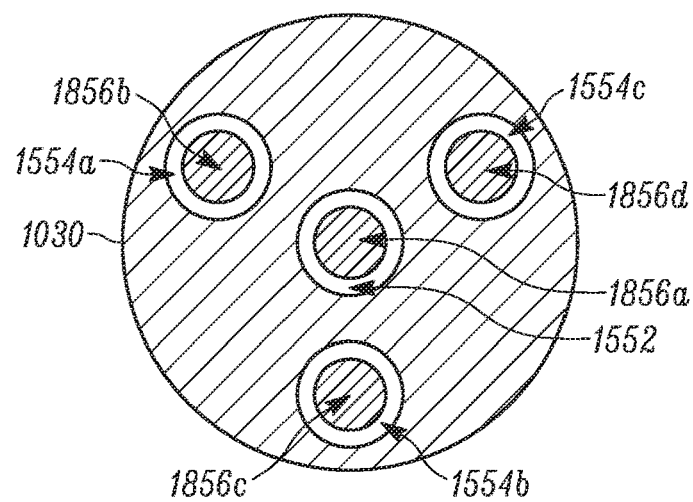
FIG. 18 depicts a cross-sectional view of the aspect of FIG. 10, including a first option for a component.
Figure 19:
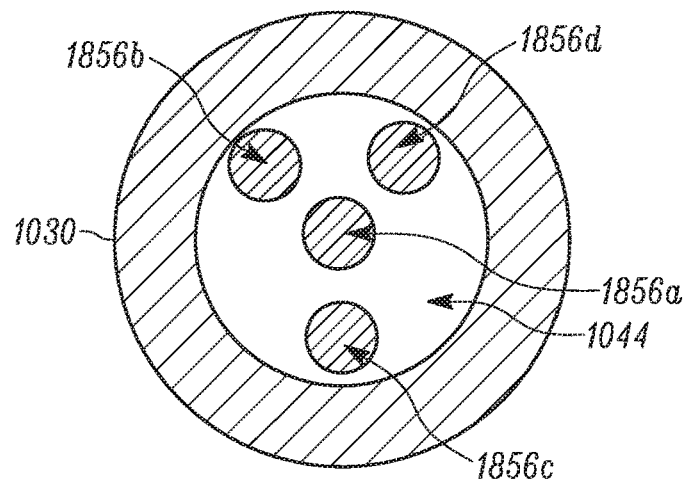
FIG. 19 depicts a cross-sectional view of the aspect of FIG. 10, including a second option for a component.

FIGS. 16-17 depict the shaft 1030 having the shaft first lumen 1552 and a plurality of shaft second lumens 1554a, 1554b, 1554c. Each of the shaft second lumens 1554a, 1554b, 1554c longitudinally extends between a respective shaft side wall opening 1046a, 1046b, 1046c and at least one of the shaft proximal end 1032, a common shaft proximal opening 1038, and a respective shaft proximal opening 1038. Each of the shaft side wall openings 1046a, 1046b, 1046c selectively places the shaft outer surface 1042 in fluid communication with a respective shaft second lumen 1554a, 1554b, 1554c. FIGS. 16a-e depict cross-sectional views of various points along the shaft 1030 having the shaft first lumen 1552 and a plurality of shaft second lumens 1554a, 1554b, to show the structural features of the shaft 1030 having the shaft first lumen 1552 and a plurality of shaft second lumens 1554a, 1554b in FIG. 16. FIGS. 17a-g depict cross-sectional views of various points along the shaft 1030 having the shaft first lumen 1552 and a plurality of shaft second lumens 1554a, 1554b, 1554c, to show the structural features of the shaft 1030 having the shaft first lumen 1552 and a plurality of shaft second lumens 1554a, 1554b, 1554c in FIG. 17. Instead of the shaft 1030 having a shaft first lumen 1552 and at least one shaft second lumen 1554a, 1554b, 1554c for allowing the passage of at least one guidewire 1856 (shown here as guidewires 1856a, 1856b, 1856c, and 1856d), as shown in FIG. 18, the shaft 1030 may have one shaft lumen 1044 that substantially functions as both the shaft first lumen 1552 and the at least one shaft second lumen 1554a, 1554b, 1554c, as shown in FIG. 19. In such case, the shaft 1030 may have at least one shaft side wall opening 1046a, 1046b, 1046c that places the shaft outer surface 1042 in fluid communication with the shaft lumen 1044.

Figure 20:
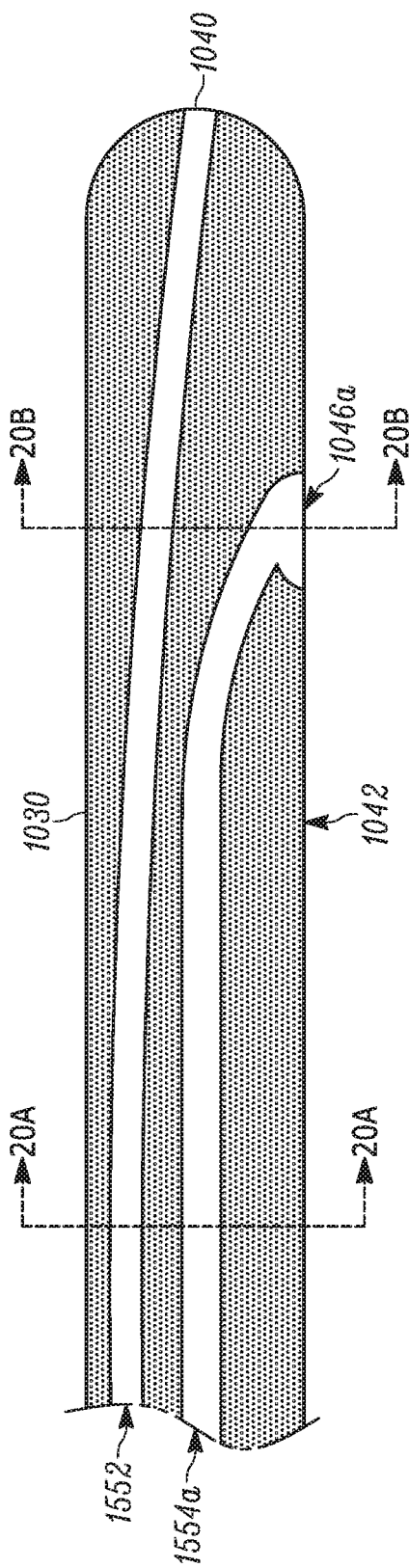
FIG. 20 is a schematic side view of the aspect of FIG. 10, including a first option for a component.
Figure 20A:
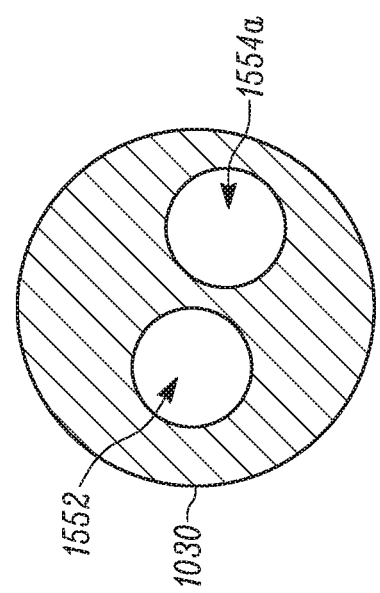
FIGS. 20a-b depict cross-sectional views of the aspect of FIG. 20.
Figure 20B:
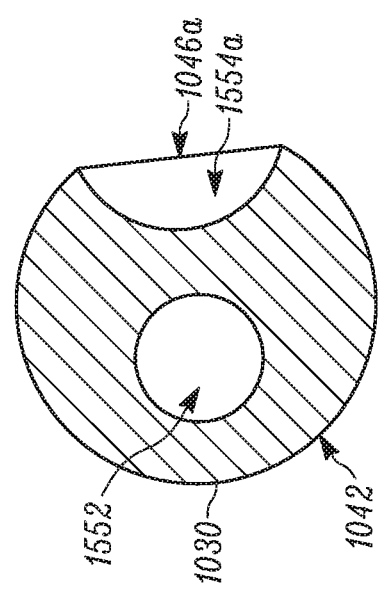

As shown in FIG. 20, at least a portion of shaft outer surface 1042 adjacent to the at least one shaft side wall opening 1046a may be substantially flush with the shaft outer surface 1042 on at least one of the shaft proximal end 1032, the shaft distal end 1034, and the shaft body 1036. The term "flush" is defined herein as being substantially similar in profile, and without significant radial discrepancies. FIGS. 20a-b depict cross-sectional views of various points along the shaft 1030 having at least a portion of the shaft outer surface 1042 adjacent to the at least one shaft side wall opening 1046a being substantially flush, to show the structural features of the shaft 1030 having at least a portion of the shaft outer surface 1042 adjacent to the at least one shaft side wall opening 1046a being substantially level in FIG. 20.

Figure 21:
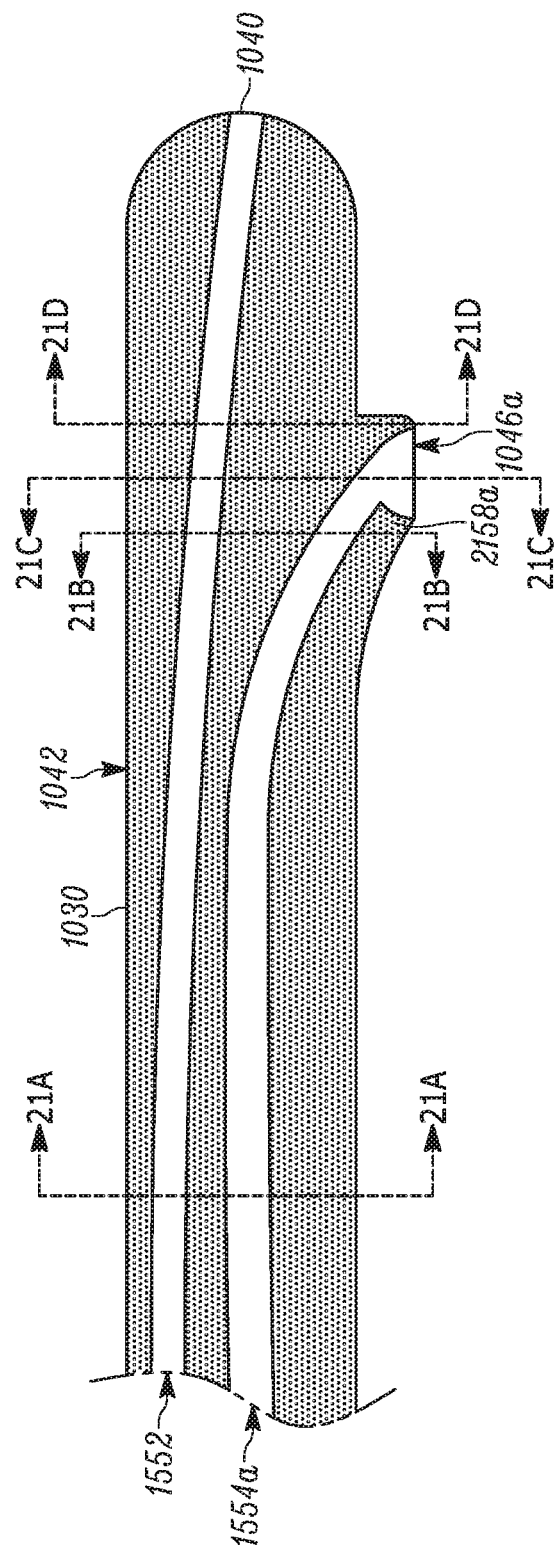
FIG. 21 is a schematic side view of the aspect of FIG. 10, including a second option for a component.
Figure 21A:
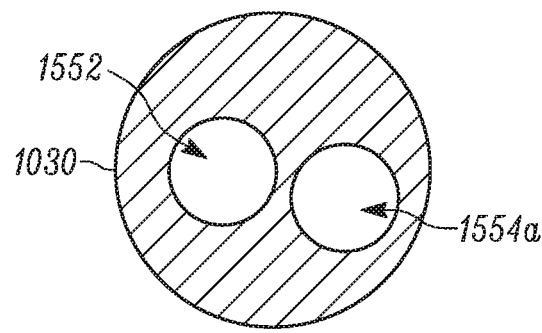
FIGS. 21a-d depict cross-sectional views of the aspect of FIG. 21.
Figure 21B:
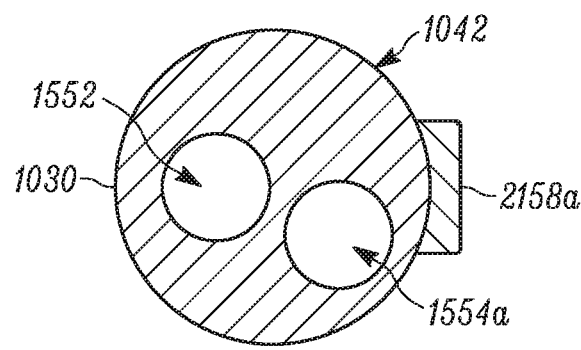
Figure 21C:
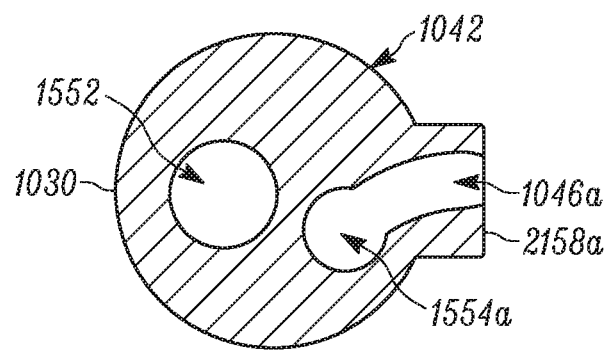
Figure 21D:
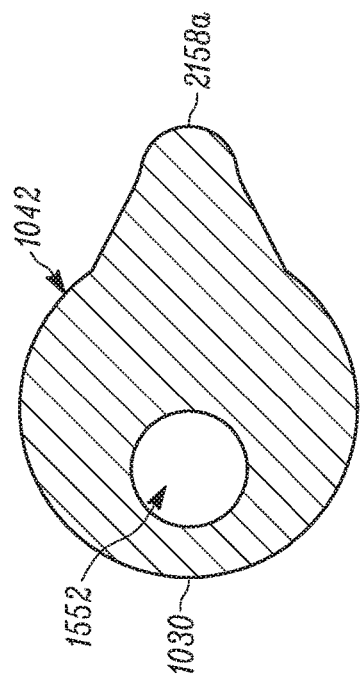
Figure 22:
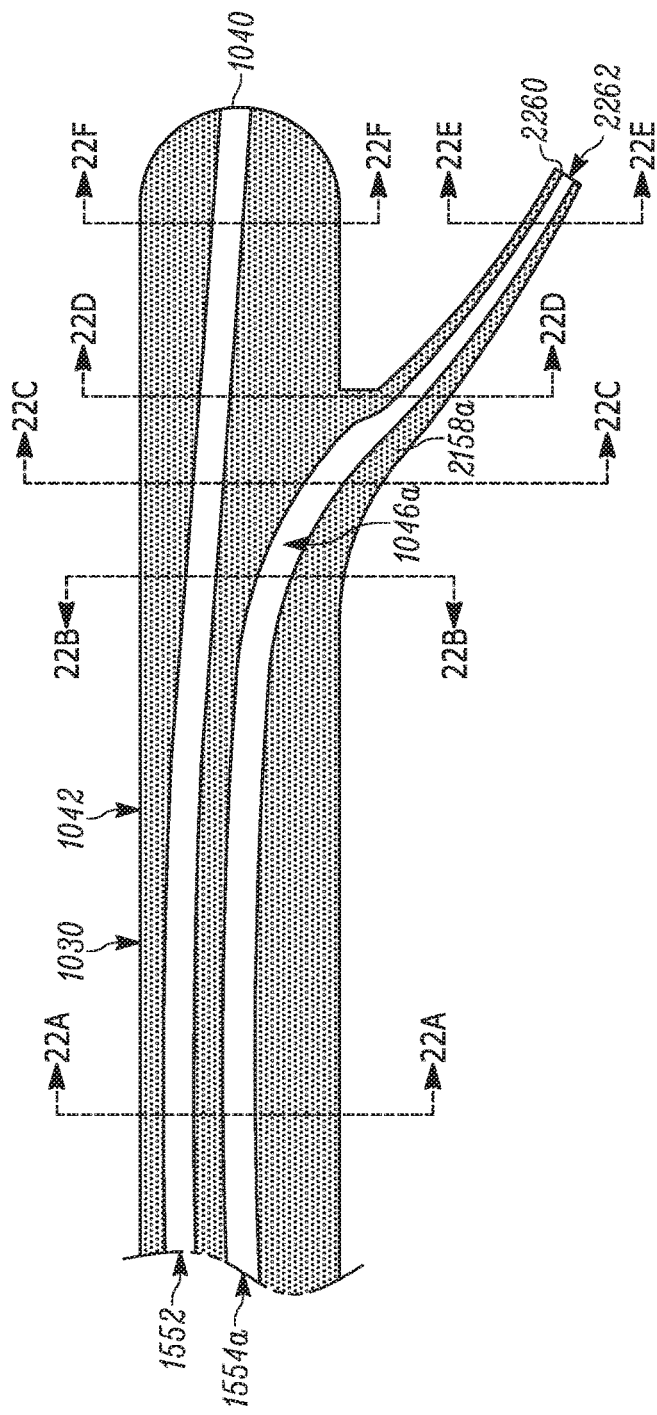
FIG. 22 is a schematic side view of the aspect of FIG. 10, including a third option for a component.
Figure 22A:
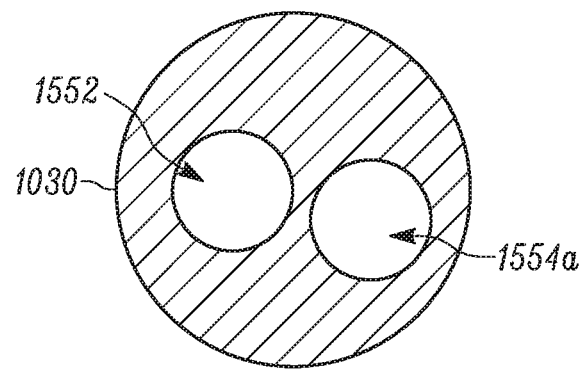
FIGS. 22a-f depict cross-sectional views of the aspect of FIG. 22.
Figure 22B:
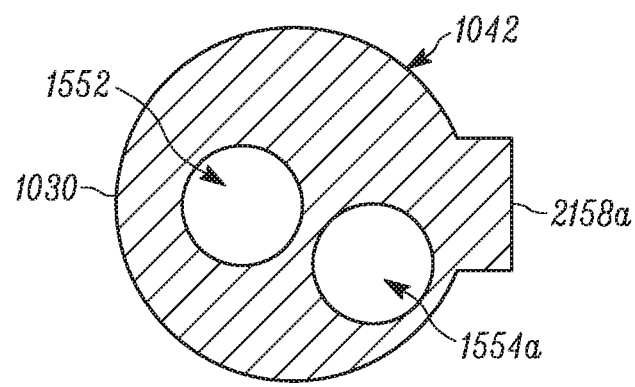
Figure 22C:
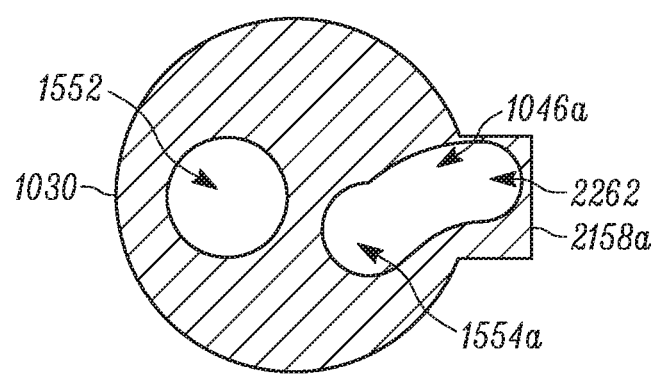
Figure 22D:
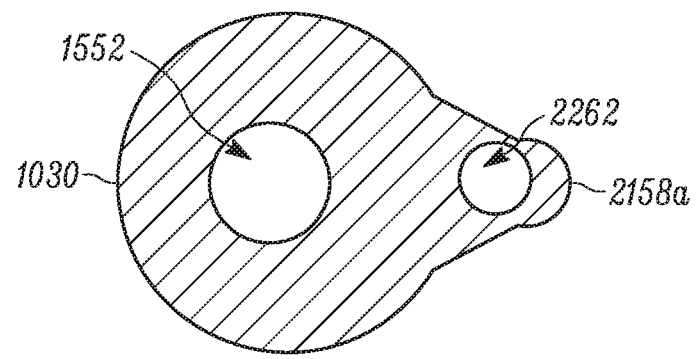
Figure 22E:
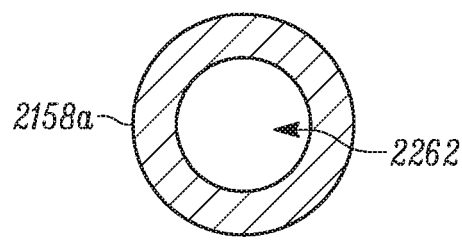
Figure 22F:
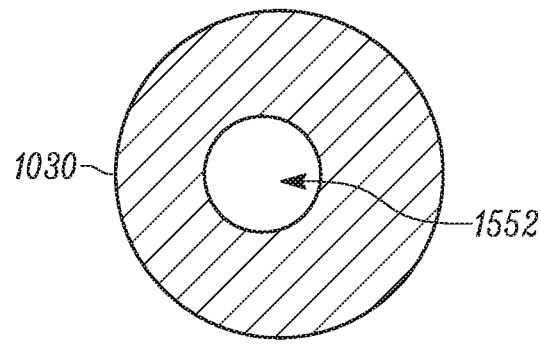

Instead of, or in addition to, at least a portion of shaft outer surface 1042 adjacent to the at least one shaft side wall opening 1046 being substantially flush, the shaft 1030 may have at least one shaft projection 2158 (shown as shaft projections 2158a, 2158b, and 2158c) substantially radially extending from the shaft outer surface 1042 at a respective shaft side wall opening 1046a, 1046b, 1046c, as shown in FIGS. 21-22. In such case, when the shaft 1030 is operably joined to the outer sheath 102, the at least one shaft projection 2158a, 2158b, and 2158c may at least partially extend into, and/or extend through, a respective outer sheath side wall opening 418a, 418b, 418c, as will be described below. The at least one shaft projection 2158a, 2158b, and 2158c may be configured to facilitate the separation of an outer sheath open slit first surface 422 and an outer sheath open slit second surface 424 of a respective outer sheath open slit 420a, 420b, 420c, as will be discussed below.

As shown in FIG. 22, the at least one shaft projection 2158a, 2158b, and 2158c may have a shaft projection open tip 2260 and a shaft projection lumen 2262 that extends from the shaft side wall opening 1046a to the shaft projection open tip 2262. The shaft projection lumen 2262 may selectively place the shaft projection open tip 2260 in fluid communication with the at least one of the shaft lumen 1044, such as the shaft first lumen 1552 and the at least one shaft second lumen 1554a. FIGS. 21a-d depict cross-sectional views of various points along the shaft 1030 having the at least one shaft projection 2158a, to show the structural features of the shaft 1030 having the at least one projection 2158a, as depicted in FIG. 21. FIGS. 22a-f depict cross-sectional views of various points along the shaft 1030 having the at least one projection 2158a, to show the structural features of the shaft 1030 having the at least one shaft projection 2158a, as depicted in FIG. 22.

Figure 23:
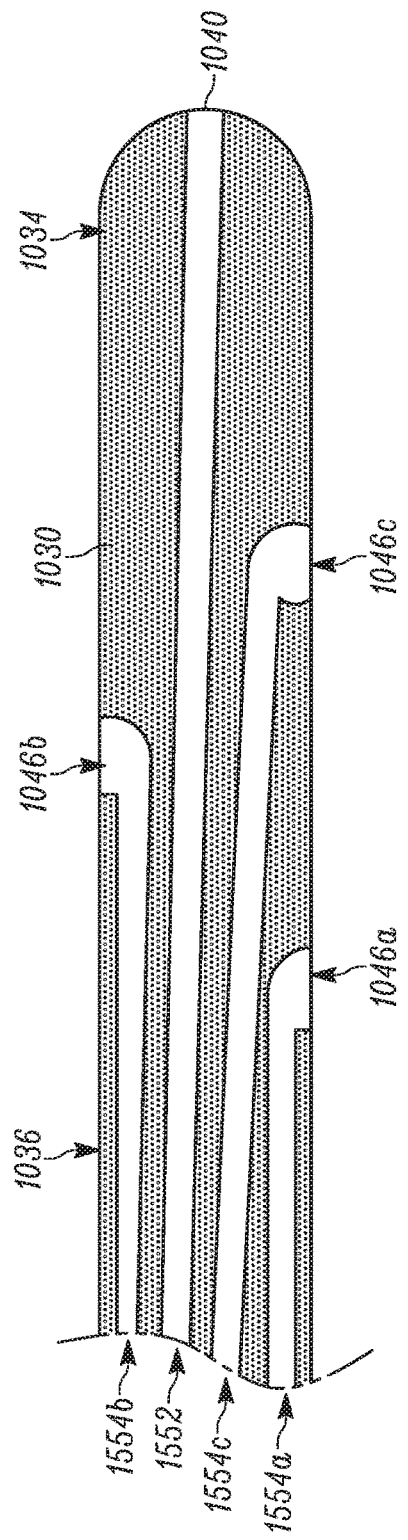
FIG. 23 is a schematic side view of the aspect of FIG. 10, including a first option for a component.
Figure 24:
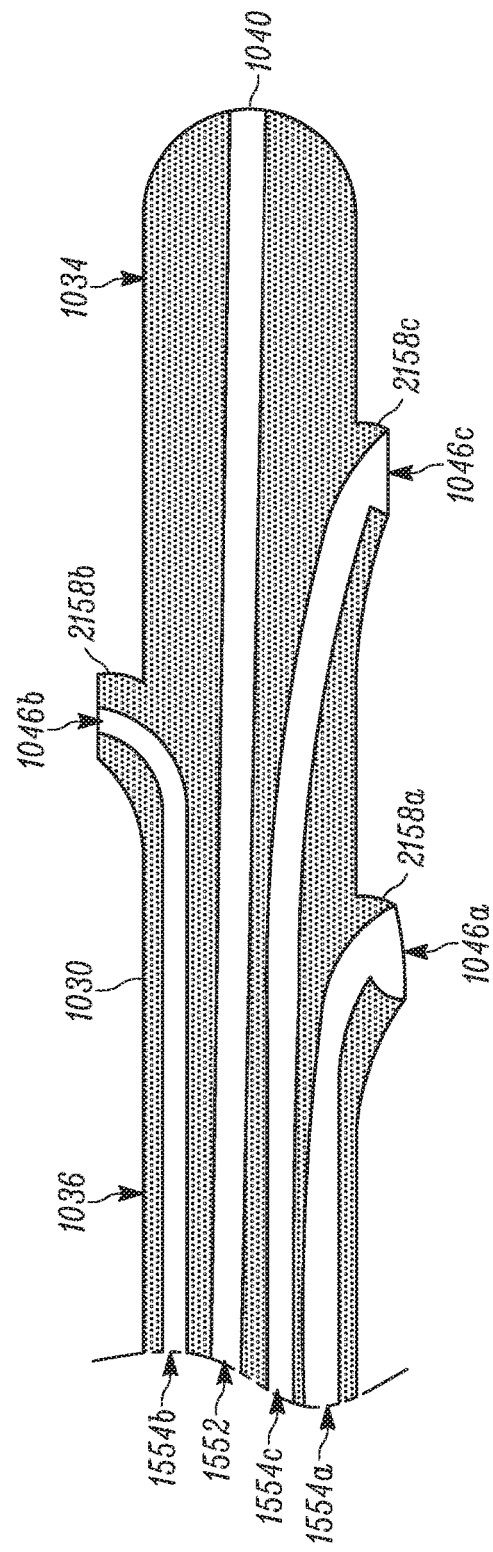
FIG. 24 is a schematic side view of the aspect of FIG. 10, including a second option for a component.
Figure 25:
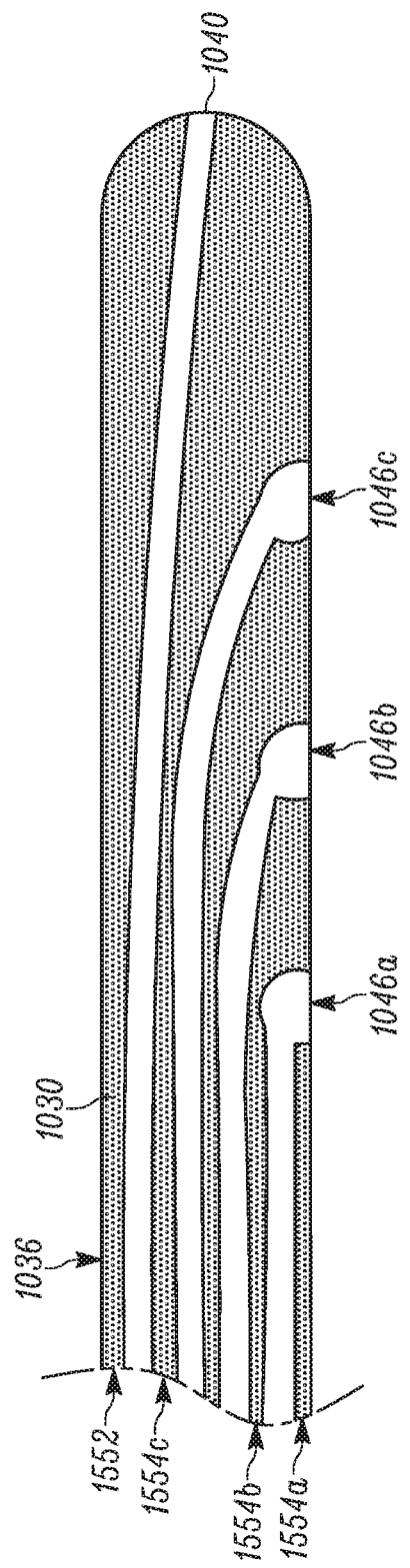
FIG. 25 is a schematic side view of the aspect of FIG. 10, including a third option for a component.
Figure 26:
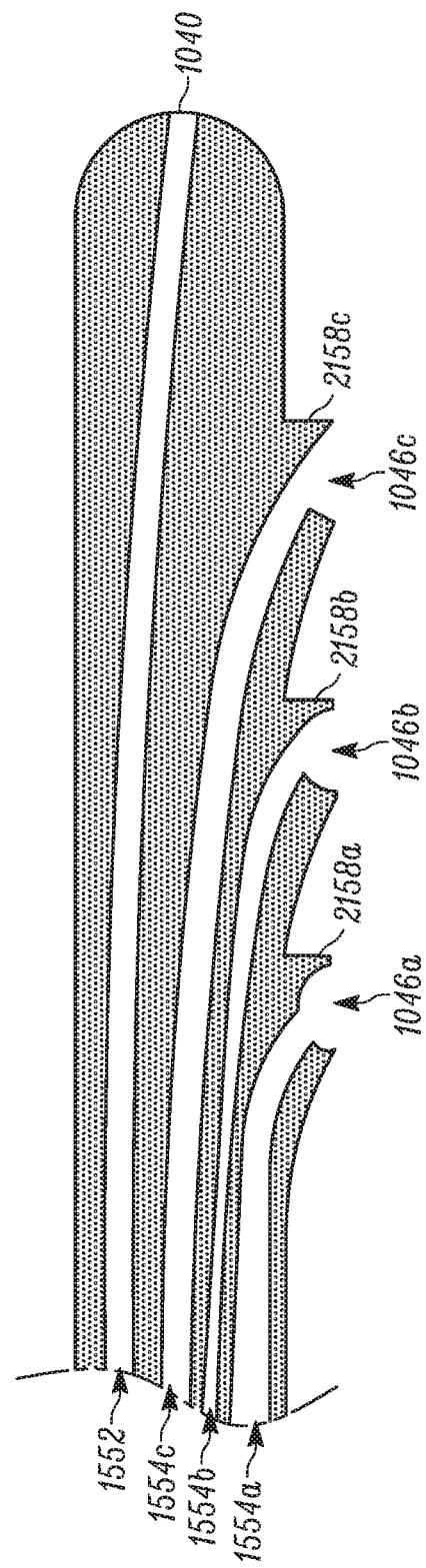
FIG. 26 is a schematic side view of the aspect of FIG. 10, including a fourth option for a component.

As shown in FIG. 23, each shaft side wall opening 1046a, 1046b, 1046c of the shaft 1030 having a plurality of shaft side wall openings 1046a, 1046b, 1046c may be circumferentially offset from one another on at least one of the shaft body 1036 and the shaft distal end 1034. In such case, as shown in FIG. 24, each shaft projection 2158a, 2158b, and 2158c, when provided, at a respective shaft side wall opening 1046a, 1046b, 1046c may accordingly be circumferentially offset from the other shaft projections 2158a, 2158b, and 2158c on at least one of the shaft body 1036 and the shaft distal end 1034. As shown in FIG. 25, instead of, or in addition to, each shaft side wall opening 1046a, 1046b, 1046c being circumferentially offset from one another on at least one of the shaft body 1036 and the shaft distal end 1034, each shaft side wall opening 1046a, 1046b, 1046c may be circumferentially aligned on at least one of the shaft body 1036 and the shaft distal end 1034. In such case, as shown in FIG. 26, each shaft projection 2158a, 2158b, and 2158c at a respective shaft side wall opening 1046a, 1046b, 1046c may accordingly be circumferentially aligned on at least one of the shaft body 1036 and the shaft distal end 1034.

As shown in FIGS. 27-32, the implant delivery system 100 including any configuration of the outer sheath 102 may be operatively joined to any configuration of the shaft 1030. For the sake of brevity, not every possible combination of the alternate configurations of the outer sheath 102 and the alternate configurations of the shaft 1030 are specifically discussed and/or depicted herein, but one of ordinary skill in the art will be able to provide a suitable configuration for a particular use environment, whether or not specifically discussed and/or depicted herein, according to the teachings of the present invention.

Figure 27:
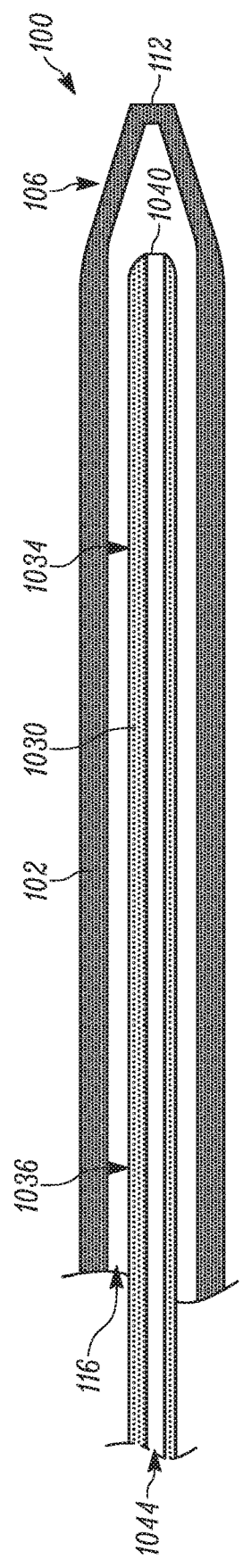
FIG. 27 is a schematic side view of an aspect of the implant delivery system in a first example use configuration.

FIG. 27 depicts the outer sheath 102 having an inwardly tapered outer sheath distal end 106 operably joined to the shaft 1030 having a substantially level shaft distal end 1034 and shaft body 1036. When the implant delivery system 100 is in the configuration shown in FIG. 27, at least one of the shaft body 1036 and the shaft distal end 1034 may be positioned within the outer sheath lumen 116.

Figure 28:
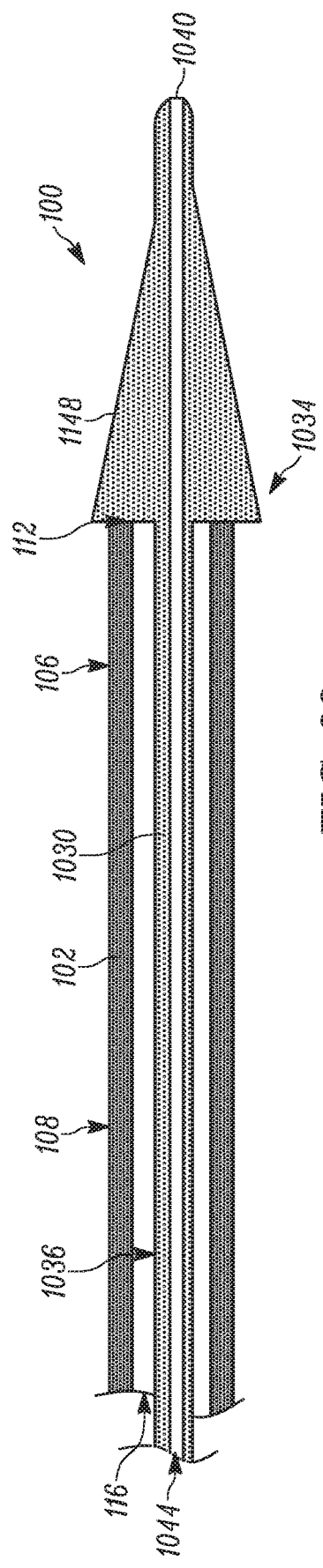
FIG. 28 is a schematic side view of an aspect of the implant delivery system in a second example use configuration.

FIG. 28 depicts the outer sheath 102 having a substantially level outer sheath distal end 106 and outer sheath body 108 operably joined to the shaft 1030 having a nosecone 1148. When the implant delivery system 100 is in the configuration shown in FIG. 28, at least one of the shaft body 1036 and the shaft distal end 1034 may be positioned within the outer sheath lumen 116. The nosecone 1148 may be longitudinally adjacent to the outer sheath open tip 112.

Figure 29:
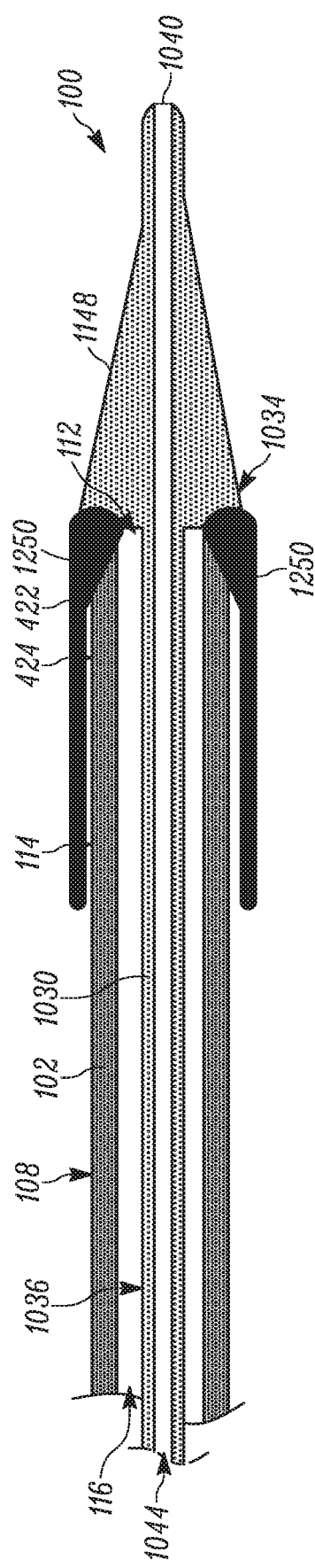
FIG. 29 is a schematic side view of an aspect of the implant delivery system in a third example use configuration.

FIG. 29 depicts the outer sheath 102 having a substantially level outer sheath distal end 106 and outer sheath body 108 operably joined to the shaft 1030 having a nosecone 1148 with at least one elastic skirt 1250. When the implant delivery system 100 is in the configuration shown in FIG. 29, at least one of the shaft body 1036 and the shaft distal end 1034 may be positioned within the outer sheath lumen 116. The nosecone 1148 may be longitudinally adjacent to the outer sheath open tip 112. The at least one elastic skirt 1250 may be disposed on outer sheath outer surface 114 to at least partially selectively restricts/inhibits/prevents the outer sheath open slit first surface 422 from at least partially elastically separating from the outer sheath open slit second surface 424 when an self-expanding implant M is disposed within the outer sheath lumen 116.

In other words, a collapsed expandable implant M placed within the outer sheath lumen 116 may tend to want to move toward an expanded condition due to the natural properties of the expandable implant M. Because the outer sheath open slit first surface 422 is elastically separable from the outer sheath open slit second surface 424, the movement of the expandable implant M toward the expanded condition may cause the outer sheath open slit first surface 422 to at least partially elastically separate from the outer sheath open slit second surface 424. However, as shown in FIG. 29, when at least one elastic skirt 1250 is positioned on the outer sheath outer surface 114, the elastic skirt 1250 provides a radially inward force to at least partially restrict/inhibit/prevent the expandable implant M from at least partially elastically separating the outer sheath open slit first surface 422 from the outer sheath open slit second surface 424.

Figure 30:
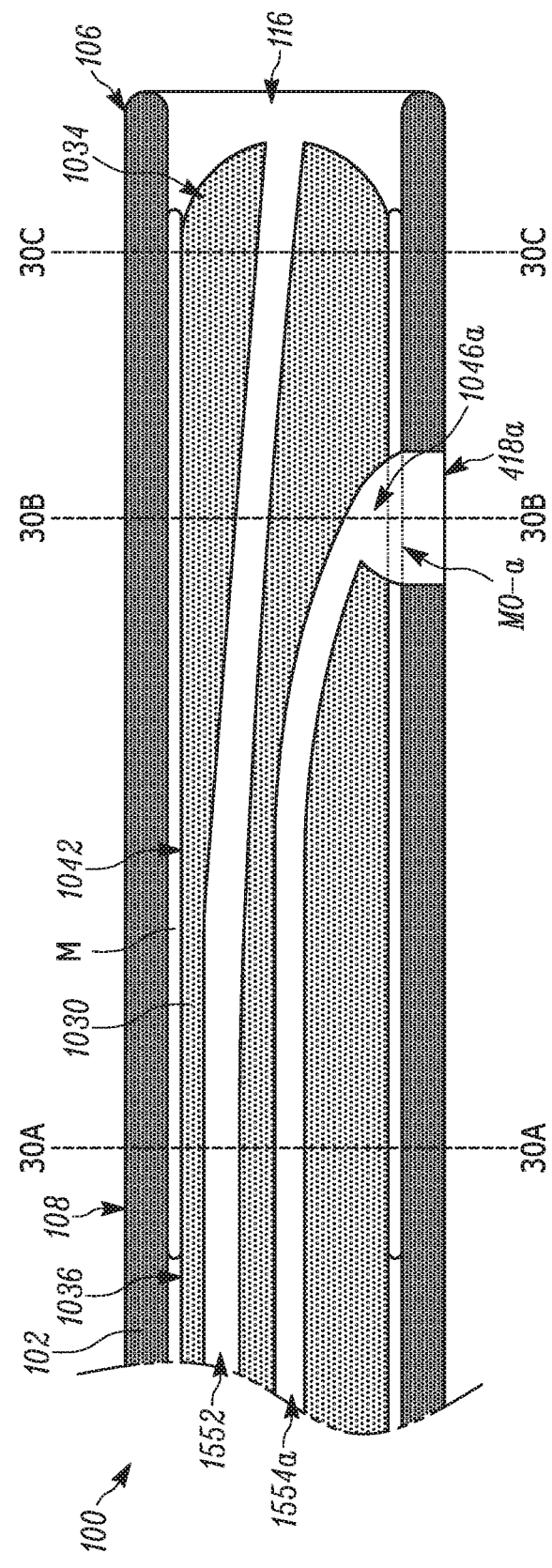
FIG. 30 is a schematic side view of an aspect of the implant delivery system in a fourth example use configuration.
Figure 30A:
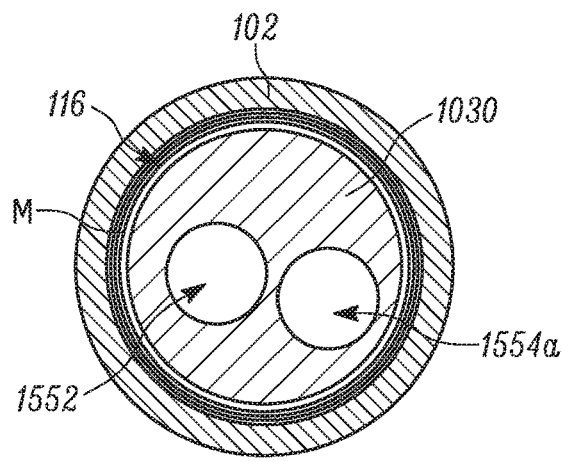
FIGS. 30a-c depict cross-sectional views of the aspect of FIG. 30.
Figure 30B:
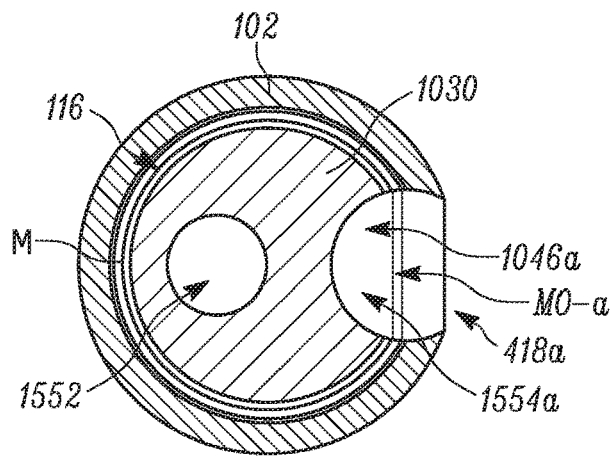
Figure 30C:
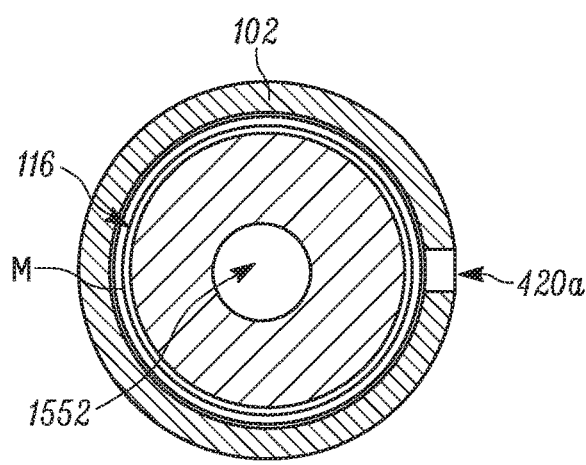
Figure 31B:
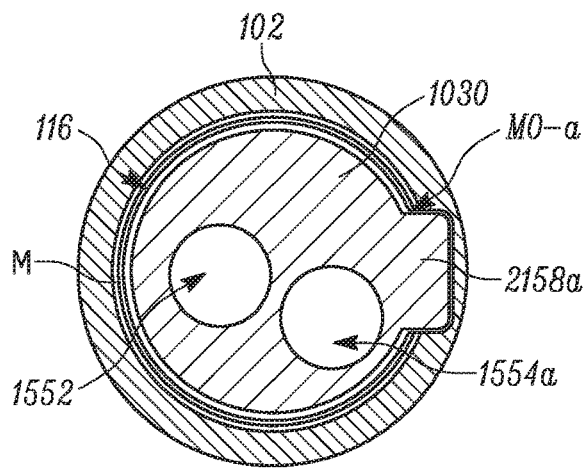
Figure 31C:
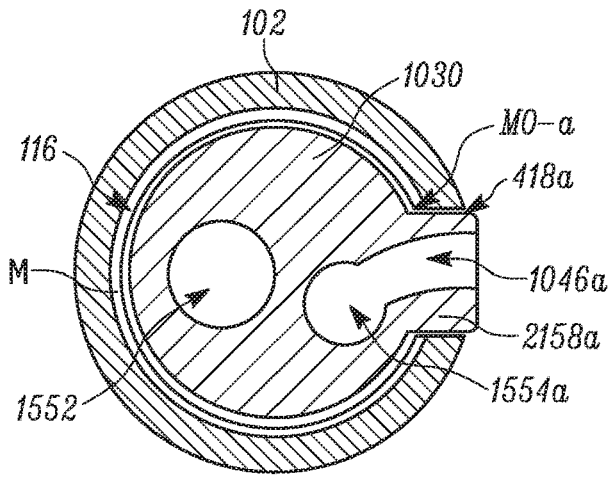
Figure 31D:
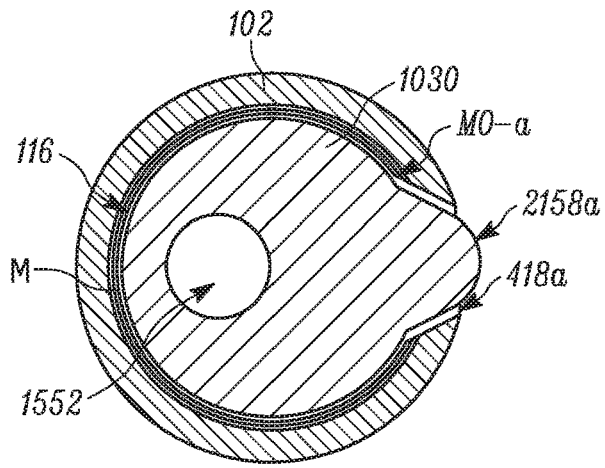
Figure 31E:
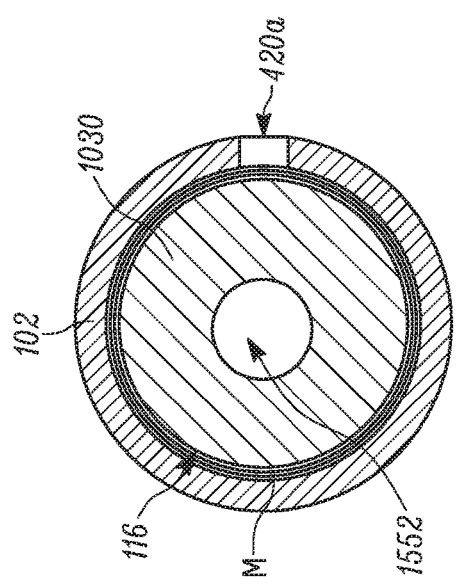

FIG. 30 depicts the outer sheath 102 having a substantially level outer sheath distal end 106 and outer sheath body 108 operably joined to the shaft 1030 having a substantially flush portion of the shaft outer surface 1042 adjacent to the at least one shaft side wall opening 1046a. When the implant delivery system 100 is in the configuration shown in FIG. 30, at least one of the shaft body 1036 and the shaft distal end 1034 may be positioned within the outer sheath lumen 116 and at least a portion of the at least one shaft side wall opening 1046a may be selectively aligned with a respective outer sheath side wall opening 418a. The shaft outer surface 1042 may have an expandable implant M disposed, alternatively referred to mounted, thereon, wherein the outer sheath lumen 116 at least partially restricts/inhibits/prevents the expandable implant M from moving from a collapsed condition toward an expanded condition. The expandable implant M may have at least one expandable implant side wall opening MO (shown here as MO-a) that is at least partially selectively aligned with at least one of a respective shaft side wall opening 1046a and a respective outer sheath side wall opening 418a when the expandable implant M is operatively joined to the shaft 1030 and the outer sheath 102. FIGS. 30a-c depict cross-sectional views of various points along the implant delivery system 100, to show the arrangement of the outer sheath 102, the shaft 1030, and the expandable implant M in FIG. 30.

Figure 32:
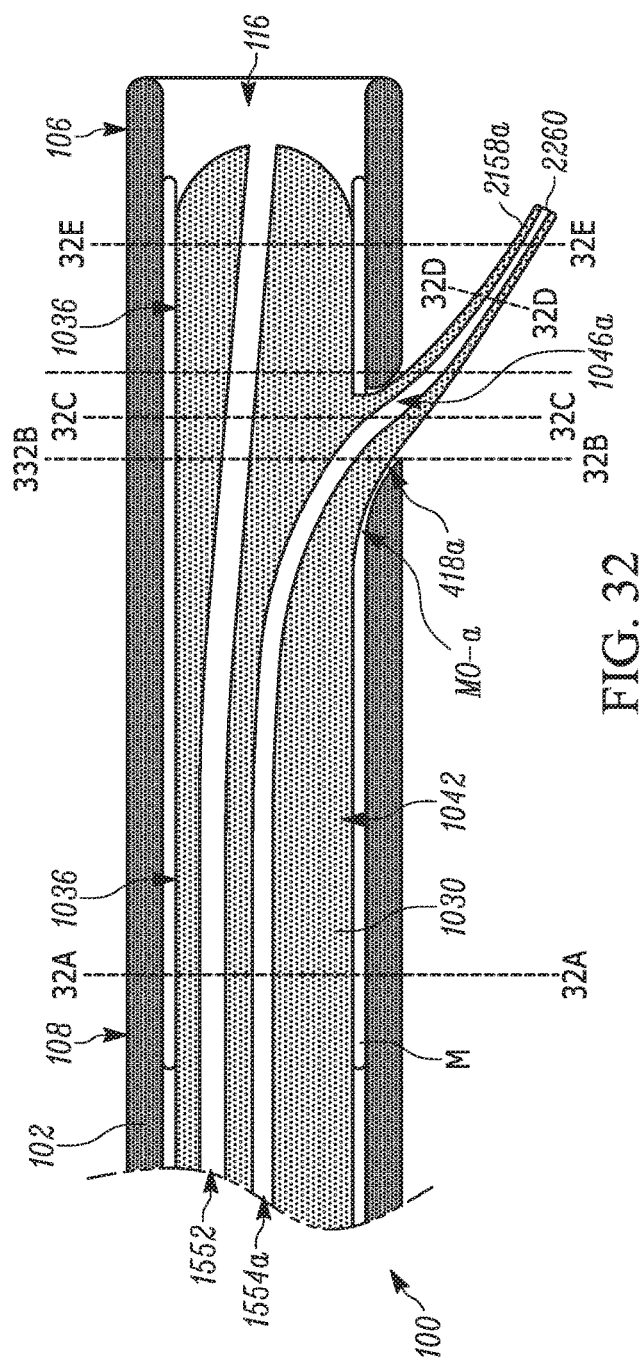
FIG. 32 is a schematic side view of an aspect of the implant delivery system in a sixth example use configuration.
Figure 32A:
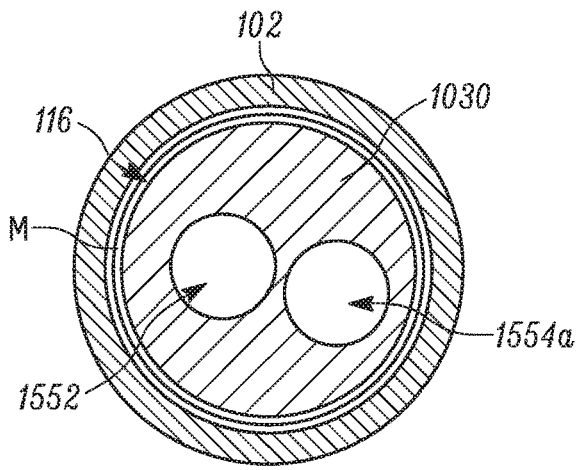
FIGS. 32a-e depict cross-sectional views of the aspect of FIG. 32.
Figure 32B:
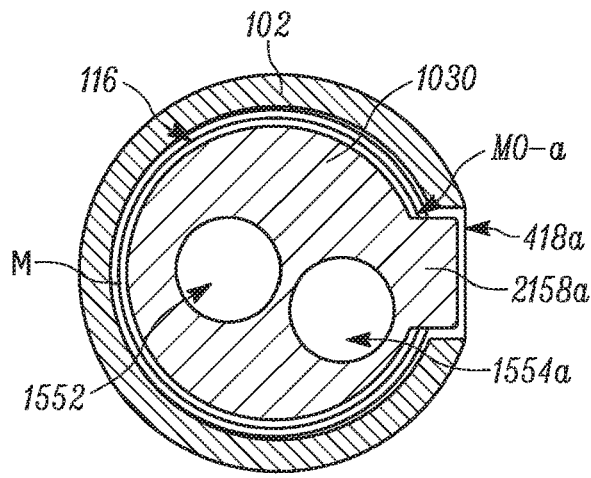
Figure 32C:
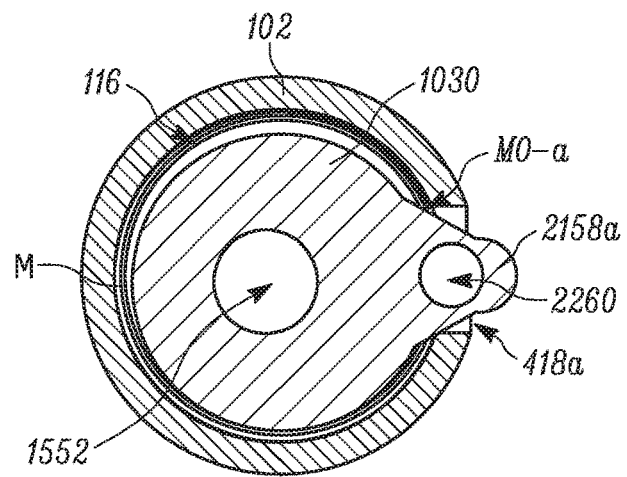
Figure 32D:
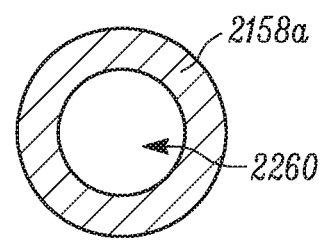
Figure 32E:
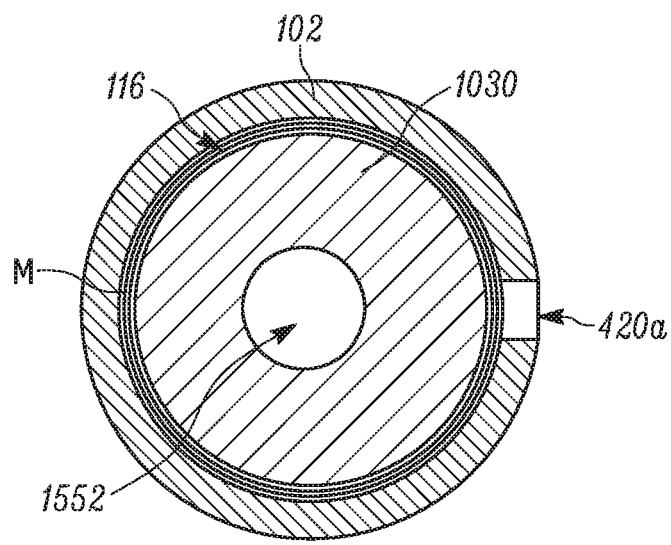

FIGS. 31-32 depicts the outer sheath 102 having a substantially level outer sheath distal end 106 and outer sheath body 108 operably joined to the shaft 1030 having the at least one shaft projection 2158a. When the implant delivery system 100 is in the configuration shown in FIGS. 31-32, at least one of the shaft body 1036 and the shaft distal end 1034 may be positioned within the outer sheath lumen 116, at least a portion of the at least one shaft side wall opening 1046a may be selectively aligned with a respective outer sheath side wall opening 418a, and at least a portion of the at least one shaft projection 2158a may at least partially extend into (FIG. 31), and/or extend through (FIG. 32), a respective outer sheath side wall opening 418a. The shaft outer surface 1042 may have an expandable implant M disposed thereon, wherein the outer sheath lumen 116 at least partially restricts/inhibits/prevents the expandable implant M from moving from a collapsed condition toward an expanded condition. The expandable implant M may have the at least one expandable implant side wall opening MO (shown here as MO-a) that is at least partially selectively aligned with at least one of a respective shaft side wall opening 1046a and a respective outer sheath side wall opening 418a when the expandable implant M is operatively joined to the shaft 1030 and the outer sheath 102. The at least one shaft projection 2158a may at least partially extend into (FIG. 31), and/or extend through (FIG. 32), a respective outer sheath side wall opening 418a, through a respective expandable implant side wall opening MO-a. FIGS. 31a-e depict cross-sectional views of various points along the implant delivery system 100, to show the arrangement of the outer sheath 102, the shaft 1030, the at least one shaft projection 2158a, and the expandable implant M depicted in FIG. 31. FIGS. 32a-e depict cross-sectional views of various points along the implant delivery system 100, to show the arrangement of the outer sheath 102, the shaft 1030, the at least one shaft projection 2158a, and the expandable implant M depicted in FIG. 32.

In use, the implant delivery system 100, as described above, is provided to the user. The implant delivery system 100 may include any configuration of the outer sheath 102, and any configuration of the shaft 1030, or a combination of individual features described above for the alternate configurations of the outer sheath 102 and the shaft 1030. For the sake of brevity, not every possible combination of the alternate configurations of the outer sheath 102 and the alternate configurations of the shaft 1030 are discussed and/or depicted. However, it is to be understood that the following description may be applicable to any combination of configurations of the outer sheath 102 and the shaft 1030 that one of ordinary skill in the art could devise, based upon the present teachings.

FIGS. 33-36 depict an example sequence of operation of the implant delivery system 100 including a shaft 1030 having a nosecone 1148 with the at least one elastic skirt 1250, the shaft first lumen 1552, and a plurality of shaft second lumens 1554a, 1554b, 1554c, and an outer sheath 102 having a substantially level outer sheath distal end 106 and outer sheath body 108, a plurality of outer sheath side wall openings 418a, 418b, 418c, and a plurality of outer sheath open slits 420a, 420b, 420c corresponding to the plurality to the outer sheath side wall openings 418a, 418b, 418c. At least one expandable implant M, which can be self-expandable and/or expand through external means (e.g., a balloon), having at least one expandable implant side wall opening MO, may be provided. For example, an expandable implant M having a plurality of expandable implant side wall openings MO-a, MO-b, MO-c may be provided.

As shown in FIG. 34, a collapsed expandable implant M may be placed in operative engagement with the shaft outer surface 1042. In particular, the expandable implant M may be mounted circumferentially on the shaft outer surface 1042. With the collapsed expandable implant M mounted on the shaft 1030, at least a portion of the at least one expandable implant side wall opening MO, e.g., the plurality of expandable implant side wall openings MO-a, MO-b, MO-c, as shown in FIG. 34, may be aligned with at least a portion of a respective shaft side wall opening 1046a, 1046b, 1046c. When the shaft 1030 has the at least one shaft projection 2158 at a respective shaft side wall opening 1046, the expandable implant M may be aligned with the shaft 1030 with the at least one expandable implant side wall opening MO-a, MO-b, MO-c aligned with a respective shaft side wall opening 1046a, 1046b, 1046c and the at least one shaft projection 2158a, 2158b, 2158c at least partially extending into, and/or extending through, a respective implant side wall opening MO-a, MO-b, MO-c.

Figure 35:
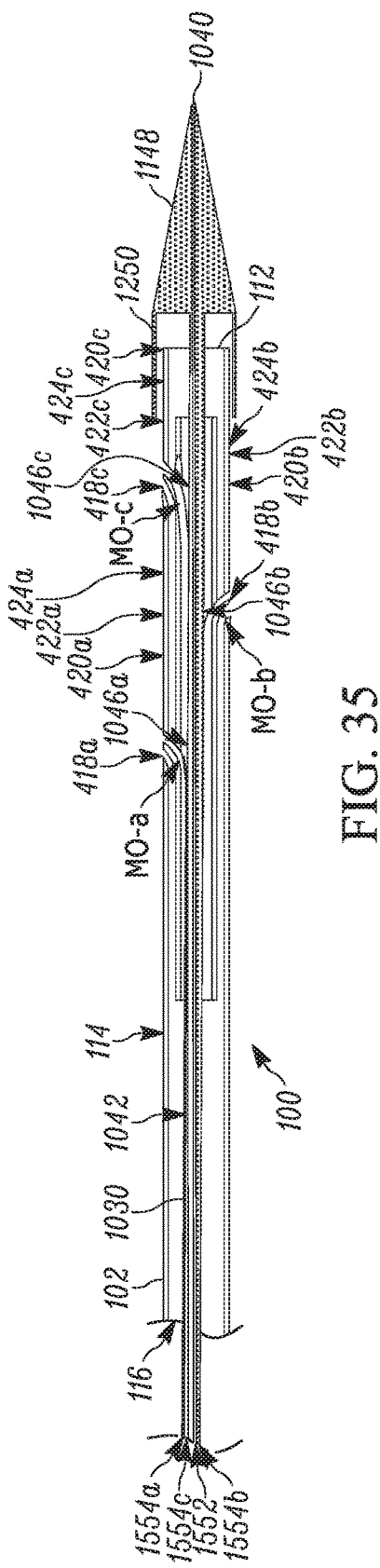

As shown in FIG. 35, with the collapsed expandable implant M mounted to the shaft outer surface 1042, at least one of the collapsed expandable implant M and at least a portion of the shaft 1030 may be collectively inserted at least partially into the outer sheath lumen 116. Alternatively, instead of mounting the expandable implant M to the shaft outer surface 1042 prior to inserting at least a portion of the shaft 1030 into the outer sheath lumen 116, the collapsed expandable implant M may be placed within the outer sheath lumen 116 prior to inserting at least a portion of the shaft 1030 into the outer sheath lumen 116. In such case, after at least a portion of the shaft 1030 is inserted into the outer sheath lumen 102, the collapsed expandable implant M may be placed in operative engagement with the shaft 1030 by mounting the expandable implant M to the shaft outer surface 1042.

With the expandable implant M and at least a portion of the shaft 1030 at least partially inserted into the outer sheath lumen 116, the shaft 1030 may be aligned in the outer sheath lumen 116 with at least a portion of the at least one shaft side wall opening 1046a, 1046b, 1046c (and accordingly also with at least a portion of the at least one expandable implant side wall opening MO-a, MO-b, MO-c) being aligned with at least a portion of a respective outer sheath side wall opening 418a, 418b, 418c. When the shaft 1030 has the at least one projection 2158a, 2158b, 2158c at a respective shaft side wall opening 1046a, 1046b, 1046c, the shaft 1030 may be aligned in the outer sheath lumen 116 with at least a portion of the at least one shaft side wall opening 1046a, 1046b, 1046c being aligned with at least a portion of a respective outer sheath side wall opening 418a, 418b, 418c and the at least one shaft projection 2158a, 2158b, 2158c at least partially extending into, and/or extending through, a respective outer sheath side wall opening 418a, 418b, 418c (and accordingly with the at least one shaft projection 2158a, 2158b, 2158c at least partially extending into, and/or extending through, a respective expandable implant side wall opening MO-a, MO-b, MO-c).

When the shaft 1030 has a nosecone 1148, as is shown in FIG. 35, the shaft 1030 may be further aligned in the outer sheath lumen 116 with the nosecone 1148 being longitudinally adjacent to the outer sheath open tip 112. When the shaft 1030 has a nosecone 1148 with the at least one elastic skirt 1250, as is shown in FIG. 35, the elastic skirt 1250 may be operatively engaged to the outer sheath 102 by placing the elastic skirt 1250 on at least a portion of the outer sheath outer surface 114 adjacent to the outer sheath open tip 112. When the elastic skirt 1250 is operatively engaged to the outer sheath 102, the elastic skirt 1250 is held in the expanded condition by the outer sheath 102. As described above, the elastic skirt 1250 at least partially selectively restricts or inhibits the outer sheath open slit first surface 422 from elastically separating from the outer sheath open slit second surface 424 when the expandable implant M is disposed within the outer sheath lumen 116.

Figure 36:
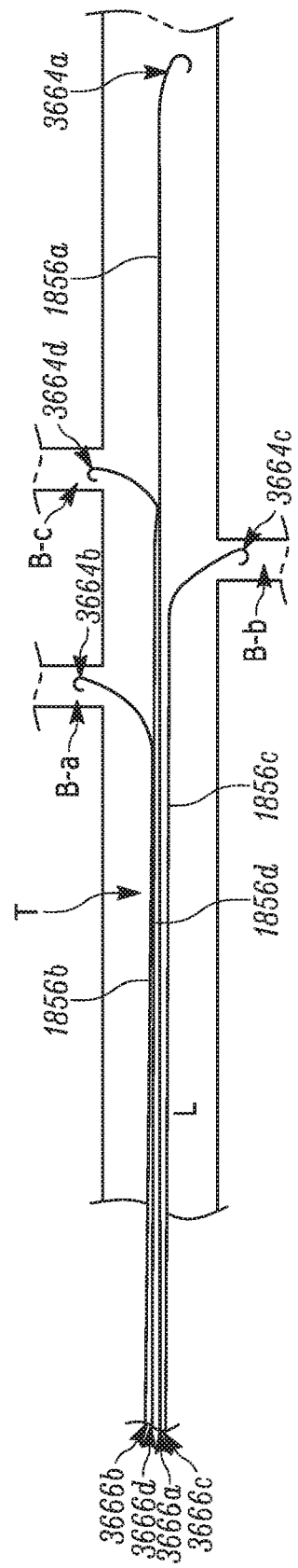
Figure 37:
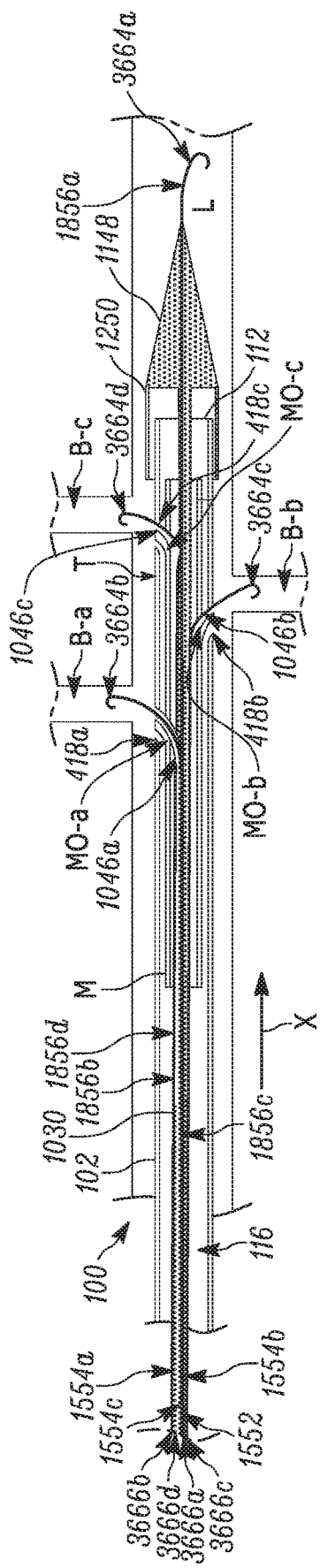

As shown in FIG. 36, at least one guidewire distal end 3664 (shown here as 3664*a*, 3664*b*, 3664*c*, and 3664*d*) is inserted into a target patient tissue site T in a patient lumen L. In particular, a first guidewire distal end 3664*a* is inserted into the target patient tissue site T in the patient lumen L, and at least one second guidewire distal end 3664*b*, 3664*c*, 3664*d* is inserted into a respective patient lumen side branch B adjacent to the target patient tissue site T. FIG. 36 depicts each of second guidewire distal ends 3664*b*, 3664*c*, 3664*d* of the plurality of second guidewire distal ends 3664*b*, 3664*c*, 3664*d* inserted into respective patient lumen side branches B (shown here as B-a, B-b, B-c). At least one guidewire proximal end 3666 (shown here as 3666*a*, 3666*b*, 3666*c*, 3666*d*) is directed through the implant delivery system 100 and the implant delivery system 100 is directed to the target patient tissue site T along the at least one guidewire 1856. In particular, a first guidewire proximal end 3666*a* may be directed through the shaft first lumen 1552, at least one second guidewire proximal end 3666*b*, 3666*c*, 3666*d* may be directed through at least one of a respective outer sheath side wall opening 418*a*, 418*b*, 418*c*, a respective expandable implant side wall opening MO-a, MO-b, MO-c, a respective shaft side wall opening 1046*a*, 1046*b*, 1046*c*, and a respective shaft second lumen 1554*a*, 1554*b*, 1554*c* and the implant delivery system 100 may be directed to the target patient tissue site T along the first guidewire 1856*a* and the at least one second guidewire 1856*b*, 1856*c*, 1856*c*. FIG. 37 depicts the implant delivery system 100, having been inserted through the vasculature and depicted at the target patient tissue site, with each of the second guidewire proximal ends 3666*b*, 3666*c*, 3666*d* of the plurality of second guidewire proximal ends 3666*b*, 3666*c*, 3666*d* inserted through a respective outer sheath side wall opening 418*a*, 418*b*, 418*c*, a respective expandable implant side wall opening MO-a, MO-b, MO-c, a respective shaft side wall opening 1046*a*, 1046*b*, 1046*c*, and a respective shaft second lumen 1554*a*, 1554*b*, 1554*c*.

As shown in FIG. 37, the implant delivery system 100 may be radially aligned at the target patient tissue site T with the at least one outer sheath side wall opening 418*a*, 418*b*, 418*c* (and accordingly a respective shaft side wall opening 1046*a*, 1046*b*, 1046*c* and a respective expandable implant side wall opening MO-a, MO-b, MO-c) being at least partially aligned with a respective patient lumen side branch B-a, B-b, B-c having a respective second guidewire distal end 3664*b*, 3664*c*, 3664*d* inserted therein. When the shaft 1030 has the at least one shaft projection 2158*a*, 2158*b*, 2158*c* at a respective shaft side wall opening 1046*a*, 1046*b*, 1046*c*, the implant delivery system 100 may be radially aligned at the target patient tissue site T with the at least one outer sheath side wall opening 418*a*, 418*b*, 418*c* being at least partially aligned with a respective patient lumen side branch B-a, B-b, B-c and at least a portion of the at least one shaft projection 2158*a*, 2158*b*, 2158*c* extending into at least a portion of a respective patient lumen side branch B-a, B-b, B-c having a respective second guidewire distal end 3664*b*, 3664*c*, 3664*d* inserted therein. However, certain configurations of shaft projections 2158*a*, 2158*b*, 2158*c* may not extend into a respective patient lumen side branch B-a, B-b, B-c when the implant delivery system 100 having the shaft 1030 with the at least one shaft projection 2158*a*, 2158*b*, 2158*c* is radially aligned at the target patient tissue site T.

Figure 38:
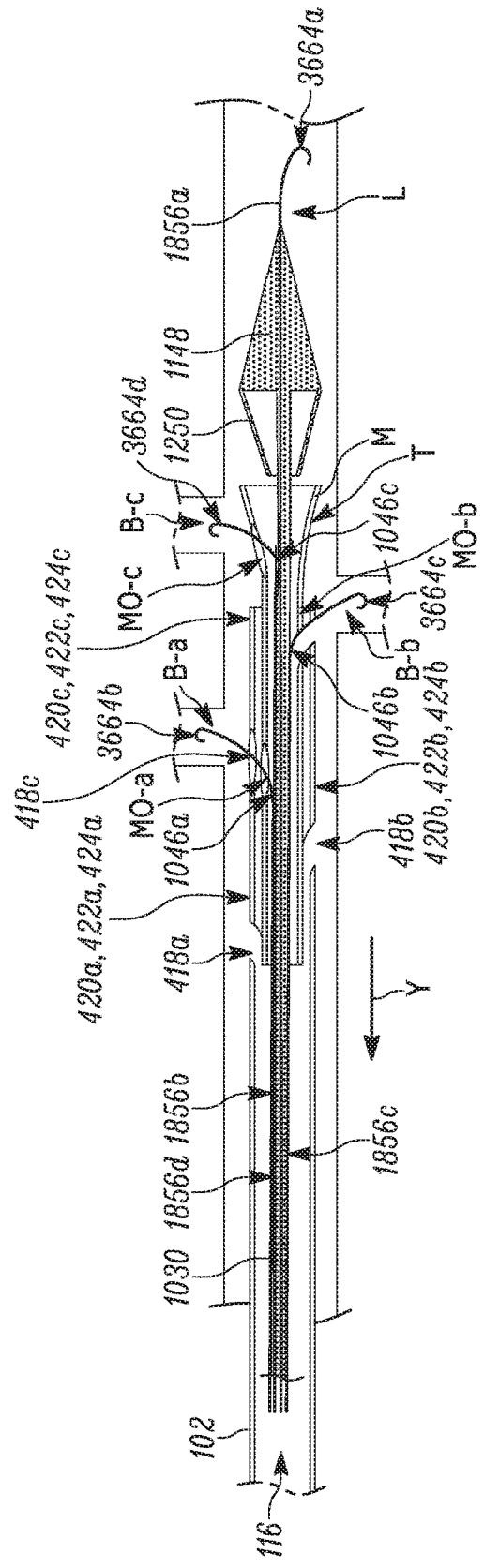

As shown in FIGS. 38-42, with the implant delivery system 100 at the target patient tissue site T, the expandable implant M may be exposed by directing the outer sheath 102 in the longitudinally proximal direction (as shown as an arrow "Y" in FIGS. 38-42). As the outer sheath 102 is directed in the longitudinally proximal direction, the outer sheath 102 operatively disengages the elastic skirt 1250, when provided, which causes the elastic skirt 1250 to move from the expanded condition (FIG. 37) to the collapsed condition (FIG. 38). As shown in FIG. 39, when the shaft 1030 does not include the at least one shaft projection 2158*a*, 2158*b*, 2158*c* at a respective shaft side wall opening 1046*a*, 1046*b*, 1046*c*, movement of the outer sheath 102 in the longitudinally proximal direction causes at least a portion of the at least one second guidewire 1856*b*, 1856*b*, 1856*c* to move along a respective outer sheath open slit 420*a*, 420*b*, 420*c* to selectively elastically separate a respective outer sheath open slit first surface 422*a*, 422*b*, 422*c* from a respective outer sheath open slit second surface 424*a*, 424*b*, 424*c* and accordingly permit the outer sheath 102 to be directed in the longitudinally proximal direction, while maintaining each of the first guidewire 1856*a*, the at least one expandable implant M, and the shaft 1030 at the target patient tissue site T and the at least one second guidewire distal end 3664*b*, 3664*c*, 3664*d* in a respective patient lumen side branch B-a, B-b, B-c.

As shown in FIGS. 40-41, when the shaft 1030 includes the at least one shaft projection 2158*a*, 2158*b*, 2158*c* at a respective shaft side wall opening 1046*a*, 1046*b*, 1046*c*, movement of the outer sheath 102 in the longitudinally proximal direction causes at least a portion of the at least one shaft projection 2158*a*, 2158*b*, 2158*c* to move along a respective outer sheath open slit 420*a*, 420*b*, 420*c* to selectively elastically separate a respective outer sheath open slit first surface 422*a*, 422*b*, 422*c* from a respective outer sheath open slit second surface 424*a*, 424*b*, 424*c* and accordingly permit the outer sheath 102 to be directed in the longitudinally proximal direction, while maintaining each of the first guidewire 1856*a*, the at least one expandable implant M, and the shaft 1030 at the target patient tissue site T and at least one of the at least one second guidewire distal end 3664*b*, 3664*c*, 3664*d* and the at least one shaft projection 2158*a*, 2158*b*, 2158*c* (FIG. 41) in a respective patient lumen side branch B-a, B-b, B-c. In other words, because the at least one shaft projection 2158*a*, 2158*b*, 2158*c* at least partially extends into, and/or through, a respective outer sheath side wall opening 418*a*, 418*b*, 418*c* before the outer sheath 102 is urged in the longitudinally proximal direction, the at least one shaft projection 2158*a*, 2158*b*, 2158*c* moves along a respective outer sheath open slit 420*a*, 420*b*, 420*c* to selectively elastically separate a respective outer sheath open slit first surface 422*a*, 422*b*, 422*c* from a respective outer sheath open slit second surface 424*a*, 424*b*, 424*c* in what could be thought of as an "unzipping"-type process.

With the expandable implant M exposed, the properties of the expandable implant M are utilized to move the at least one expandable implant from the collapsed condition, as shown in FIG. 37, toward an expanded condition, as shown in FIG. 42. As depicted in FIGS. 43-44, with the expandable implant M in the expanded condition, the shaft 1030, and/or the at least one guidewire 1856*a*, 1856*b*, 1856*c*, 1856*d*, may be removed from at least one of the target patient tissue site T and the at least one patient lumen side branch B-a, B-b, B-c.

Alternatively, after the shaft 1030 has been removed, a secondary device (not shown) may be directed over at least one of the guidewires 1856*a*, 1856*b*, 1856*c*, 1856*d* to perform a medical procedure with the secondary device at the target patient tissue site T and/or at the at least one patient lumen side branch B-a, B-b, B-c. The secondary device may be a balloon dilation device (not shown) having an expandable balloon (not shown). The balloon dilation device may be positioned with at least a portion of the expandable balloon within a diseased segment of the patient lumen L and/or adjacent to an inner surface of the expandable implant M. The expandable balloon may be inflated to dilate the diseased segment of the patient lumen L and/or cause the expandable implant M to further expand. With the expandable implant M further expanded, the expandable balloon may be deflated. At least one of the balloon dilation device and the at least one guidewire 1856a, 1856b, 1856c, 1856d may then be removed from the target patient tissue site T by moving at least one of the balloon dilation device and the at least one guidewire 1856a, 1856b, 1856c, 1856d in the longitudinally proximal direction.

Although the above description of the example sequence of operation for the implant delivery system 100 references the shaft 1030 having a nosecone 1148 with the at least one elastic skirt 1250, the shaft first lumen 1552, and the plurality of shaft second lumens 1554a, 1554b, 1554c, and the outer sheath 102 having a substantially level outer sheath distal end 106 and outer sheath body 108, the plurality of outer sheath side wall openings 418a, 418b, 418c, and the plurality of outer sheath open slits 420a, 420b, 420c corresponding to the plurality to the outer sheath side wall openings 418a, 418b, 418c, one of ordinary skill in the art will understand, given the teachings of the present application, how to similarly operate any configuration for the shaft 1030 and the outer sheath 102.

Figure 45:
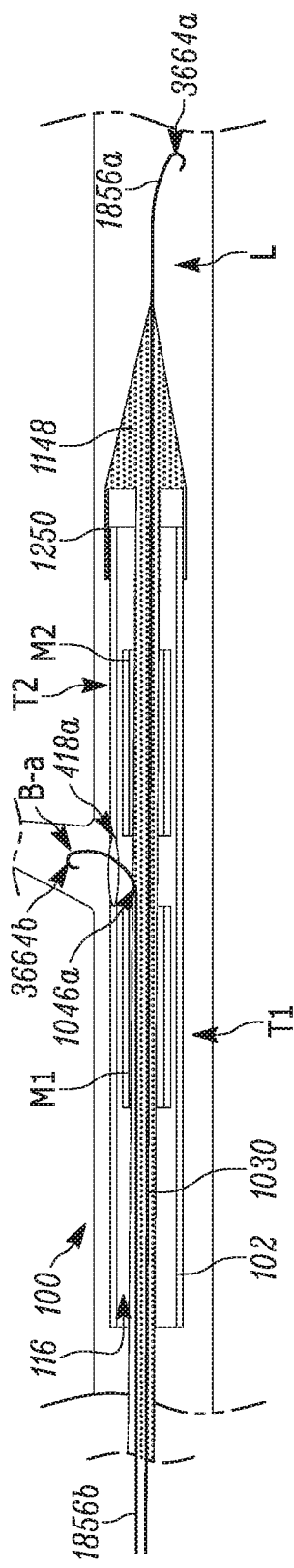
FIGS. 45-46 illustrate an example sequence of operation of a portion of the implant delivery system in a second example use configuration.
Figure 46:
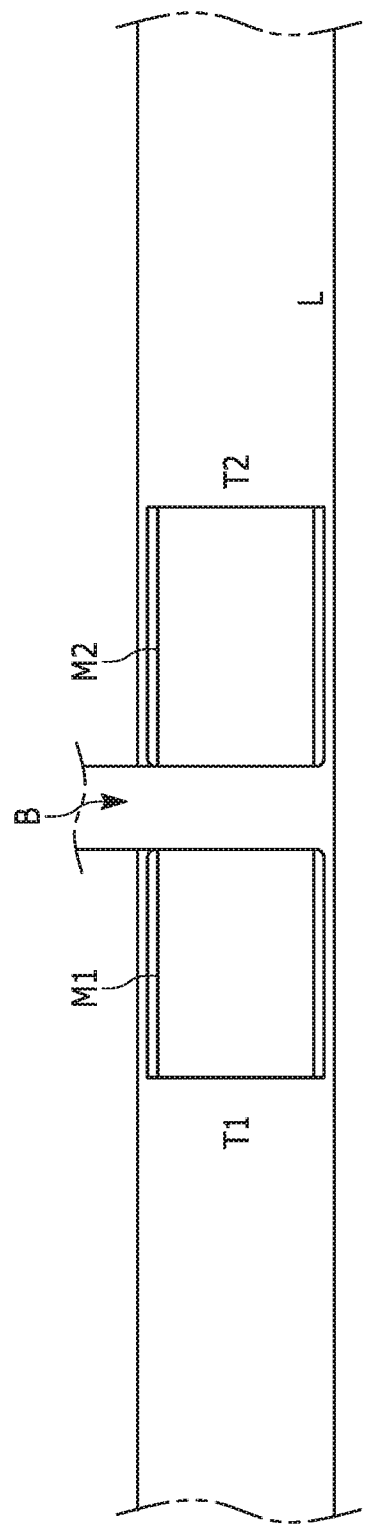

Although the above description of the example sequence of operation for the implant delivery system 100 describes an expandable implant M having at least one expandable implant side wall opening MO-a, MO-b, MO-c, the implant delivery system 100 may instead, or additionally, include at least one expandable implant M having no, or at least one, expandable implant side wall opening MO. For example, as shown in FIG. 45, the implant delivery system 100 may have two expandable implants M (shown here as M1 and M2) operatively joined to at least one of the shaft 1030 and the outer sheath 102 in a similar sequence as described above. The expandable implants M may be mounted on longitudinally opposing sides of the of the at least one shaft side wall opening 1046 (shown here as 1046a). In such case, when the shaft 1030 and the expandable implants M1, M2 are operatively joined to the outer sheath 102, the expandable implants M1, M2 may be positioned on longitudinally opposite sides of the outer sheath side wall opening 418 (shown here as 418a). As shown in FIG. 46, this configuration allows the expandable implants M to be deployed individually and serially, in a similar sequence as previously described, at a plurality of target patient tissue sites T (shown here as T1 and T2) in a patient lumen L on longitudinally opposing sides of a respective patient lumen side branch B (shown here as B-a), while a guidewire (shown here as 1856b) maintains access to the respective patient lumen side branch B-a.

It is contemplated that the implant delivery system 100 may be custom-made to match the anatomy of a patient lumen L at the target patient tissue site T. For example, the outer sheath 102 may be custom-made with at least one of the at least one outer sheath side wall opening 418 and the at least one open slit 420 being positioned on the outer sheath 102 to correspond with the at least one respective patient lumen side branch B-a, B-b, B-c at the target patient tissue site T. The shaft 1030 may be custom-made with at least one of the at least one shaft side wall opening 1046a, 1046b, 1046c being positioned on the shaft 1030 to correspond with the at least one respective patient lumen side branch B-a, B-b, B-c at the target patient tissue site T. The expandable implant M may be custom-made with at least one of the at least one expandable implant wall opening MO-a, MO-b, MO-c being positioned on the expandable implant M to correspond with the at least one respective patient lumen side branch B-a, B-b, B-c at the target patient tissue site T.

Figure 47:
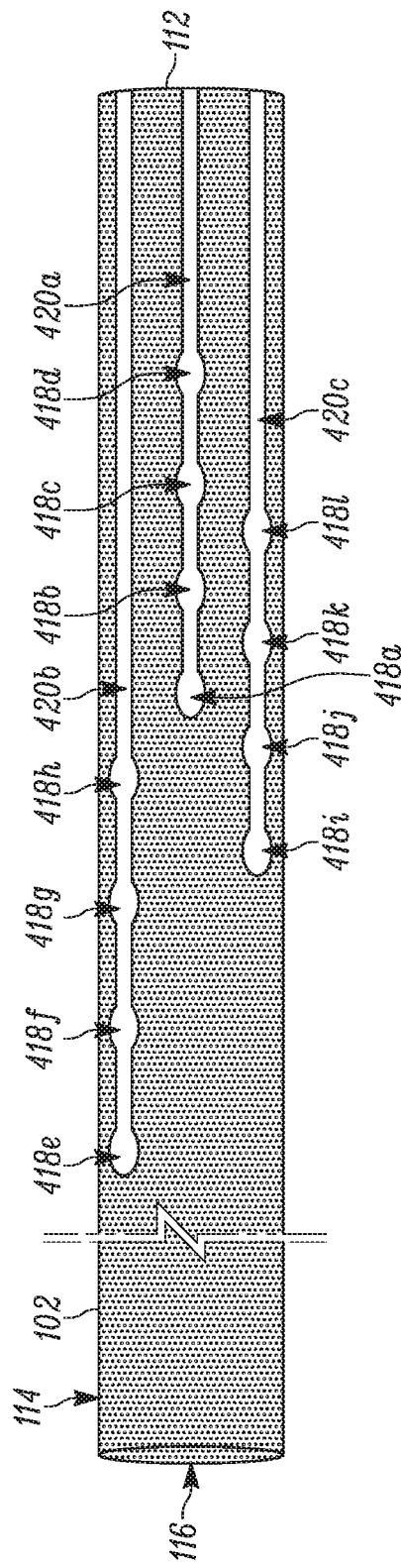
FIG. 47 is a schematic top view of the aspect of FIG. 1, including an option for a component.

Instead of, or in addition to, being custom-made, the implant delivery system 100 may be designed to in a manner that would correspond with various patient lumen L anatomies at various target patient tissue sites T. For example, as shown in FIG. 47 the outer sheath 102 may have at least one outer sheath open slit 420 (shown here as outer sheath open slits 420a, 420b, and 420c). Each outer sheath open slit 420a, 420b, 420c longitudinally extends from the outer sheath open tip 112, through at least one outer sheath side wall opening 418 (shown here as outer sheath side wall openings 418a-d, 418e-h, and 418i-l) of a respective plurality of outer sheath side wall openings 418a-d, 418e-h, 418i-l, and to another of the outer sheath side wall openings 418a-d, 418e-h, 418i-l. In such case, one having ordinary skill in the art will appreciate that, given the teachings of the present application, the outer sheath 102, as depicted in FIG. 47, may be utilized in conjunction with various of patient lumen L anatomies, various of shaft 1030 configurations, and/or various expandable implant M configurations.

Figure 48:
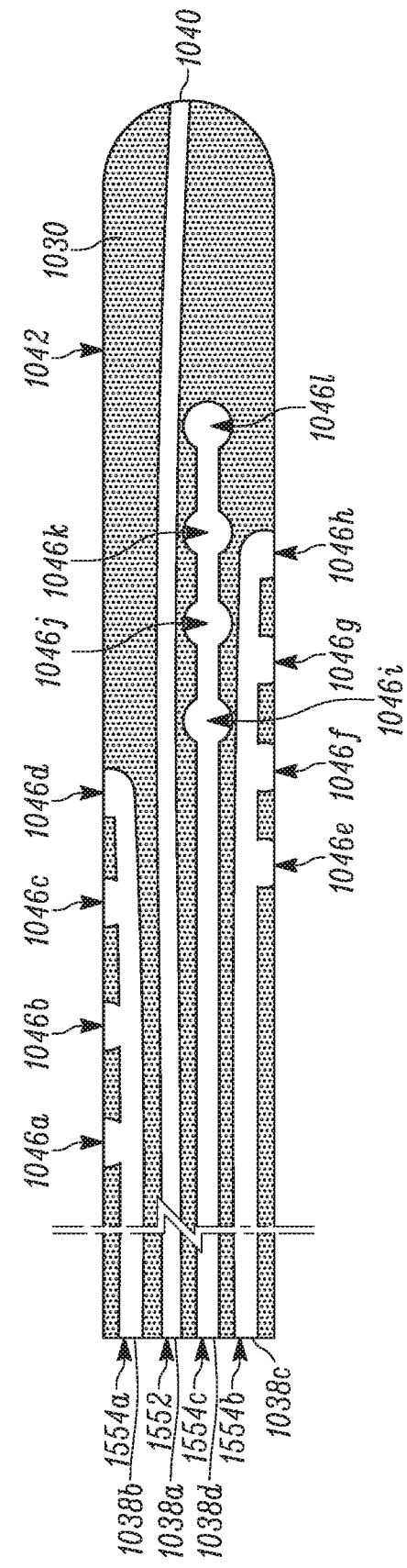
FIG. 48 is a schematic side view of the aspect of FIG. 10, including an option for a component.

As shown in FIG. 48, the shaft 1030 may have a shaft first lumen 1552 and at least one shaft second lumen 1554 (shown here as shaft second lumens 1554a, 1554b, 1554c). Each shaft second lumen 1554a, 1554b, 1554c may be selectively placed in fluid communication with the shaft outer surface 1042 through a respective plurality of shaft side wall openings 1040 (shown here as shaft side wall openings 1046a-d, 1046e-h, and 1046i-l). Thus, each shaft second lumen 1554a, 1554b, 1554c extends between the respective plurality of shaft side wall openings 1046a-d, 1046e-h, and 1046i-l and at least one of the shaft proximal end 1032, a common shaft proximal opening 1038, and a respective shaft proximal opening 1038 (shown here as shaft proximal openings 1038b, 1038c, 1038d). In such case, one having ordinary skill in the art will appreciate that, given the teachings of the present application, the shaft 1030, as depicted in FIG. 48, may be utilized in conjunction with various of patient lumen L anatomies, various outer sheath 102 configurations, and/or various expandable implant M configurations.

Any of the alternate outer sheath 102 configurations, the alternate shaft 1030 configurations, the at least one c-clip 826, when provided, the reinforcing element 928, when provided, the nosecone 1148, when provided, the elastic skirt 1250, when provided, and the at least one shaft projection 2158, when provided, of the implant delivery system 100 may be at least partially formed from silicone, polyethylene, polypropylene, stainless steel, titanium, rubber, latex, polychloroprene, nylon, any other biocompatible material, or any combination thereof.

The expandable implant M may be at least partially formed from materials having self-expanding properties, such as, but not limited to, stainless steel and shape memory materials. An example of a shape memory material is, for example, Nitinol. In such case, the expandable implant M at least partially formed from materials having self-expanding properties may be moved to the collapsed condition through a direct and/or indirect user interaction, and mounted on the shaft outer surface 1042 and/or within the outer sheath lumen 116. For example, an expandable implant M at least partially formed from a shape memory material may be cooled to a temperature below the transition temperature range, moved to the collapsed condition, and mounted on the shaft outer surface 1042 and/or within the outer sheath lumen 116. When the expandable implant M at least partially formed from a shape memory material is exposed at the target patient tissue site T, the self-expanding properties of the expandable implant M may at least partially cause the expandable implant M to move from the collapsed condition toward the expanded condition. Further, the temperature of the environment at the target patient tissue site T at least partially causes the expandable implant M at least partially formed from a shape memory material to move from the collapsed condition toward the expanded condition.

It is contemplated that an expandable implant M at least partially formed from a shape memory material may be more easily conformable to the shape of the target patient tissue site T than what an expandable implant M not made at least partially from a shape memory material would be. An expandable implant M that has self-expanding properties, but is not at least partially made from a shape memory material, may not have to be cooled in order to be moved toward the collapsed condition, and/or may not require the temperature of the of the environment at the target patient tissue site T in order to move from the collapsed condition toward the expanded condition.

It is contemplated that at least one of the alternate outer sheath 102 configurations and the alternate shaft 1030 configurations of the implant delivery system 100 may be disposed within one or more conventional sheaths (not shown) to deliver at least a portion of the implant delivery system 100 to the target patient tissue site T through a patient tissue access point.

Further, the implant delivery system 100 provides the user with the ability to advance a guidewire 1856*a* into the target patient tissue site T, advance at least one guidewire 1856*b*, 1856*c*, 1856*d* into a respective patient lumen side branch B-a, B-b, B-c, and then deploy at least one expandable implant M with at least one expandable implant side wall opening MO, and/or multiple expandable implants M with no expandable implant side wall openings MO, in a patient lumen L over the advanced guidewires 1856*a*, 1856*b*, 1856*c*, 1856*d*, while maintaining and protecting guidewire 1856*b*, 1856*c*, 1856*d* access across all respective patient lumen side branches B. For example, at least one of the second guidewire distal ends 3664*b*, the at least one outer sheath side wall opening 418, the at least one shaft side wall opening 1046, the at least one expandable implant side wall opening MO, and the at least one outer sheath open slit 420 allows the user to deploy an expandable stent M while maintaining and protecting guidewire 1856 access across all respective patient lumen side branches B because portions of the implant delivery system 100 may be inserted and removed from the target patient tissue site T without the substantial loss of access to all respective patient lumen side branches B. Further, advancing at least one guidewire 1856*b*, 1856*c*, 1856*d* into a respective patient lumen side branch B-a, B-b, B-c may allow a user to keep track of the location of the respective patient lumen side branch B-a, B-b, B-c during the deployment of the expandable implant M.

It is contemplated that the shaft 1030 having the shaft first lumen 1552 and the at least one shaft second lumen 1554*a*, 1554*b* 1554*c* may at least partially assist the user with preventing the corresponding guidewires 1856 from becoming entangled with one another when each guidewire proximal end 3666 is inserted through a respective shaft first lumen 1552 and/or a respective shaft second lumen 1554*a*, 1554*b*, 1554*c*.

It is contemplated that at least one of the alternate outer sheath configurations, the alternate shaft configurations, and the expandable implant, when provided, of the implant delivery system 100 may be prearranged, and/or pre-packaged, prior to use. For example, a shaft may be prearranged with an outer sheath such that at least one shaft projection, when provided, extends at least partially into, and/or through, at least one of a respective expandable implant side wall opening and a respective outer sheath side wall opening.

While aspects of this disclosure have been particularly shown and described with reference to the example aspects above, it will be understood by those of ordinary skill in the art that various additional aspects may be contemplated. For example, the specific methods described above for using the apparatus are merely illustrative; one of ordinary skill in the art could readily determine any number of tools, sequences of steps, or other means/options for placing the above-described apparatus, or components thereof, into positions substantively similar to those shown and described herein. In an effort to maintain clarity in the Figures, certain ones of duplicative components shown have not been specifically numbered, but one of ordinary skill in the art will realize, based upon the components that were numbered, the element numbers which should be associated with the unnumbered components; no differentiation between similar components is intended or implied solely by the presence or absence of an element number in the Figures. Any of the described structures and components could be integrally formed as a single unitary or monolithic piece or made up of separate sub-components, with either of these formations involving any suitable stock or bespoke components and/or any suitable material or combinations of materials; however, the chosen material(s) should be biocompatible for many applications. Any of the described structures and components could be disposable or reusable as desired for a particular use environment. Any component could be provided with a user-perceptible marking to indicate a material, configuration, at least one dimension, or the like pertaining to that component, the user-perceptible marking potentially aiding a user in selecting one component from an array of similar components for a particular use environment. A "predetermined" status may be determined at any time before the structures being manipulated actually reach that status, the "predetermination" being made as late as immediately before the structure achieves the predetermined status. The term "substantially" is used herein to indicate a quality that is largely, but not necessarily wholly, that which is specified—a "substantial" quality admits of the potential for some relatively minor inclusion of a non-quality item. Though certain components described herein are shown as having specific geometric shapes, all structures of this disclosure may have any suitable shapes, sizes, configurations, relative relationships, cross-sectional areas, or any other physical characteristics as desirable for a particular application. Any structures or features described with reference to one aspect or configuration could be provided, singly or in combination with other structures or features, to any other aspect or configuration, as it would be impractical to describe each of the aspects and configurations discussed herein as having all of the options discussed with respect to all of the other aspects and configurations. A device or method incorporating any of these features should be understood to fall under the scope of this disclosure as determined based upon the claims below and any equivalents thereof.

Other aspects, objects, and advantages may be obtained from a study of the drawings, the disclosure, and the appended claims.

I claim:

1. An implant delivery system, comprising:
   an outer sheath having
   an outer sheath proximal end having an outer sheath proximal opening,
   an outer sheath distal end having an outer sheath open tip,
   an outer sheath outer surface,
   an outer sheath lumen extending between the outer sheath proximal opening and the outer sheath open tip, the outer sheath lumen for selectively holding at least one expandable implant therein,
   at least one outer sheath side wall opening selectively placing the outer sheath outer surface in fluid communication with the outer sheath lumen, and
   at least one outer sheath open slit extending at least partially between the outer sheath open tip and a respective outer sheath side wall opening; and
   a shaft having
   a shaft proximal end having at least one shaft proximal opening,
   a shaft distal end having a shaft open tip,
   a shaft outer surface,
   a shaft first lumen longitudinally extending between at least one of the shaft proximal end and the at least one shaft proximal opening and at least one of the shaft distal end and the shaft open tip, and
   at least one shaft second lumen, the at least one shaft second lumen being separate from the shaft first lumen, the at least one shaft second lumen longitudinally extending between at least one of the shaft proximal end and the at least one shaft proximal opening and a respective shaft side wall opening, each shaft side wall opening selectively placing the shaft outer surface in fluid communication with a respective shaft second lumen;
   wherein when the shaft is operably joined to the outer sheath, at least a portion of the at least one shaft side wall opening is selectively aligned with a respective outer sheath side wall opening.

2. The implant delivery system of claim 1, wherein the shaft has at least one shaft projection, the shaft projection substantially radially extending from the shaft outer surface at a respective shaft side wall opening, and wherein when the shaft is operably joined to the outer sheath, the at least one shaft projection at least partially extends into a respective outer sheath side wall opening, the at least one shaft projection for facilitating the separation of an outer sheath open slit first surface and an outer sheath open slit second surface of a respective outer sheath open slit, the outer sheath open slit first surface being oppositely facing the outer sheath open slit second surface, and the outer sheath open slit first surface and the outer sheath open slit second surface being selectively elastically separable.

3. The implant delivery system of claim 1, wherein the shaft distal end has a nosecone, the nosecone pointing in a longitudinally distal direction.

4. The implant delivery system of claim 3, wherein the nosecone has at least one elastic skirt longitudinally extending in the proximal direction, the elastic skirt for selectively restricting an outer sheath open slit first surface from separating from a respective outer sheath open slit second surface when the shaft is operably joined to the outer sheath, the outer sheath open slit first surface being oppositely facing the respective outer sheath open slit second surface, the outer sheath open slit first surface and the respective outer sheath open slit second surface being selectively elastically separable.

5. The implant delivery system of claim 1, wherein the shaft has at least one shaft projection, the shaft projection substantially radially extending from the shaft outer surface at a respective shaft side wall opening, and wherein when the shaft is operably joined to the outer sheath, the at least one shaft projection at least partially extends into the at least one outer sheath side wall opening, the at least one shaft projection for facilitating the separation of an outer sheath open slit first surface and an outer sheath open slit second surface of a respective outer sheath open slit, the outer sheath open slit first surface being oppositely facing the outer sheath open slit second surface, and the outer sheath open slit first surface and the outer sheath open slit second surface being selectively elastically separable.

6. The implant delivery system of claim 5, wherein the at least one shaft projection has a shaft projection open tip and a shaft projection lumen, the shaft projection lumen extending from a respective shaft side wall opening to the shaft projection open tip and placing the shaft projection open tip in fluid communication with a respective shaft second lumen, the at least one shaft projection extends extending through a respective outer sheath side wall opening when the shaft is operably joined to the outer sheath.

7. The implant delivery system of claim 6, wherein the shaft distal end has a nosecone, the nosecone pointing in a longitudinally distal direction.

8. The implant delivery system of claim 7, wherein the nosecone has at least one elastic skirt longitudinally extending in the proximal direction, the elastic skirt for selectively restricting an outer sheath open slit first surface from separating from a respective outer sheath open slit second surface when the shaft is operably joined to the outer sheath, the outer sheath open slit first surface being oppositely facing the respective outer sheath open slit second surface, the outer sheath open slit first surface and the respective outer sheath open slit second surface being selectively elastically separable.

9. The implant delivery system of claim 1, wherein the at least one outer sheath open slit has an outer sheath open slit first surface and an outer sheath open slit second surface, the outer sheath open slit first surface being oppositely facing the outer sheath open slit second surface, the outer sheath open slit first surface and the outer sheath open slit second surface being selectively elastically separable.

10. The implant delivery system of claim 9, wherein at least one c-clip is embedded in the outer sheath radially between the outer sheath outer surface and the outer sheath lumen and radially adjacent to a respective outer sheath open slit, the c-clip at least partially selectively restricting the outer sheath open slit first surface from elastically separating from the outer sheath open slit second surface.

11. The implant delivery system of claim 9, wherein at least one reinforcing element is radially embedded in the outer sheath between the outer sheath outer surface and the outer sheath lumen and radially adjacent to the at least one outer sheath open slit, the reinforcing element at least partially extending between the at least one outer sheath side wall opening and the outer sheath open tip to at least partially reinforce a portion of the outer sheath adjacent to the at least one outer sheath open slit by at least partially selectively restricting a respective outer sheath open slit first surface from elastically separating from a respective outer sheath open slit second surface.

12. A method for deploying an expandable implant in a patient lumen, the method comprising:
    providing the implant delivery system of claim 1;
    providing at least one guidewire;
    providing at least one expandable implant having at least one expandable implant side wall opening;
    mounting the at least one collapsed expandable implant circumferentially on the shaft outer surface;
    with the at least one collapsed expandable implant mounted on the shaft, aligning at least a portion of the expandable implant side wall opening with at least a portion of a respective shaft side wall opening;
    collectively inserting the at least one collapsed expandable implant and at least a portion of the shaft into at least a portion of the outer sheath lumen;
    with the at least one expandable implant and at least a portion of the shaft inserted into the outer sheath lumen, aligning the shaft in the outer sheath lumen with at least a portion of the at least one shaft side wall opening being aligned with at least a portion of a respective outer sheath side wall opening;
    inserting a distal end of the at least one guidewire into a target patient tissue site in a patient lumen;
    directing a proximal end of the at least one guidewire through the implant delivery system;
    directing the implant delivery system to the target patient tissue site along the at least one guidewire;
    with the implant delivery system at the target patient tissue site, exposing the at least one expandable implant by directing the outer sheath in the longitudinally proximal direction, while maintaining each of the at least one guidewire, the at least one expandable implant and the shaft at the target patient tissue site; and
    with the at least one expandable implant exposed, utilizing the properties of the at least one expandable implant to move the at least one expandable implant toward an expanded condition.

13. The method of claim 12, wherein the at least one guidewire comprises a first guidewire and at least one second guidewire, the method further including:
    inserting a distal end of the first guidewire into a target patient tissue site in a patient lumen;
    inserting a distal end of the at least one second guidewire into a respective patient lumen side branch adjacent to the target patient tissue site;
    directing a proximal end of the first guidewire through the shaft first lumen;
    directing a proximal end of the at least one second guidewire through a respective outer sheath side wall opening and a respective shaft second lumen;
    directing the implant delivery system to the target patient tissue site along the first guidewire and the at least one second guidewire;
    aligning the implant delivery system at the target patient tissue site with the at least one outer sheath side wall opening being at least partially aligned with the respective patient lumen side branch having the respective second guidewire distal end inserted therein; and
    with the implant delivery system at the target patient tissue site, exposing the at least one expandable implant by urging the outer sheath in the longitudinally proximal direction, movement of the outer sheath in the longitudinally proximal direction causing at least a portion of the at least one second guidewire to move along a respective outer sheath open slit to selectively elastically separate a respective outer sheath open slit first surface from a respective outer sheath open slit second surface and accordingly permit the outer sheath to be directed in the longitudinally proximal direction, while maintaining each of the first guide wire, the at least one expandable implant and the shaft at the target patient tissue site and the at least one second guidewire distal end in the respective patient lumen side branch, the outer sheath open slit first surface oppositely facing the respective outer sheath open slit second surface, the outer sheath open slit first surface and the respective outer sheath open slit second surface being selectively elastically separable.

14. The method of claim 13, wherein the shaft distal end has a nosecone, the nosecone pointing in a longitudinally distal direction, the method further including:
    aligning the shaft with the outer sheath lumen with at least a portion of the at least one shaft side wall opening being aligned with at least a portion of a respective outer sheath side wall opening and the nosecone longitudinally adjacent to the outer sheath open tip.

15. The method of claim 14, wherein the nosecone has at least one elastic skirt longitudinally extending in the proximal direction, the elastic skirt for selectively restricting the outer sheath open slit first surface from separating from the outer sheath open slit second surface when the shaft is operably joined to the outer sheath, the method further including:
    operatively engaging the elastic skirt to the outer sheath by placing the elastic skirt on at least a portion of the outer sheath outer surface adjacent to the outer sheath open tip;
    wherein as the outer sheath is urged in the longitudinal direction, the outer sheath operatively disengages the elastic skirt.

16. The method of claim 12, wherein the at least one guidewire comprises a first guidewire and at least one second guidewire, wherein the shaft has at least one shaft projection substantially radially extending from the shaft outer surface at a respective shaft side wall opening, the method further including:
    with the collapsed expandable implant mounted on the shaft, aligning the expandable implant with the shaft with the expandable implant side wall opening aligned with a respective shaft side wall opening and the at least one shaft projection at least partially extending into a respective implant side wall opening;
    aligning the shaft in the outer sheath lumen with at least a portion of the at least one shaft side wall opening being aligned with at least a portion of a respective outer sheath side wall opening and the at least one shaft projection at least partially extending into the respective outer sheath side wall opening;
    inserting a distal end of the first guidewire into a target patient tissue site in a patient lumen;
    inserting a distal end of the at least one second guidewire into a respective patient lumen side branch adjacent to the target patient tissue site;
    directing a proximal end of the first guidewire through the shaft first lumen;
    directing a proximal end of the at least one second guidewire through a respective outer sheath side wall opening and a respective shaft second lumen;
    directing the implant delivery system to the target patient tissue site along the first guidewire and the at least one second guidewire;

aligning the implant delivery system at the target patient tissue site with the at least one outer sheath side wall opening being at least partially aligned with the respective patient lumen side branch having the respective second guidewire distal end inserted therein;

and with the implant delivery system at the target patient tissue site, exposing the at least one expandable implant by urging the outer sheath in the longitudinally proximal direction, movement of the outer sheath in the longitudinally proximal direction causing at least a portion of the at least one shaft projection to move along a respective outer sheath open slit to selectively elastically separate a respective outer sheath open slit first surface from a respective outer sheath open slit second surface and accordingly permit the outer sheath to be directed in the longitudinally proximal direction, while maintaining each of the first guide wire, the at least one expandable implant and the shaft at the target patient tissue site and the at least one second guidewire distal end in the respective patient lumen side branch, the outer sheath open slit first surface oppositely facing the respective outer sheath open slit second surface, the outer sheath open slit first surface and the respective outer sheath open slit second surface being selectively elastically separable.

17. The method of claim 16, wherein the shaft distal end has a nosecone, the nosecone pointing in a longitudinally distal direction, the method further including:
aligning the shaft with the outer sheath lumen with at least a portion of the at least one shaft side wall opening being aligned with at least a portion of a respective outer sheath side wall opening and the nosecone longitudinally adjacent to the outer sheath open tip.

18. The method of claim 17, wherein the nosecone has at least one elastic skirt longitudinally extending in the proximal direction, the elastic skirt for selectively restricting the outer sheath open slit first surface from separating from the outer sheath open slit second surface when the shaft is operably joined to the outer sheath, the method further including:
operatively engaging the elastic skirt to the outer sheath by placing the elastic skirt on at least a portion of the outer sheath outer surface adjacent to the outer sheath open tip;
wherein as the outer sheath is urged in the longitudinal direction, the outer sheath operatively disengages the elastic skirt.

19. The method of claim 16, wherein the at least one shaft projection has a shaft projection open tip and a shaft projection lumen, the shaft projection lumen extending from a respective shaft side wall opening to the shaft projection open tip and placing the shaft projection open tip in fluid communication with a respective shaft second lumen, the method further including:
with the collapsed expandable implant mounted on the shaft, aligning the expandable implant with the shaft with the expandable implant side wall opening aligned with a respective shaft side wall opening and the at least one shaft projection extending through a respective expandable implant side wall opening;
aligning the shaft in the outer sheath lumen with at least a portion of the at least one shaft side wall opening being aligned with at least a portion of a respective outer sheath side wall opening and the at least one shaft projection extending through a respective outer sheath side wall opening; and aligning the implant delivery system at the target patient tissue site with the at least one outer sheath side wall opening being at least partially aligned with the respective patient lumen side branch and at least a portion of the at least one shaft projection extending into at least a portion of the respective patient lumen side branch having the respective second guidewire distal end inserted therein.

20. The method of claim 19, wherein the shaft distal end has a nosecone, the nosecone pointing in a longitudinally distal direction, the method further including:
aligning the shaft with the outer sheath lumen with at least a portion of the at least one shaft side wall opening being aligned with at least a portion of a respective outer sheath side wall opening and the nosecone longitudinally adjacent to the outer sheath open tip.

21. The method of claim 20, wherein the nosecone has at least one elastic skirt longitudinally extending in the proximal direction, the elastic skirt for selectively restricting the outer sheath open slit first surface from separating from the outer sheath open slit second surface when the shaft is operably joined to the outer sheath, the method further including:
operatively engaging the elastic skirt to the outer sheath by placing the elastic skirt on at least a portion of the outer sheath outer surface adjacent to the outer sheath open tip;
wherein as the outer sheath is urged in the longitudinal direction, the outer sheath operatively disengages the elastic skirt.

22. The implant delivery system of claim 1, wherein the shaft first lumen longitudinally extends between the at least one shaft proximal opening and the shaft open tip, the at least one shaft second lumen being fluidically isolated from the shaft open tip.

23. An implant delivery system, comprising:
an outer sheath having
an outer sheath proximal end having an outer sheath proximal opening,
an outer sheath distal end having an outer sheath open tip,
an outer sheath outer surface,
an outer sheath lumen extending between the outer sheath proximal opening and the outer sheath open tip, the outer sheath lumen for selectively holding at least one expandable implant therein,
at least one outer sheath side wall opening selectively placing the outer sheath outer surface in fluid communication with the outer sheath lumen, and
at least one outer sheath open slit extending at least partially between the outer sheath open tip and a respective outer sheath side wall opening; and
a shaft having
a shaft proximal end having at least one shaft proximal opening,
a shaft distal end having a shaft open tip,
a shaft outer surface,
at least one shaft lumen,
a shaft first lumen longitudinally extending between at least one of the shaft proximal end and the at least one shaft proximal opening and at least one of the shaft distal end and the shaft open tip, and
a plurality of shaft second lumens, each of the shaft second lumens longitudinally extending between at least one of the shaft proximal end and the at least one shaft proximal opening and a respective shaft side wall opening, each of the shaft side wall openings selectively placing the shaft outer surface in fluid communication with a respective shaft second lumen;

wherein when the shaft is operably joined to the outer sheath, at least a portion of the at least one shaft side wall opening is selectively aligned with a respective outer sheath side wall opening.

24. The implant delivery system of claim 23, wherein the at least one outer sheath side wall opening comprises a plurality of outer sheath side wall openings, and the at least one outer sheath open slit comprises a plurality of outer sheath open slits, each of the outer sheath open slits extending between the outer sheath open tip and a respective outer sheath side wall opening.

25. The implant delivery system of claim 24, wherein the shaft has at least one shaft projection, the shaft projection substantially radially extending from the shaft outer surface at a respective shaft side wall opening, and wherein when the shaft is operably joined to the outer sheath, the at least one shaft projection at least partially extends into a respective outer sheath side wall opening, the at least one shaft projection for facilitating the separation of an outer sheath open slit first surface and an outer sheath open slit second surface of a respective outer sheath open slit, the outer sheath open slit first surface being oppositely facing the outer sheath open slit second surface, and the outer sheath open slit first surface and the outer sheath open slit second surface being selectively elastically separable.

26. The implant delivery system of claim 24, wherein the shaft distal end has a nosecone, the nosecone pointing in a longitudinally distal direction.

27. The implant delivery system of claim 26, wherein the nosecone has at least one elastic skirt longitudinally extending in the proximal direction, the elastic skirt for selectively restricting an outer sheath open slit first surface from separating from a respective outer sheath open slit second surface when the shaft is operably joined to the outer sheath, the outer sheath open slit first surface being oppositely facing the respective outer sheath open slit second surface, the outer sheath open slit first surface and the respective outer sheath open slit second surface being selectively elastically separable.

28. The implant delivery system of claim 23, wherein the at least one outer sheath side wall opening comprises a plurality of outer sheath side wall openings longitudinally arranged in parallel on the outer sheath, and the at least one outer sheath open slit extends from the outer sheath open tip, through at least one of the outer sheath side wall openings of the plurality of outer sheath side wall openings, and to another of the outer sheath side wall openings, and wherein the at least one of the plurality of side wall openings that the at least one outer sheath open slit extends through forms a portion of the outer sheath open slit.

29. The implant delivery system of claim 28, wherein the shaft has at least one shaft projection, the shaft projection substantially radially extending from the shaft outer surface at a respective shaft side wall opening, and wherein when the shaft is operably joined to the outer sheath, the at least one shaft projection at least partially extends into a respective outer sheath side wall opening, the at least one shaft projection for facilitating the separation of an outer sheath open slit first surface and an outer sheath open slit second surface of a respective outer sheath open slit, the outer sheath open slit first surface being oppositely facing the outer sheath open slit second surface, and the outer sheath open slit first surface and the outer sheath open slit second surface being selectively elastically separable.

30. The implant delivery system of claim 28, wherein the shaft distal end has a nosecone, the nosecone pointing in a longitudinally distal direction.

31. The implant delivery system of claim 30, wherein the nosecone has at least one elastic skirt longitudinally extending in the proximal direction, the elastic skirt for selectively restricting an outer sheath open slit first surface from separating from a respective outer sheath open slit second surface when the shaft is operably joined to the outer sheath, the outer sheath open slit first surface being oppositely facing the respective outer sheath open slit second surface, the outer sheath open slit first surface and the respective outer sheath open slit second surface being selectively elastically separable.

* * * * *